US012708699B2

(12) United States Patent
Hickey et al.

(10) Patent No.: US 12,708,699 B2
(45) Date of Patent: Aug. 18, 2026

(54) COMPOSITE BIOMATERIALS

(71) Applicants: Spiderwort Inc., Ottawa (CA); University of Ottawa, Ottawa (CA)

(72) Inventors: Ryan Hickey, Ottawa (CA); Andrew E. Pelling, Ottawa (CA); Santiago Campuzano, Ottawa (CA); Paula Cristina de Sousa Faria Tischer, Londrina (BR); Kama Szereszewski, Ottawa (CA)

(73) Assignees: Spiderwort Biotechnologies Inc., Ottawa (CA); University of Ottawa, Ottawa (CA)

( * ) Notice: Subject to any disclaimer, the term of this patent is extended or adjusted under 35 U.S.C. 154(b) by 1093 days.

(21) Appl. No.: 17/611,035

(22) PCT Filed: May 14, 2020

(86) PCT No.: PCT/CA2020/050655
§ 371 (c)(1),
(2) Date: Nov. 12, 2021

(87) PCT Pub. No.: WO2020/227835
PCT Pub. Date: Nov. 19, 2020

(65) Prior Publication Data

US 2022/0296783 A1 Sep. 22, 2022

Related U.S. Application Data

(60) Provisional application No. 62/847,619, filed on May 14, 2019.

(51) Int. Cl.

| | |
|---|---|
| ***A61L 27/52*** | (2006.01) |
| ***A61L 27/22*** | (2006.01) |
| ***A61L 27/36*** | (2006.01) |
| ***B33Y 10/00*** | (2015.01) |
| ***B33Y 70/00*** | (2020.01) |
| ***B33Y 80/00*** | (2015.01) |

(52) U.S. Cl.
CPC ............. *A61L 27/52* (2013.01); *A61L 27/222* (2013.01); *A61L 27/3637* (2013.01); *B33Y 10/00* (2014.12); *B33Y 70/00* (2014.12); *B33Y 80/00* (2014.12); *A61L 2300/232* (2013.01); *A61L 2400/08* (2013.01)

(58) Field of Classification Search
None
See application file for complete search history.

(56) References Cited

U.S. PATENT DOCUMENTS

| | | | |
|---|---|---|---|
| 5,166,187 A | 11/1992 | Collombel et al. | |
| 2005/0009178 A1 | 1/2005 | Yost et al. | |
| 2007/0010831 A1 | 1/2007 | Romero-Ortega et al. | |
| 2008/0187591 A1* | 8/2008 | Rhee ....................... | A61L 24/06 424/94.64 |
| 2009/0209982 A1 | 8/2009 | Hoerstrup et al. | |
| 2013/0224278 A1 | 8/2013 | Czaja et al. | |
| 2013/0344036 A1 | 12/2013 | Yliperttula et al. | |
| 2014/0227783 A1 | 8/2014 | Masutani et al. | |
| 2015/0051687 A1 | 2/2015 | Dickerhoff et al. | |
| 2016/0053231 A1 | 2/2016 | Xu | |
| 2019/0060520 A1 | 2/2019 | Pelling et al. | |
| 2021/0154371 A1 | 5/2021 | Allen et al. | |

FOREIGN PATENT DOCUMENTS

| | | |
|---|---|---|
| AU | 2013222371 B2 | 8/2014 |
| AU | 2017218476 B2 | 2/2022 |
| CA | 2815276 A1 | 5/2012 |
| CN | 101404977 B | 9/2012 |
| CN | 103224565 A | 7/2013 |
| EP | 2633032 B1 | 2/2015 |
| WO | 2008107384 A1 | 9/2008 |
| WO | 2012056109 A2 | 5/2012 |
| WO | 2013126635 A1 | 8/2013 |
| WO | 2014074134 A1 | 5/2014 |
| WO | 2015022078 A1 | 2/2015 |
| WO | 2017136950 A1 | 8/2017 |

(Continued)

OTHER PUBLICATIONS

Afewerki, S. et al. "Gelatin-Polysaccharide Composite Scaffold for 3D cell culture and Tissue Engineering: Towards Natural Therapeutics". Bioengineering & Translational Medicine. Nov. 2018. vol. 4, pp. 96-115 ISSN:2380-6761.
Bottan, S.et al. "Surface-Structured Bacterial Cellulose with Guided Assembly-Based Biolithography (GAB)". ACS Nano. 2015. vol. 9, pp. 206-219, ISSN: 1936-086X.
Hickey, R. et al. "Customizing the Shape and Microenvironment Biochemistry of Biocompatible Macroscopic Plant-Derived Cellulose Scaffolds". ACS Biomaterials Science &Engineering. 2018. vol. 4, pp. 3726-3736 ISSN:2373-9878.
Hickey, R. et al. "Cellulose Biomaterials for Tissue Engineering". Frontiers in Bioengineering and Biotechnology. Mar. 2019. vol. 7, Article 45, ISSN: 2296-4185.

(Continued)

*Primary Examiner* — Nicole P Babson
(74) *Attorney, Agent, or Firm* — Lisa Mueller; Casimir Jones SC

(57) ABSTRACT

Provided herein are composite scaffold biomaterials including two or more scaffold biomaterial subunits, each including a decellularized plant or fungal tissue from which cellular materials and nucleic acids of the tissue are removed, the decellularized plant or fungal tissue having a 3-dimensional porous structure, the two or more scaffold biomaterial subunits being assembled into the composite scaffold biomaterial and held together via gel casting using a hydrogel glue; via complementary interlocking geometry of the two or more scaffold biomaterial subunits; via guided assembly based biolithography (GAB); via chemical cross-linking; or any combinations thereof. Methods for producing such scaffold biomaterials, as well as methods and uses thereof, are also provided.

18 Claims, 35 Drawing Sheets

(56) References Cited

FOREIGN PATENT DOCUMENTS

| | | | |
|---|---|---|---|
| WO | 2017160862 | A1 | 9/2017 |
| WO | 2018050092 | A1 | 3/2018 |
| WO | 2018200816 | A1 | 11/2018 |
| WO | 2020041612 | A1 | 2/2020 |
| WO | 2020214964 | A1 | 10/2020 |
| WO | 2020264385 | A1 | 12/2020 |

OTHER PUBLICATIONS

Fontana, G. et al. "Biofunctionalized plants as Diverse Biomaterials for Human Cell Culture". Advanced Healthcare Materials. 2017. vol. 6, pp. 1-16 ISSN:2192-2659.

Gershlak, J. R. "Crossing Kingdoms:Using Decellularized Plants as Perfusable Tissue Engineering Scaffolds". Biomaterials. 2017. vol. 125, pp. 13-22 ISSN:1878-5905.

Modulevsky, D. J. et al. Apple derived cellulose scaffolds for 3D mammalian cell culture. PLoS One 2014 (May 1, 2014), vol. 9 (5), pp. e97835 1-10.

Nicholas Miliaras, Apple Does 3D Cell Culture, ASCB, Sep. 10, 2014, available at : https://www.ascb.org/science-news/apple-does-3d-cell-culture/.

Modulevsky, D., et al., "Open Source Biomaterials for Regenerative Medicine." O'Reilly, BioCoder 8, pp. 17-28 (Jul. 2015).

Modulevsky, D., et al., "DIY Open Source Biomaterials" O'Reilly, BioCoder 8, pp. 43-57 (Jul. 2015).

Andrew Pelling, "Putting Cells Where They Don't Belong,"14th Annual Chemical Biophysics Symposium (CBP), Toronto, Canada Apr. 10-12, 2015, Abstract of Oral Presentation, session III, Fri 7:50 pm.

* cited by examiner

FIGURE 4
A
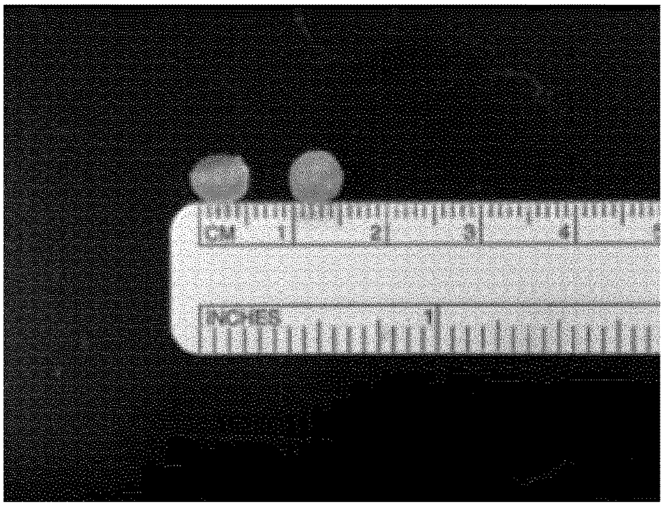
B
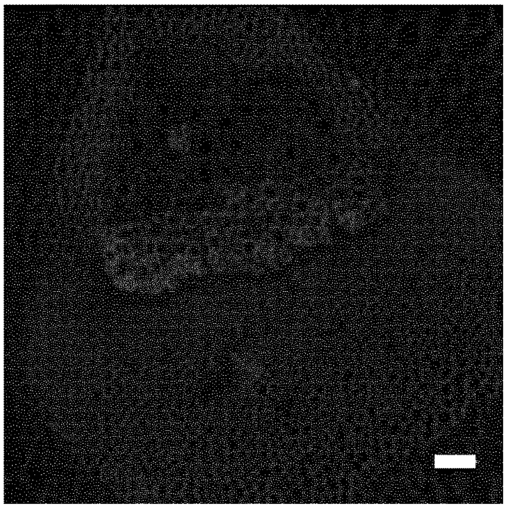

A B

A B

Carbonyl bonds in esters gives peaks at 1740 $cm^{-1}$

Carboxylic acids exhibits a band at 1700 $cm^{-1}$

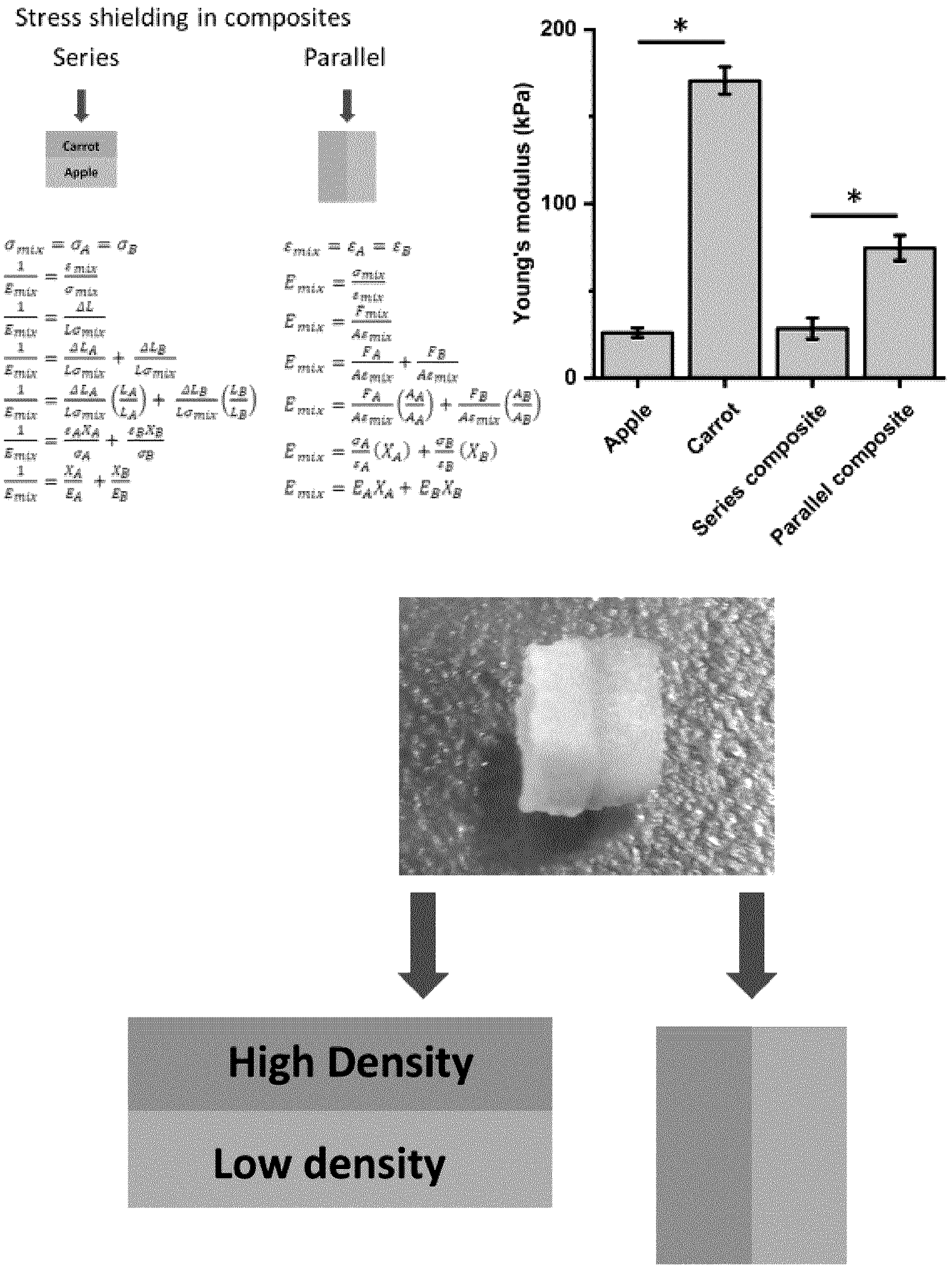

FIGURE 16

Series $$\sigma_{mix} = \sigma_A = \sigma_B$$
$$\frac{1}{E_{mix}} = \frac{\varepsilon_{mix}}{\sigma_{mix}}$$
$$\frac{1}{E_{mix}} = \frac{\Delta L}{L\sigma_{mix}}$$
$$\frac{1}{E_{mix}} = \frac{\Delta L_A}{L\sigma_{mix}} + \frac{\Delta L_B}{L\sigma_{mix}}$$
$$\frac{1}{E_{mix}} = \frac{\Delta L_A}{L\sigma_{mix}}\left(\frac{L_A}{L_A}\right) + \frac{\Delta L_B}{L\sigma_{mix}}\left(\frac{L_B}{L_B}\right)$$
$$\frac{1}{E_{mix}} = \frac{\varepsilon_A X_A}{\sigma_A} + \frac{\varepsilon_B X_B}{\sigma_B}$$
$$\frac{1}{E_{mix}} = \frac{X_A}{E_A} + \frac{X_B}{E_B}$$

Parallel $$\varepsilon_{mix} = \varepsilon_A = \varepsilon_B$$
$$E_{mix} = \frac{\sigma_{mix}}{\varepsilon_{mix}}$$
$$E_{mix} = \frac{F_{mix}}{A\varepsilon_{mix}}$$
$$E_{mix} = \frac{F_A}{A\varepsilon_{mix}} + \frac{F_B}{A\varepsilon_{mix}}$$
$$E_{mix} = \frac{F_A}{A\varepsilon_{mix}}\left(\frac{A_A}{A_A}\right) + \frac{F_B}{A\varepsilon_{mix}}\left(\frac{A_B}{A_B}\right)$$
$$E_{mix} = \frac{\sigma_A}{\varepsilon_A}(X_A) + \frac{\sigma_B}{\varepsilon_B}(X_B)$$
$$E_{mix} = E_A X_A + E_B X_B$$

High Density

Low density

COMPOSITE BIOMATERIALS

FIELD OF INVENTION

The present invention relates generally to scaffold biomaterials. More specifically, the present invention relates to composite scaffold biomaterials comprising decellularized plant and/or fungal tissue, such as those comprising two or more scaffold biomaterial subunits.

BACKGROUND

Living tissues are complex structures consisting of a collection of different cell types. Various cell types may interact to perform specialized functions within the body. Cellular and extracellular matrix organization is often directly related to function; consequently, impaired cellular, tissue, and/or organ function may result from both biochemical and physical defects, ranging from genetic disorders to physical injuries. Biochemical and physical environments in the body may vary within, at the interface, and between different tissue types and organs. As such, recreating or approximating the natural in vivo environment of the cell is difficult.

Substantial research has been directed toward producing biomimetic constructs. A variety of approaches have been proposed as potential avenues to recapture or mimic the native environment including synthetic biology, regenerative medicine, grafting, templating, and scaffolding. However, recreation of the cellular microenvironment has been challenging. As tissues are themselves complex composite materials, simple materials typically do not allow for biochemical and physical complexity to mimic the natural environment. Thus, extensive research has been dedicated to composite materials developed from one or more of the aforementioned approaches to biomaterial production.

An attractive approach for biomaterial design is decellularization, wherein a scaffolding material made of the animal ECM proteins but void of cells replaces the damaged tissue. This concept is based on an idea that the damaged tissue may be replaced with a scaffold of the same tissue or organ; the scaffold may be repopulated by healthy cells, and proper tissue or organ function may be restored. Typically such organ decellularization approaches have had several challenges including reliance on donor tissue, compatibility issues, and practical limitations.

Alternatively, synthetic approaches may provide several other biomaterial production methods including 3D printing, casting, and electrospinning which have been developed to create custom structures that attempt to circumvent certain shortcomings of the organ decellularization approach. However, the development of synthetic scaffold biomaterials mimicking animal tissues and/or conditions has proven difficult in the field, particularly since providing complexity approaching that of living organisms has been challenging.

Nonetheless, scaffolds which can be tailored to mimic in vivo tissues or conditions are highly sought after, particularly in the fields of tissue regeneration and/or repair, bone engineering, and wound healing, for example.

Furthermore, with the sustainability and environmental concerns associated with global meat consumption, lab-grown and/or meat alternative food products are highly sought after in the industry. However, producing mouth-feel and/or taste experience of traditional meat food products has proven to be a difficult challenge facing the industry.

Alternative, additional, and/or improved scaffold biomaterials are desirable.

SUMMARY OF INVENTION

Provided herein are composite scaffold biomaterials including two or more scaffold biomaterial subunits, each including a decellularized plant or fungal tissue from which cellular materials and nucleic acids of the tissue are removed, the decellularized plant or fungal tissue having a 3-dimensional porous structure, the two or more scaffold biomaterial subunits being assembled into the composite scaffold biomaterial and held or associated together, for example via gel casting using a hydrogel glue; via complementary interlocking geometry of the two or more scaffold biomaterial subunits; via guided assembly based biolithography (GAB); via chemical cross-linking; or any combinations thereof. Methods for producing such scaffold biomaterials, as well as methods and uses thereof, are also provided. Scaffold biomaterials may be produced for a variety of different applications, including but not limited to medical applications and/or applications in the food industry as plant-derived meat alternatives.

In certain embodiments, scaffold biomaterials as described herein may optionally comprise two or more scaffold biomaterial subunits. By combining two or more subunits, a variety of benefits may be achieved. By way of example, through selection of individual subunits and characteristics thereof, the complexity of resultant scaffold biomaterials following subunit assembly may be significantly increased, and characteristics of the resultant scaffold biomaterials (globally, at particular sites or regions, or both) can be tailored or customized to suit particular applications as desired through appropriate design and selection of subunits and techniques for assembly and linkage thereof. As well, by combining two or more subunits, larger constructs may be prepared without encountering difficulties associated with decellularizing larger structures and/or without being limited by dimensions imposed by plant and/or fungal source materials. Described herein are a variety of subunits that have been developed, as well as a variety of assembly techniques and techniques for imparting structural integrity and tenability to resultant structures.

In an embodiment, there is provided herein a composite scaffold biomaterial comprising:

- two or more scaffold biomaterial subunits, each comprising a decellularized plant or fungal tissue from which cellular materials and nucleic acids of the tissue are removed, the decellularized plant or fungal tissue comprising a 3-dimensional porous structure;
- the two or more scaffold biomaterial subunits being assembled into the composite scaffold biomaterial and held together via gel casting using a hydrogel glue; via complementary/interlocking geometry of the two or more scaffold biomaterial subunits; via guided assembly based biolithography (GAB); via chemical cross-linking; or any combinations thereof.

In another embodiment of the composite scaffold biomaterial, the two or more scaffold biomaterial subunits may be assembled into the composite scaffold biomaterial and held together via gel casting using a hydrogel glue.

In another embodiment of any of the above composite scaffold biomaterial or biomaterials, the hydrogel glue may comprise gelatin, collagen, agarose, hyaluronic acid, alginate, fibrin, fibronectin, agar, PEG, PVA, or any combinations thereof.

In yet another embodiment of any of the above composite scaffold biomaterial or biomaterials, the two or more scaffold biomaterial subunits may act as a scaffold for the hydrogel glue to form around.

In still another embodiment of any of the above composite scaffold biomaterial or biomaterials, at least a portion of the two or more scaffold biomaterial subunits may be coated with the hydrogel glue.

In another embodiment of any of the above composite scaffold biomaterial or biomaterials, the hydrogel glue may be cured or hardened by a temperature change, cross-linking, or a combination thereof.

In yet another embodiment of any of the above composite scaffold biomaterial or biomaterials, the hydrogel glue may comprise gelatin, which may be cross-linked with glutaraldehyde and sodium borohydride reduction.

In still another embodiment of any of the above composite scaffold biomaterial or biomaterials, the hydrogel glue may further comprise one or more agents such as a therapeutic drug, a signalling molecule, a growth factor, a metabolite, an ECM protein or component, or any combinations thereof.

In another embodiment of any of the above composite scaffold biomaterial or biomaterials, the two or more scaffold biomaterial subunits may be assembled into the composite scaffold biomaterial and held together via complementary interlocking geometry of the two or more scaffold biomaterial subunits.

In yet another embodiment of any of the above composite scaffold biomaterial or biomaterials, the complementary interlocking geometry of the two or more scaffold biomaterial subunits may comprise a peg-and-hole friction-fit interlocking geometry.

In still another embodiment of any of the above composite scaffold biomaterial or biomaterials, at least one of the scaffold biomaterial subunits may comprise or may be seeded with a first cell type. In another embodiment of any of the above composite scaffold biomaterial or biomaterials, at least one other scaffold biomaterial subunit may comprise or may be seeded with a second cell type. In yet another embodiment of any of the above composite scaffold biomaterial or biomaterials, the first and second cell types may be contact-inhibited, or may not be contact-inhibited. In still another embodiment of any of the above composite scaffold biomaterial or biomaterials, the composite scaffold biomaterial may comprise an interface between adjacent scaffold biomaterial subunits which may mimic a tissue interface, such as a bone-fibroblast tissue interface. In another embodiment of any of the above composite scaffold biomaterial or biomaterials, the scaffold biomaterial may comprise ECM deposition at at least one interface between adjacent scaffold biomaterial subunits.

In still another embodiment of any of the above composite scaffold biomaterial or biomaterials, the scaffold biomaterial may comprise an effective Young's modulus which changes based on direction of applied force.

In yet another embodiment of any of the above composite scaffold biomaterial or biomaterials, two or more of the scaffold biomaterial subunits may be additionally held together via gel casting using a hydrogel glue; via guided assembly based biolithography (GAB); via chemical cross-linking; or any combinations thereof.

In another embodiment of any of the above composite scaffold biomaterial or biomaterials, the two or more scaffold biomaterial subunits may be assembled into the composite scaffold biomaterial and may be held together via guided assembly based biolithography (GAB).

In another embodiment of any of the above composite scaffold biomaterial or biomaterials, the two or more scaffold biomaterial subunits may comprise at least one subunit comprising plant or fungus-derived biomaterial, and at least one subunit comprising a bacterial cellulose.

In yet another embodiment of any of the above composite scaffold biomaterial or biomaterials, the bacterial cellulose may be grown on the plant or fungus-derived biomaterial via guided assembly based biolithography (GAB).

In still another embodiment of any of the above composite scaffold biomaterial or biomaterials, the two or more scaffold biomaterial subunits may be assembled into the composite scaffold biomaterial and may be held together via chemical cross-linking.

In yet another embodiment of any of the above composite scaffold biomaterial or biomaterials, at least a portion of two or more of the scaffold biomaterial subunits may be modified to feature carboxymethyl and/or hydroxyl ethyl cellulose functional groups, which may be cross-linked together by citric acid and heat to hold the composite scaffold biomaterial together.

In another embodiment of any of the above composite scaffold biomaterial or biomaterials, the composite scaffold biomaterial may further comprise one or more agents, such as a therapeutic drug, a signalling molecule, a growth factor, a metabolite, an ECM protein or component, or any combinations thereof.

In yet another embodiment of any of the above composite scaffold biomaterial or biomaterials, the decellularized plant or fungal tissue may be cellulose-based, hemicellulose-based, chitin-based, chitosan-based, pectin-based, lignin-based, lignan-based, or any combinations thereof.

In still another embodiment of any of the above composite scaffold biomaterial or biomaterials, the composite scaffold biomaterial may comprise at least two scaffold biomaterial subunits which may be structurally different from one another. In another embodiment of any of the above composite scaffold biomaterial or biomaterials, the at least two scaffold biomaterial subunits which are structurally different from one another may be derived from different plant or fungal sources, may be derived from different parts of the same plant or fungal source, may be derived from two different species of plant or fungal source, may exhibit different Young's modulus properties, may comprise different cell types, may comprise different hydrogels, or any combinations thereof.

In another embodiment, there is provided herein a hydrogel, such as a cellulose-based hydrogel, comprising:

a cross-linked matrix, such as a cross-linked cellulose matrix; and one or more channels formed in the cross-linked matrix by removal of a temporary space filler from the cross-linked matrix.

In another embodiment of the hydrogel, the cross-linked matrix may be prepared from a decellularized plant or fungal tissue from which cellular materials and nucleic acids of the tissue are removed, the decellularized plant or fungal tissue may comprise a 3-dimensional porous structure.

In another embodiment of any of the above hydrogel or hydrogels, the temporary space filler may comprise a temporary gel, such as an alginate hydrogel.

In still another embodiment of any of the above hydrogel or hydrogels, the matrix may be cross-linked around the temporary space filler, and the temporary space filler may then be removed from the cross-linked matrix, thereby forming the one or more channels.

In another embodiment of any of the above hydrogel or hydrogels, the temporary space filler may be removed by dissolution, heating, change in salt concentration, degradation, or any combination thereof.

In yet another embodiment of any of the above hydrogel or hydrogels, the temporary space filler may be positioned within the matrix to template a network of channels within the cross-linked matrix.

In still another embodiment of any of the above hydrogel or hydrogels, the temporary space filler may be positioned within the matrix by deposition via 3D printing.

In another embodiment of any of the above hydrogel or hydrogels, the hydrogel may further comprise one or more agents, such as a therapeutic drug, a signalling molecule, a growth factor, a metabolite, an ECM protein or component, or any combinations thereof.

In yet another embodiment of any of the above hydrogel or hydrogels, the matrix may be prepared from a decellularized plant or fungal tissue which is cellulose-based, hemicellulose-based, chitin-based, chitosan-based, pectin-based, lignin-based, lignan-based, or any combinations thereof.

In another embodiment of any of the above hydrogel or hydrogels, the cross-linked matrix may comprise at least two structurally different celluloses.

In still another embodiment of any of the above hydrogel or hydrogels, the at least two structurally different celluloses may be derived from different plant or fungal sources, may be derived from different parts of the same plant or fungal source, may be derived from two different species of plant or fungal source, may exhibit different Young's modulus properties, may comprise different cell types, may comprise different hydrogels, or any combinations thereof.

In another embodiment, there is provided herein a scaffold biomaterial comprising:

a decellularized plant or fungal tissue from which cellular materials and nucleic acids of the tissue are removed, the decellularized plant or fungal tissue comprising a 3-dimensional porous structure;

at least a portion of the decellularized plant or fungal tissue being functionalized, complexed, or covalently bonded with one or more agents such as a therapeutic drug, a signalling molecule, a growth factor, a metabolite, an ECM protein or component, a linker for subsequent crosslinking or attachment to any of these agents, or any combinations thereof.

In another embodiment of the above scaffold biomaterial, the decellularized plant or fungal tissue may be modified with a linker, such as a succinyl linker, which may be used for crosslinking or covalent bonding with the one or more agents; or wherein the decellularized plant or fungal tissue may be modified with carboxymethyl and/or hydroxyl ethyl cellulose functional groups, which may be used for covalent bonding with the one or more agents via citric acid and heat-based coupling.

In another embodiment, there is provided herein a use of any of the above composite scaffold biomaterials, hydrogels, or scaffold biomaterials, or any combinations thereof, for tissue repair or regeneration; in an implant; for culturing one or more cell types in vitro or in vivo; for mimicking an in vivo tissue or tissue interface; for bone tissue engineering; for repair or regeneration of bone; for transporting a fluid or liquid; for mimicking a tissue interface; for wound healing; for delivery of an agent such as a therapeutic drug, a signalling molecule, a growth factor, a metabolite, an ECM protein or component, or any combinations thereof; or any combinations thereof.

In another embodiment, there is provided herein a method for tissue repair or regeneration; for providing an implant; for culturing one or more cell types; for mimicking an in vivo tissue or tissue interface; for bone tissue engineering; for repair or regeneration of bone; for transporting a fluid or liquid; for mimicking a tissue interface; for wound healing; for delivery of an agent such as a therapeutic drug, a signalling molecule, a growth factor, a metabolite, an ECM protein or component, or any combinations thereof; or any combinations thereof; in a subject in need thereof, said method comprising:

providing any of the above composite scaffold biomaterials, hydrogels, or scaffold biomaterials, or any combinations thereof; and introducing the composite scaffold biomaterial, the hydrogel, or the scaffold biomaterial, or any combinations thereof, to the subject at a site in need thereof.

In another embodiment, there is provided herein a method for guiding cell alignment comprising:

providing a decellularized scaffold biomaterial comprising one or more channels or grooves;

seeding the deceullarized scaffold biomaterial with cells; and culturing the cells on the deceullarized scaffold biomaterial, thereby aligning the cells along the one or more channels or grooves.

In another embodiment of the above method, the decellularized scaffold biomaterial may comprise a decellularized celery tissue.

In another embodiment of the above method or methods, the cells may comprise muscle cells or precursors thereof. In another embodiment, the cells may comprise myoblasts. In another embodiment, the cells may comprise C2C12 myoblasts.

In yet another embodiment, there is provided herein a method for preparing a hydrogel having one or more channels, such as a cellulose-based hydrogel having one or more channels, said method comprising:

providing a first cross-linkable material or gel, such as a natural or modified cellulose-, chitin-, lignin-, lignan-, hemicellulose-, or pectin-based material or gel;

providing a temporary space filler;

generating a 3-dimensional structure comprising the first cross-linkable material or gel with the temporary space filler distributed therein such that the temporary space filler templates one or more channels in the first cross-linkable material or gel, and cross-linking the first cross-linkable material or gel during or after generating the 3-dimensional structure; and removing the temporary space filler from the 3-dimensional structure to provide the hydrogel having one or more channels.

In another embodiment, there is provided herein a method for producing a scaffold biomaterial, said method comprising:

providing a plant or fungal tissue;

extracting one or more structures from the plant or fungal tissue; and preparing the scaffold biomaterial from the one or more extracted structures.

In another embodiment of the above method, the step of extracting may comprise a liquid-based extraction to isolate the one or more structures from the plant or fungal tissue.

In still another embodiment of any of the above method or methods, the step of extracting may comprise maceration using at least one of treatment with a salt solution; treatment with a base solution; treatment with an acid solution; or treatment with an acid and peroxide solution.

In yet another embodiment of any of the above method or methods, the salt solution may comprise a salt concentration of about 0.5M-3M. As will be understood, salt concentration may be adjusted depending on the particular application of interest. For example, where the structures to be extracted from the plant or fungal tissue comprise vascular bundles or microchannels (see below), then higher salt concentrations (such as, for example, about 1 to about 3M) may be preferable.

In another embodiment of any of the above method or methods, the salt solution may comprise a NaCl solution or a LiCl solution.

In still another embodiment of any of the above method or methods, the base solution may comprise a base concentration of about 0.5M-3M. As will be understood, base concentration may be adjusted depending on the particular application of interest.

In yet another embodiment of any of the above method or methods, the base solution may comprise a NaOH solution.

In another embodiment of any of the above method or methods, the acid and peroxide solution may comprise a ratio of acid to peroxide of about 3:1 to about 1:3, or any ratio value (optionally rounded to the nearest 0.1) therebetween, or any subrange spanning between any two of these ratios. By way of example, in certain embodiments, a ratio of acid to peroxide of about 3:1, 1:1, or 1:3 may be used. By way of example, in certain embodiments, an acid and peroxide solution may comprise acetic acid as acid, and hydrogen peroxide as peroxide, and may be provided with an acid to peroxide ratio of about 3:1 (i.e. 13.05M acetic acid, 2.45M peroxide), 1:1 (i.e. 8.7M acetic acid, 4.9M peroxide), or 1:3 (i.e. 4.35M acetic acid, 7.35M peroxide). As will be understood, acid and peroxide concentration may be adjusted depending on the particular application of interest.

In another embodiment of any of the above method or methods, the acid and peroxide solution may comprise acetic acid and hydrogen peroxide.

In still another embodiment of any of the above method or methods, the acid and peroxide solution may comprise a ratio (by volume) of glacial acetic acid to 30% hydrogen peroxide at 3:1 (containing 13.05M acetic acid and 2.45M hydrogen peroxide) to 1:3 (containing 4.35M acetic acid and 7.35M hydrogen peroxide).

In yet another embodiment of any of the above method or methods, the step of extracting may comprise heating the plant or fungal tissue in the salt solution, the base solution, or the acid and peroxide solution.

In another embodiment of any of the above method or methods, the step of extracting may further comprise mechanically agitating, for example stirring, the plant or fungal tissue in the salt solution, the base solution, or the acid and peroxide solution.

In still another embodiment of any of the above method or methods, the one or more structures from the plant or fungal tissue may comprise a 3-dimensional structure, such as one or more structures derived from hypanthium or pulp (i.e. fleshy material) structures, microchannels such as xylem and/or phloem (e.g. microchannel-type structures of vascular plants/materials), or any combinations thereof, or other such structures.

In yet another embodiment of any of the above method or methods, the hypanthium or pulp structures may comprise an extended 3D structure (which may be comprised of any one or more of cellulose, hemicellulose, pectin, lignin, or the like; typically, the extended 3D structure may comprise a lignocellulosic structure), single structural cells or groups of structural cells derived from the extended 3D structure, or any combinations thereof. In certain embodiments, the extended 3D structure may be cellulose-based.

In another embodiment of any of the above method or methods, the step of extracting may further comprise performing centrifugation.

In still another embodiment of any of the above method or methods, the centrifugation may separate extended 3D structures and/or microchannels such as xylem and/or phloem from single structural cells or groups of structural cells derived from the extended 3D structures.

In yet another embodiment of any of the above method or methods, the step of extracting may further comprise performing centrifugation, which separates extended 3D structures from single structural cells or groups of structural cells derived from the extended 3D structures.

In another embodiment of any of the above method or methods, centrifugation may produce an upper band or pellet comprising the single structural cells or groups of structural cells derived from the extended 3D structures.

In still another embodiment of any of the above method or methods, the one or more structures from the plant or fungal tissue may comprise the single structural cells or groups of structural cells derived from the extended 3D structures localized to the upper band or pellet.

In another embodiment of any of the above method or methods, the step of extracting may further comprise washing the one or more structures from the plant of fungal tissue.

In still another embodiment of any of the above method or methods, the step of preparing the scaffold biomaterial from the one or more extracted structures may comprise mixing, agitating, or physically manipulating the extracted structures to excise residual undesirable plant tissue materials; washing the one or more extracted structures from the plant or fungal tissue; or both.

In yet another embodiment of any of the above method or methods, the plant or fungal tissue may comprise decellularized plant or fungal tissue from which cellular materials and nucleic acids of the tissue are removed.

In another embodiment of any of the above method or methods, the method may further comprise a step of decellularizing the plant or fungal tissue prior to the step of extracting. In another embodiment, the conditions of the extracting step may be selected such that decellularization, or partial decellularization, occurs during the extracting step.

In still another embodiment of any of the above method or methods, the method may further comprise a step of decellularizing the one or more structures extracted from the plant of fungal tissue.

In yet another embodiment of any of the above method or methods, the method may further comprise a step of decellularizing the plant or fungal tissue, or decellularizing the one or more structures from the plant or fungal tissue, or both.

In another embodiment of any of the above method or methods, the step of preparing the scaffold biomaterial from the one or more extracted structures may comprise decellularizing the one or more extracted structures.

In certain embodiments of any of the above method or methods, a step of grinding may be performed on the plant or fungal tissue prior to extraction, and/or on the one or more extracted structures following extraction.

In still another embodiment of any of the above method or methods, the step of preparing the scaffold biomaterial from the one or more extracted structures may comprise grinding the one or more extracted structures.

In certain embodiments, the material to be ground may be initially freeze-dried to remove moisture, so as to prevent build-up due to moisture during grinding, particularly for fine grinding to produce small particles.

In yet another embodiment of any of the above method or methods, the step of preparing the scaffold biomaterial from the one or more extracted structures may comprise incorporating the one or more extracted structures into a matrix; or gluing or adhering extracted structures and/or scaffold biomaterials together; drying or lyophilizing the one or more extracted structures or scaffold biomaterials; seeding or culturing cells, such as animal cells, on the extracted structures and/or scaffold biomaterials; associating two or more extracted structures and/or scaffold biomaterials via layering, stacking, or other complementary/interlocking geometry; or any combinations thereof.

In still another embodiment of any of the above method or methods, the matrix may comprise a hydrogel, forming a composite hydrogel.

In yet another embodiment of any of the above method or methods, the matrix or glue comprises an alginate matrix.

In another embodiment, there is provided herein a scaffold biomaterial produced by any of the above method or methods.

In another embodiment, there is provided herein a scaffold biomaterial comprising one or more structures extracted from plant or fungal tissue.

In still another embodiment of the above scaffold biomaterial, the one or more structures are extracted from the plant or fungal tissue by a liquid-based extraction.

In yet another embodiment of any of the above scaffold biomaterial or scaffold biomaterials, the one or more structures may be extracted from the plant or fungal tissue by treatment with a salt solution; treatment with a base solution; treatment with an acid solution; or treatment with an acid and peroxide solution.

In yet another embodiment of any of the above scaffold biomaterial or scaffold biomaterials, the one or more structures from the plant or fungal tissue may comprise a 3-dimensional structure, such as one or more structures derived from hypanthium or pulp structures, microchannels such as xylem and/or phloem, or any combinations thereof.

In another embodiment of any of the above scaffold biomaterial or scaffold biomaterials, the hypanthium or pulp structures may comprise an extended 3D structure (which may be comprised of any one or more of cellulose, hemicellulose, pectin, lignin, or the like; typically, the extended 3D structure may comprise a lignocellulosic structure), single structural cells or groups of structural cells derived from the extended 3D structure, or any combinations thereof. In certain embodiments, the extended 3D structure may be cellulose-based.

In still another embodiment of any of the above scaffold biomaterial or scaffold biomaterials, the one or more structures may comprise single structural cells or groups of structural cells derived from the extended 3D structures by centrifugation separation.

In yet another embodiment of any of the above scaffold biomaterial or scaffold biomaterials, the scaffold biomaterial may be a decellularized scaffold biomaterial lacking cellular materials and nucleic acids of the plant or fungal tissue.

In another embodiment of any of the above scaffold biomaterial or scaffold biomaterials, the one or more structures may have been ground to reduce particle size.

In still another embodiment of any of the above scaffold biomaterial or scaffold biomaterials, the scaffold biomaterial may comprise a matrix into which the one or more structures are incorporated; a product formed by gluing or adhering extracted structures and/or scaffold biomaterials together; a product formed by drying or lyophilizing the one or more extracted structures or scaffold biomaterials; a product formed by seeding or culturing cells, such as animal cells, on the extracted structures and/or scaffold biomaterials; a product formed by associating two or more extracted structures and/or scaffold biomaterials via layering, stacking, or other complementary/interlocking geometry; or any combinations thereof.

In yet another embodiment of any of the above scaffold biomaterial or scaffold biomaterials, the matrix may comprise a hydrogel.

In another embodiment of any of the above scaffold biomaterial or scaffold biomaterials, the matrix or glue may comprise alginate.

In another embodiment, there is provided herein a food product comprising a scaffold biomaterial, the scaffold biomaterial comprising one or more 3-dimensional structures derived or extracted from a plant or fungal tissue.

In another embodiment of the above food product, the one or more 3-dimensional structures may comprise one or more structures derived from hypanthium or pulp structures, microchannels, or any combinations thereof.

In still another embodiment of any of the above food product or food products, the microchannels may comprise xylem and/or phloem.

In yet another embodiment of any of the above food product or food products, the one or more structures derived from hypanthium or pulp structures may comprise an extended 3D structure (which may be comprised of any one or more of cellulose, hemicellulose, pectin, lignin, or the like; typically, the extended 3D structure may comprise a lignocellulosic structure), single structural cells or groups of structural cells derived from the extended 3D structure, or any combinations thereof. In certain embodiments, the extended 3D structure may be cellulose-based.

In another embodiment of any of the above food product or food products, the scaffold biomaterial may be decellularized, the one or more 3-dimensional structures lacking cellular materials and nucleic acids of the plant or fungal tissue.

In still another embodiment of any of the above food product or food products, the scaffold biomaterial may comprise any of the scaffold biomaterial or scaffold biomaterials as described above.

In yet another embodiment of any of the above food product or food products, the scaffold biomaterial may comprise a matrix into which the one or more 3-dimensional structures are incorporated; a product formed by gluing or adhering the one or more 3-dimensional structures and/or scaffold biomaterials together; a product formed by drying or lyophilizing the one or more 3-dimensional structures or scaffold biomaterials; a product formed by seeding or culturing cells, such as animal cells, on the 3-dimensional structures and/or scaffold biomaterials; a product formed by associating two or more extracted structures and/or scaffold biomaterials via layering, stacking, or other complementary/interlocking geometry; or any combinations thereof.

In another embodiment of any of the above food product or food products, the scaffold biomaterial may comprise a matrix into which the one or more 3-dimensional structures are incorporated; a product formed by gluing or adhering the one or more 3-dimensional structures and/or scaffold biomaterials together; or any combination thereof.

In still another embodiment of any of the above food product or food products, the matrix or glue may comprise alginate.

In yet another embodiment of any of the above food product or food products, the scaffold biomaterial may comprise two or more different 3-dimensional structures derived or extracted from the same, or different, plant or fungal tissues.

In another embodiment of any of the above food product or food products, the food product may comprise two or more different scaffold biomaterials having different structural or physical properties.

In still another embodiment of any of the above food product or food products, the two or more different 3-dimensional structures, and/or the two or more different scaffold biomaterials, may be selected so as to provide a target stiffness, mouth-feel, and/or texture to the food product.

In yet another embodiment of any of the above food product or food products, one or more cells are seeded or cultured on the scaffold biomaterial and/or 3-dimensional structures.

In another embodiment of any of the above food product or food products, the one or more cells comprise animal cells.

In still another embodiment of any of the above food product or food products, the animal cells may comprise cells of a livestock animal, fish, or insect, or other animal of interest.

In yet another embodiment of any of the above food product or food products, the animal cells may comprise bovine, porcine, fish, elk, chicken, turkey, or avian cells, for example.

In another embodiment of any of the above food product or food products, the one or more cells may comprise muscle cells, fat cells, connective tissue cells (i.e. fibroblasts), cartilage, bone, epithelial, or endothelial cells, or any combinations thereof.

In still another embodiment of any of the above food product or food products, the food product may comprise at least a first layer of scaffold biomaterial and a second layer of scaffold biomaterial, one of the layers being seeded with muscle cells and the other of the layers being seeded with fat cells.

In yet another embodiment of any of the above food product or food products, the one or more cells may be aligned along one or more channels or grooves of the scaffold biomaterial and/or of the 3-dimensional structures.

In another embodiment of any of the above food product or food products, the one or more cells may comprise muscle cells.

In still another embodiment of any of the above food product or food products, the food product may comprise one or more 3-dimensional structures derived from hypanthium or pulp structures, and one or more microchannel structures.

In yet another embodiment of any of the above food product or food products, the 3-dimensional structures derived from hypanthium or pulp structures comprise an extended 3D structure (which may be comprised of any one or more of cellulose, hemicellulose, pectin, lignin, or the like; typically, the extended 3D structure may comprise a lignocellulosic structure), single structural cells or groups of structural cells derived from the extended 3D structure, or any combinations thereof. In certain embodiments, the extended 3D structure may be cellulose-based.

In another embodiment of any of the above food product or food products, the microchannel structures may comprise xylem and/or phloem.

In still another embodiment of any of the above food product or food products, the xylem and/or phloem in vascular bundles.

In yet another embodiment of any of the above food product or food products, the scaffold biomaterial may comprise any of the composite scaffold biomaterials as described herein.

In another embodiment, there is provided herein a method for preparing a food product, the method comprising:

producing a scaffold biomaterial by:

providing a plant or fungal tissue;

deriving or extracting one or more 3-dimensional structures from the plant of fungal tissue; and preparing the scaffold biomaterial from the one or more derived or extracted 3-dimensional structures; and preparing the food product from the scaffold biomaterial.

In another embodiment of the above method, the step of producing the scaffold biomaterial may comprise performing any of the method or methods described hereinabove.

In still another embodiment of any of the above method or methods, the step of preparing the food product from the scaffold biomaterial may comprise any one or more of incorporating the one or more derived or extracted 3-dimensional structures into a matrix; or gluing or adhering derived or extracted 3-dimensional structures and/or scaffold biomaterials together; drying or lyophilizing the one or more derived or extracted 3-dimensional structures or scaffold biomaterials; seeding or culturing cells on the derived or extracted 3-dimensional structures and/or scaffold biomaterials; associating two or more derived or extracted 3-dimensional structures and/or scaffold biomaterials via layering, stacking, or other complementary/interlocking geometry; or any combinations thereof.

In yet another embodiment of any of the above method or methods, the step of preparing the food product from the scaffold biomaterial may comprise seeding or culturing cells on the derived or extracted 3-dimensional structures and/or scaffold biomaterials.

In another embodiment of any of the above method or methods, the one or more cells may comprise animal cells.

In still another embodiment of any of the above method or methods, the animal cells may comprise cells of a livestock animal, fish, or insect.

In yet another embodiment of any of the above method or methods, the animal cells may comprise bovine, porcine, fish, elk, chicken, turkey, or avian cells.

In another embodiment of any of the above method or methods, the one or more cells may comprise muscle cells, fat cells, connective tissue cells (for example, fibroblasts), cartilage, bone, epithelial, or endothelial cells, or any combinations thereof.

In still another embodiment of any of the above method or methods, the method may comprise producing at least a first layer of scaffold biomaterial and a second layer of scaffold biomaterial, one of the layers being seeded with muscle cells and the other of the layers being seeded with fat cells.

In yet another embodiment of any of the above method or methods, the one or more cells may be aligned along one or more channels or grooves of the scaffold biomaterial and/or of the 3-dimensional structures.

In another embodiment of any of the above method or methods, the one or more cells may comprise muscle cells.

In still another embodiment of any of the above method or methods, the method may comprise producing two or more different scaffold biomaterials having different structural or physical properties; producing one or more scaffold biomaterials comprising two or more different 3-dimensional structures derived or extracted from the same, or different, plant or fungal tissues; or any combinations thereof.

In yet another embodiment of any of the above method or methods, the two or more different 3-dimensional structures, and/or the two or more different scaffold biomaterials, may be selected so as to provide a target stiffness, mouth-feel, and/or texture to the food product.

BRIEF DESCRIPTION OF DRAWINGS

These and other features will become further understood with regard to the following description and accompanying drawings, wherein:

FIG. 4 shows (A) 6×2 mm longitudinal scaffold; and (B) cross section of vascular bundle. (Blue) Ground tissue and phloem, (Red) Xylem;

FIG. 16 shows stress shielding composites. Decellularized apple and carrot composites compress in the series and parallel configurations lead to different Young's moduli;

DETAILED DESCRIPTION

Figure 1:
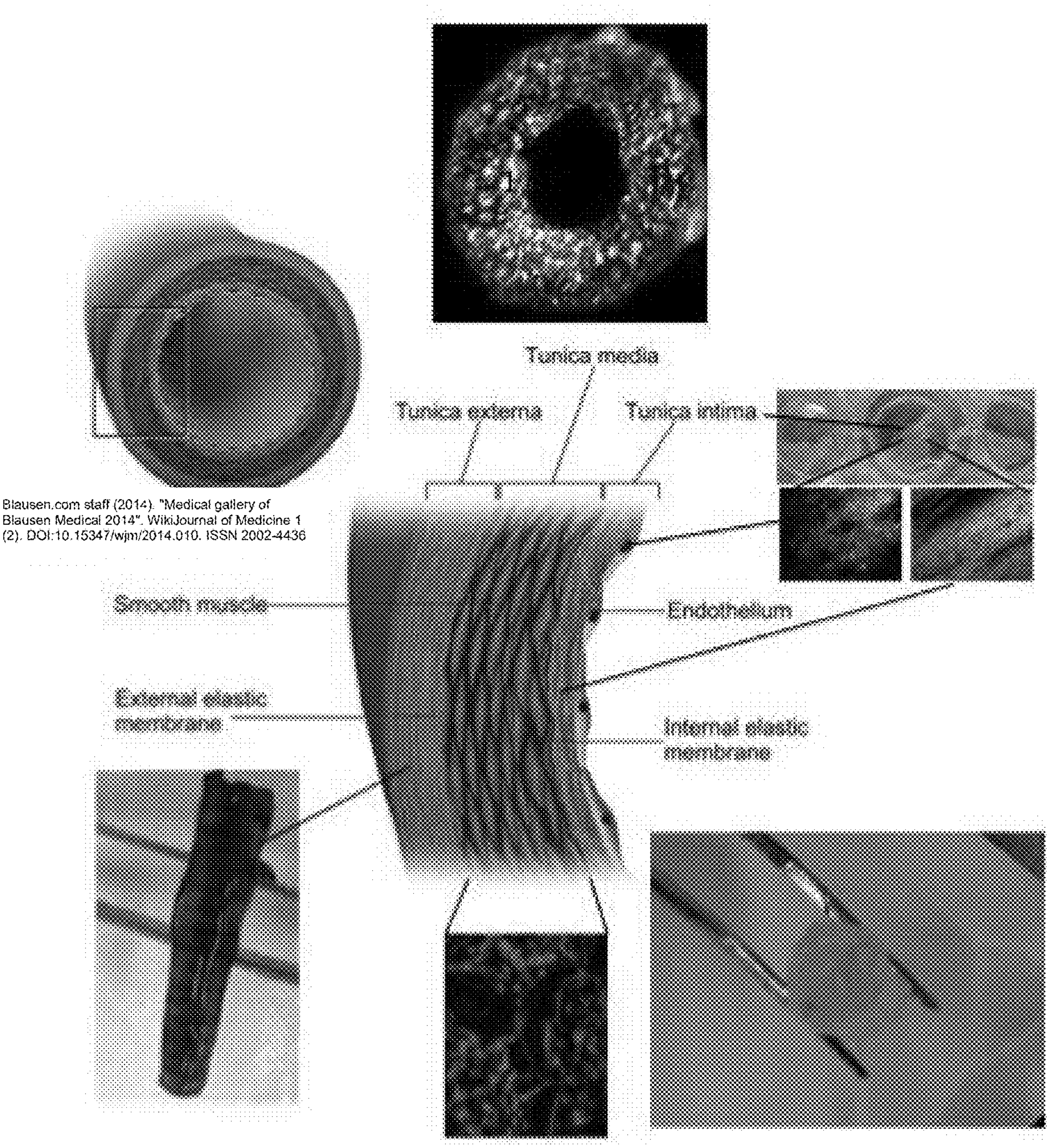
FIG. 1 shows an example of a contemplated application of composite materials as described herein, wherein the composite materials may be generated in the form of blood vessels. Blood vessels are complex structures with different layers of tissues (upper left and central images). In the examples provided hereinbelow, ring structures have been prepared (also see top and bottom centre images) from apple derived cellulose that may be stacked and coated with a hydrogel such as 1.5% agarose to produce a vessel (bottom right and left images). This vessel may be wrapped with different layers or membranes containing different cell types. A sample material for the membrane may be decellularized orange pith membranes (see upper right image), for example. Combining multiple elements may be used to more closely recreate complex structures such as blood vessels, which have different tissues and cell types organized radially.

Described herein are composite scaffold biomaterials including two or more scaffold biomaterial subunits, each including a decellularized plant or fungal tissue from which cellular materials and nucleic acids of the tissue are removed, the decellularized plant or fungal tissue having a 3-dimensional porous structure, the two or more scaffold biomaterial subunits being assembled into the composite scaffold biomaterial and held or associated together, for example via gel casting using a hydrogel glue; via complementary interlocking geometry of the two or more scaffold biomaterial subunits; via guided assembly based biolithography (GAB); via chemical cross-linking; or any combinations thereof. Methods for producing such scaffold biomaterials, as well as methods and uses thereof, are also provided. Scaffold biomaterials may be produced for a variety of different applications, including but not limited to medical applications and/or applications in the food industry as plant-derived meat alternatives. It will be appreciated that embodiments and examples are provided for illustrative purposes intended for those skilled in the art, and are not meant to be limiting in any way.

In an embodiment, there is provided herein a composite scaffold biomaterial comprising: two or more scaffold biomaterial subunits, each comprising a decellularized plant or fungal tissue from which cellular materials and nucleic acids of the tissue are removed, the decellularized plant or fungal tissue comprising a 3-dimensional porous structure;

the two or more scaffold biomaterial subunits being assembled into the composite scaffold biomaterial and held together via gel casting using a hydrogel glue; via complementary interlocking geometry of the two or more scaffold biomaterial subunits; via guided assembly based biolithography (GAB); via chemical cross-linking; or any combinations thereof.

In certain embodiments, the biomaterials described herein may be derived from cell wall architectures and/or vascular structures found in the plant and fungus kingdoms to create 3D scaffolds which may promote cell infiltration, cell growth, bone tissue repair, and/or bone reconstruction, etc. As will be understood, biomaterials as described herein may be produced from any suitable part of plant or fungal organisms. Biomaterials may comprise, for example, substances such as cellulose, chitin, lignin, lignan, hemicellulose, pectin, and/or any other suitable biochemicals/biopolymers which are naturally found in these organisms.

As will be understood, unless otherwise indicated, the meaning/definition of plant and fungi kingdoms used herein is based on the Cavalier-Smith classification (1998).

In certain embodiments, the plant or fungal tissue may comprise generally any suitable plant or fungal tissue or part containing a suitable scaffold structure appropriate for the particular application.

In certain embodiments of the scaffold biomaterial or biomaterials above, the plant or fungal tissue may comprise an apple hypanthium (*Malus pumila*) tissue, a fern (Monilophytes) tissue, a turnip (*Brassica rapa*) root tissue, a gingko branch tissue, a horsetail (equisetum) tissue, a hermocallis hybrid leaf tissue, a kale (*Brassica oleracea*) stem tissue, a conifers Douglas Fir (*Pseudotsuga menziesii*) tissue, a cactus fruit (pitaya) flesh tissue, a Maculata Vinca tissue, an Aquatic Lotus (*Nelumbo nucifera*) tissue, a Tulip (*Tulipa gesneriana*) petal tissue, a Plantain (*Musa paradisiaca*) tissue, a broccoli (*Brassica oleracea*) stem tissue, a maple leaf (*Acer psuedoplatanus*) stem tissue, a beet (*Beta vulgaris*) primary root tissue, a green onion (*Allium cepa*) tissue, a orchid (Orchidaceae) tissue, turnip (*Brassica rapa*) stem tissue, a leek (*Allium ampeloprasum*) tissue, a maple (*Acer*) tree branch tissue, a celery (*Apium graveolens*) tissue, a green onion (*Allium cepa*) stem tissue, a pine tissue, an aloe vera tissue, a watermelon (*Citrullus lanatus* var. *lanatus*) tissue, a Creeping Jenny (*Lysimachia nummularia*) tissue, a cactae tissue, a Lychnis Alpina tissue, rhubarb (*Rheum rhabarbarum*) tissue, a pumpkin flesh (*Cucurbita pepo*) tissue, a Dracena (Asparagaceae) stem tissue, a Spiderwort (*Tradescantia virginiana*) stem tissue, an *Asparagus* (*Asparagus officinalis*) stem tissue, a mushroom (Fungi) tissue, a fennel (*Foeniculum vulgare*) tissue, a rose (Rosa) tissue, a carrot (*Daucus carota*) tissue, or a pear (Pomaceous) tissue. Additional examples of plant and fungal tissues are described in Example 18 of WO2017/136950, entitled "Decellularised Cell Wall Structures from Plants and Fungus and Use Thereof as Scaffold Materials", herein incorporated by reference in its entirety.

In certain embodiments, the decellularized plant or fungal tissue is cellulose-based, chitin-based, chitosan-based, lignin-based, lignan-based, hemicellulose-based, or pectin-based, or any combination thereof. In certain embodiments, the plant or fungal tissue may comprise a tissue from apple hypanthium (*Malus pumila*) tissue, a fern (Monilophytes) tissue, a turnip (*Brassica rapa*) root tissue, a gingko branch tissue, a horsetail (equisetum) tissue, a hermocallis hybrid leaf tissue, a kale (*Brassica oleracea*) stem tissue, a conifers Douglas Fir (*Pseudotsuga menziesii*) tissue, a cactus fruit (pitaya) flesh tissue, a Maculata Vinca tissue, an Aquatic Lotus (*Nelumbo nucifera*) tissue, a Tulip (*Tulipa gesneriana*) petal tissue, a Plantain (*Musa paradisiaca*) tissue, a broccoli (*Brassica oleracea*) stem tissue, a maple leaf (*Acer psuedoplatanus*) stem tissue, a beet (*Beta vulgaris*) primary root tissue, a green onion (*Allium cepa*) tissue, a orchid (Orchidaceae) tissue, turnip (*Brassica rapa*) stem tissue, a leek (*Allium ampeloprasum*) tissue, a maple (*Acer*) tree branch tissue, a celery (*Apium graveolens*) tissue, a green onion (*Allium cepa*) stem tissue, a pine tissue, an aloe vera tissue, a watermelon (*Citrullus lanatus* var. *lanatus*) tissue, a Creeping Jenny (*Lysimachia nummularia*) tissue, a cactae tissue, a Lychnis Alpina tissue, a rhubarb (*Rheum rhabarbarum*) tissue, a pumpkin flesh (*Cucurbita pepo*) tissue, a Dracena (Asparagaceae) stem tissue, a Spiderwort (*Tradescantia virginiana*) stem tissue, an *Asparagus* (*Asparagus officinalis*) stem tissue, a mushroom (Fungi) tissue, a fennel (*Foeniculum vulgare*) tissue, a rose (Rosa) tissue, a carrot (*Daucus carota*) tissue, or a pear (Pomaceous) tissue, or a genetically altered tissue produced via direct genome modification or through selective breeding, or any combinations thereof.

As will also be understood, cellular materials and nucleic acids of the plant or fungal tissue may include intracellular contents such as cellular organelles (e.g. chloroplasts, mitochondria), cellular nuclei, cellular nucleic acids, and/or cellular proteins. These may be substantially removed, partially removed, or fully removed from the plant or fungal tissue, and/or from the scaffold biomaterial. It will recognized that trace amounts of such components may still be present in the decellularised plant or fungal tissues described herein. As will also be understood, references to decellularized plant or fungal tissue herein are intended to reflect that such cellular materials found in the plant or fungal source of the tissues have been substantially removed—this does not preclude the possibility that the decellularized plant or fungal tissue may in certain embodiments contain or comprise subsequently introduced, or reintroduced, cells, cellular materials, and/or nucleic acids of generally any kind, such as animal or human cells, such as bone or bone progenitor cells/tissues.

Various methods may be used for producing scaffold biomaterials or scaffold biomaterial subunits as described herein. By way of example, in certain embodiments of the scaffold biomaterials and/or subunits above, the decellularised plant or fungal tissue may comprise plant or fungal tissue(s) which have been decellularised by thermal shock, treatment with detergent (e.g. SDS, Triton X, EDA, alkaline treatment, acid, ionic detergent, non-ionic detergents, and zwitterionic detergents), osmotic shock, lyophilisation, physical lysing (e.g. hydrostatic pressure), electrical disruption (e.g. non thermal irreversible electroporation), or enzymatic digestion, or any combination thereof. In certain embodiments, biomaterials as described herein may be obtained from plants and/or fungi by employing decellularization processes which may comprise any of several approaches (either individually or in combination) including, but not limited to, thermal shock (for example, rapid freeze thaw), chemical treatment (for example, detergents), osmotic shock (for example, distilled water), lyophilisation, physical lysing (for example, pressure treatment), electrical disruption and/or enzymatic digestion.

In certain embodiments, the decellularised plant or fungal tissue may comprise plant or fungal tissue which has been decellularised by treatment with a detergent or surfactant. Examples of detergents may include, but are not limited to sodium dodecyl sulphate (SDS), Triton X, EDA, alkyline treatment, acid, ionic detergent, non-ionic detergents, and zwitterionic detergents.

In still further embodiments, the decellularised plant or fungal tissue may comprise plant or fungal tissue which has been decellularised by treatment with SDS. In still another embodiment, residual SDS may be removed from the plant or fungal tissue by washing with an aqueous divalent salt solution. The aqueous divalent salt solution may be used to precipitate/crash a salt residue containing SDS micelles out of the solution/scaffold, and a $dH_2O$, acetic acid or dimethylsulfoxide (DMSO) treatment, or sonication, may have been used to remove the salt residue or SDS micelles. In certain embodiments, the divalent salt of the aqueous divalent salt solution may comprise, for example, $MgCl_2$ or $CaCl_2$.

In another embodiment, the plant or fungal tissue may be decellularised by treatment with an SDS solution of between 0.01 to 10%, for example about 0.1% to about 1%, or, for example, about 0.1% SDS or about 1% SDS, in a solvent such as water, ethanol, or another suitable organic solvent, and the residual SDS may have been removed using an aqueous $CaCl_2$ solution at a concentration of about 100 mM followed by incubation in $dH_2O$. In certain embodiments, the SDS solution may be at a higher concentration than 0.1%, which may facilitate decellularisation, and may be accompanied by increased washing to remove residual SDS. In particular embodiments, the plant or fungal tissue may be decellularised by treatment with an SDS solution of about 0.1% SDS in water, and the residual SDS may have been removed using an aqueous $CaCl_2$ solution at a concentration of about 100 mM followed by incubation in $dH_2O$.

Further examples of decellularization protocols which may be adapted for producing decellularized plant or fungal tissue for scaffold biomaterials as described herein may be found in WI2017/136950, entitled "Decellularised Cell Wall Structures from Plants and Fungus and Use Thereof as Scaffold Materials", herein incorporated by reference in its entirety.

In certain embodiments, the scaffold biomaterials as described herein may comprise decellularized plant or fungal tissue comprising a pore size of about 100 to about 200 μm, or of about 150 to about 200 μm. In certain embodiments, the scaffold biomaterial may comprise a Young's moduli between about 20 to about 200 kPa. In certain embodiments, the decellularized plant or fungal tissue may comprise decellularized apple, such as decellularized apple hypanthium tissue.

In certain embodiments of the scaffold biomaterials as described herein, the scaffold biomaterials may further comprise living cells, in particular non-native cells, on and/or within the decellularized plant or fungal tissue. In certain embodiments, the living cells may be animal cells. In certain embodiments, the living cells may be mammalian cells. In certain embodiments, the living cells may be human cells.

In certain embodiments, the two or more scaffold biomaterial subunits may be assembled into the composite scaffold biomaterial and held together via gel casting using a hydrogel glue.

As will be understood, gel casting may include any suitable gel casting process known to the person of skill in the art having regard to the teachings here. By way of example, in certain embodiments, gel casting may comprise a suitable process of surrounding all or a portion of a material with a gel. A variety of techniques may be used to cast the gel. By way of example, in certain embodiments, the gel may be cast be immersion, pipetting, coating, or other such techniques.

In certain embodiments, a hydrogel glue may comprise any suitable hydrogel glue, or mimic or functional equivalent thereof. In certain embodiments, a hydrogel glue may comprise a glue based on one or more macromolecule polymers that may be cross-linked and may hold water. In certain embodiments, rather than cross-linking, polymers may be entangled, or polymer melts may be used, or any combinations thereof. In certain embodiments, colloids may be used. Some examples of hydrogel glues may include gelatin, collagen, hyaluronic acid, agarose, fibronectin, or other such glues.

In certain embodiments, the hydrogel glue may comprise gelatin, collagen, agarose, hyaluronic acid, alginate, fibrin, fibronectin, agar, PEG, PVA, or any combinations thereof. In certain embodiments, the two or more scaffold biomaterial subunits may act as a scaffold for the hydrogel glue to form around. In certain embodiments, at least a portion of the two or more scaffold biomaterial subunits may be coated with the hydrogel glue. In certain embodiments, the hydrogel glue may be cured or hardened by a temperature change, cross-linking, or a combination thereof. In certain embodiments, the hydrogel glue may comprise gelatin, which is cross-linked with glutaraldehyde and sodium borohydride reduction. In certain embodiments, the hydrogel glue may further comprise one or more agents such as a therapeutic drug, a signalling molecule, a growth factor, a metabolite, an ECM protein or component, or any combinations thereof.

In certain embodiments, the two or more scaffold biomaterial subunits may be assembled into the composite scaffold biomaterial and held together via complementary interlocking geometry of the two or more scaffold biomaterial subunits.

In certain embodiments, a complementary interlocking geometry may comprise any suitable geometry or shape or structural feature of the scaffold biomaterial subunits allowing the scaffold biomaterial subunits to be fitted together. Typically, each of the scaffold biomaterial subunits may comprise one or more interlocking geometry features which may be complementary to corresponding interlocking geometry feature(s) on one or more adjacent scaffold biomaterial subunits which are to be assembled together. In certain embodiments, the interlocking geometry may comprise a friction-fit type complementarity. In certain embodiments, the complementary interlocking geometry may comprise male and female corresponding interlocking geometries on adjacent scaffold biomaterial subunits. In certain embodiments, the complementary interlocking geometry may comprise a peg-and-hole (i.e. Lego-style) type structure such may allow for two adjacent scaffold biomaterial subunits to be pressed or pushed together, resulting in a friction fit between the peg and hole features of the scaffold biomaterial subunits. A variety of other complementary interlocking geometry features are also contemplated, such as a key-hole type design, a latch-type design, a stud-type design, a taper-fit type design (wherein the fit of adjacent subunits may be modified by adjusting or modifying the taper to provide loose, tight, or intermediate fits therebetween, to suit a particular application), or a clip-type design, for example. In certain embodiments, a complementary/interlocking geometry may comprise any suitable geometry or shape allowing scaffold biomaterial subunits to be positioned against each other such that the subunits contact one another over a large surface area, and surface textures of the subunits, surface features of the subunits, or any combinations thereof, at the contact/interface region may prevent slippage, for example.

In certain embodiments, it is contemplated that complementary interlocking geometries may be designed, adjusted, or modulated to provide desired mechanical results. For example, in certain embodiments, a composite biomaterial intended to act as a vessel for drug delivery may be designed to be relatively loosely interlocked compared to a composite biomaterial intended to act as a large scaffold.

In certain embodiments, the complementary interlocking geometry of the two or more scaffold biomaterial subunits comprises a peg-and-hole, or other friction-fit type, interlocking geometry.

In certain embodiments, at least one of the scaffold biomaterial subunits may comprise or may be seeded with a first cell type. In certain further embodiments, at least one other scaffold biomaterial subunit may comprise or may be seeded with a second cell type. In certain embodiments, the first and second cell types may be contact-inhibited, or may not be contact-inhibited. In certain embodiments, the composite scaffold biomaterial may comprise an interface between adjacent scaffold biomaterial subunits which may mimic a tissue interface, such as a bone-fibroblast tissue interface. In certain embodiments, the first cell type, the second cell type, or both, may be animal cells, such as mammalian cells or human cells. In certain embodiments, the scaffold biomaterials may comprise ECM deposition at at least one interface between adjacent scaffold biomaterial subunits. In certain embodiments, the scaffold biomaterial may comprise an effective Young's modulus which may change based on the direction of applied force. In certain embodiments, two or more of the scaffold biomaterial subunits may be additionally held together via gel casting using a hydrogel glue; via guided assembly based biolithography (GAB); via chemical cross-linking; or any combinations thereof.

In certain embodiments, the two or more scaffold biomaterial subunits may be assembled into the composite scaffold biomaterial and held together via guided assembly based biolithography (GAB).

As will be understood, guided assembly based biolithography (GAB) may include techniques using a template to transfer topographies to a biomaterial. In certain embodiments, the template may serve as a guide for bacterial cellulose to grow onto a scaffold biomaterial, for example. In certain embodiments, a composite biomaterial comprising plant- and bacterial-derived cellulose may be preparing having customizable topographies and/or densities, for example.

Certain bacteria produce and excrete cellulose. The crystal structure of the produced cellulose is different from that of plant-derived cellulose, and the amount and/or arrangement of amorphous and crystalline regions may differ which may notably affect material properties. As such, the physical, mechanical, and/or chemical properties of plant and bacterial cellulose may be different. The person of skill in the art having regard to the teachings herein will be aware of a variety of cellulose-producing bacteria, and the types of cellulose which may be obtained therefrom.

In certain embodiments, the two or more scaffold biomaterial subunits comprise at least one subunit comprising plant or fungus-derived biomaterial, and at least one subunit comprising a bacterial cellulose.

In certain embodiments, the bacterial cellulose may be grown on the plant or fungus-derived biomaterial via guided assembly based biolithography (GAB).

In certain embodiments, the two or more scaffold biomaterial subunits may be assembled into the composite scaffold biomaterial and held together via chemical cross-linking.

In certain embodiments, chemical cross-linking may include covalent bonding of two separate cellulose chains. The crosslinking sites may depend on the availability and/or location of functional groups such as hydroxyl groups, and on the density of the chains. In an embodiment, cellulose chains may be modified to add a linker such as succinic acid, and crosslinking may be conducted to the free moiety. In certain embodiments, such modifications may be used to introduce crosslinkable end groups for subsequent chemical cross-linking. In certain embodiments chemical cross-linking may be performed on cellulose, chitin, lignin, lignan, hemicellulose, pectin, and/or any other suitable biochemicals/biopolymers/structures which are naturally found in these organisms, for example.

In certain embodiments, the cellulose structure may be biochemically functionalized based on the intended use of the biomaterial. Such modification may expand functionality to suit particular uses. By way of example, cellulose has free hydroxyl groups that may be exploited to conjugate the material with different molecules. Two commonly used classes of reactions for this type of modification are acylation and alkylation reactions. Such reactions may allow for hydrocarbon chains of various lengths to be attached to the cellulose structure via the free hydroxyl groups. The different chain lengths and shapes may be particularly useful when steric hindrance is a factor. The use of larger chains may decrease the steric hindrance, and vice-versa. Acylation reactions using dicarboxylic acids may provide options to functionalize the biomaterial. Some of the classes of dicarboxylic acids that may be used may include linear saturated dicarboxylic acids, branched dicarboxylic acids, unsaturated dicarboxylic acids, substituted dicarboxylic acids, and aromatic dicarboxylic acids. In addition to acylation and alkylation reactions, other compounds may be used to mediate the connection between the functional groups and the cellulose, such as compounds containing boron, sulfur, nitrogen, and/or phosphorous, for example. Different functional groups may be added to the other end of the chain in order to provide a certain function. Such functional groups may include, for example, groups containing hydrocarbons, oxygen, nitrogen, sulfur, phosphorous, boron, and/or halogens. The selection of functional group may be made to suit the particular intended application. For example, in certain embodiments, if the intended application may be to prevent cell growth in certain areas, a steric non polar hydrocarbon functional group may be used; conversely, if the intended application is to promote cell growth, a carboxylic acid may be used, so that extracellular matrix proteins, such as collagen, may be bound to the cellulose.

In certain embodiments, the chemical modification of cellulose (or other such materials) may allow for control over the chemical and/or physical properties of the biomaterial. As a result, the biomaterial may be specialized for particular purposes in certain embodiments. For example, patterned cell growth may be provided by inhibiting cell growth in certain areas (temporarily or permanently) and promoting it in others. Moreover, cell-type specific molecules may be introduced to the biomaterial through such functionalization methods to promote the growth/invasion/differentiation of specific cell types. The functionalization of the biomaterial may allow for closer recreation of biologically relevant microenvironments, which may be relevant to cell function and/or tissue engineering.

In certain embodiments, at least a portion of two or more of the scaffold biomaterial subunits may be modified to feature carboxymethyl and/or hydroxyl ethyl cellulose functional groups, which may be cross-linked together by citric acid and heat to hold the composite scaffold biomaterial together.

In certain embodiments, the two or more scaffold biomaterial subunits may be assembled into the composite scaffold biomaterial and held together via gel casting using a hydrogel glue; via complementary interlocking geometry of the two or more scaffold biomaterial subunits; via guided assembly based biolithography (GAB); via chemical cross-linking; or any combinations thereof. Through a combination of two or more of these approaches, it is contemplated that structural integrity may be further increased, for example.

In certain embodiments of any of the composite materials, structures, or composite scaffold biomaterials described herein, the materials may further comprise one or more agents, such as a therapeutic drug, a signalling molecule, a growth factor, a metabolite, an ECM protein or component, or any combinations thereof.

In certain embodiments, examples of growth factors may include those described in the Wikipedia entry for Growth Factors (https://en.wikipedia.org/wiki/Growth_factor), which is herein incorporated by reference. In certain embodiments, therapeutic drugs may include anticoagulation, anti-inflammatory, and/or immunosuppressant drugs, or another therapeutic drug of interest, or any combinations thereof. In certain embodiments, ECM proteins or components may include, for example, collagen, elastin, fibronectin, laminin, or another ECM protein or component, or any combinations thereof.

In still another embodiment of any of the materials described herein, the decellularized plant or fungal tissue may be cellulose-based, hemicellulose-based, chitin-based, chitosan-based, pectin-based, lignin-based, lignan-based, or any combinations thereof.

In yet another embodiment of any of the materials described herein, the composite scaffold biomaterial may comprise at least two scaffold biomaterial subunits which are structurally different from one another. In certain embodiments, the at least two scaffold biomaterial subunits which are structurally different from one another may be derived from different plant or fungal sources, may be derived from different parts of the same plant or fungal source, may be derived from two different species of plant or fungal source, may exhibit different Young's modulus properties, may comprise different cell types, may comprise different hydrogels, or any combinations thereof.

In still another embodiment, there is provided herein a hydrogel, such as a cellulose-based hydrogel, comprising:

- a cross-linked matrix, such as a cross-linked cellulose matrix; and
- one or more channels formed in the cross-linked matrix by removal of a temporary space filler from the cross-linked matrix.

In certain embodiments, a hydrogel may comprise any suitable hydrogel, or mimic or functional equivalent thereof. In certain embodiments, a hydrogel may comprise a gel based on one or more macromolecule polymers that may be cross-linked and may hold water. In certain embodiments, rather than cross-linking, polymers may be entangled, or polymer melts may be used, or any combinations thereof. In certain embodiments, colloids may be used. In certain embodiments, the hydrogel may comprise a cross-linked matrix comprising cellulose, chitin, lignin, lignan, hemicellulose, pectin, and/or any other suitable biochemicals/biopolymers which are naturally found in plants or fungus, or any combinations thereof.

In certain embodiments, the temporary space filler may comprise a space-filling material which may be used to block surrounding material from occupying a space or region before the surrounding material has been set. Following setting of the surrounding material, the temporary space filler may be removed to leave a void in the structure. In certain embodiments, space fillers may comprise uncross-linked polymers, hydrogels, or colloids, for example.

In certain embodiments, the cross-linked matrix may be prepared from a decellularized plant or fungal tissue from which cellular materials and nucleic acids of the tissue are removed, the decellularized plant or fungal tissue comprising a 3-dimensional porous structure. In certain embodiments, the temporary space filler may comprise a temporary gel, such as an alginate hydrogel.

In certain embodiments, the matrix may be cross-linked around the temporary space filler, and the temporary space filler may then be removed from the cross-linked matrix, thereby forming the one or more channels. In certain embodiments, the temporary space filler may be removed by dissolution, heating, change in salt concentration, degradation, or any combination thereof. In certain embodiments, the temporary space filler may be positioned within the matrix to template a network of channels within the cross-linked matrix. In certain embodiments, the temporary space filler may be positioned within the matrix by deposition via 3D printing.

In certain embodiments, the hydrogel may further comprise one or more agents, such as a therapeutic drug, a signalling molecule, a growth factor, a metabolite, an ECM protein or component, or any combinations thereof.

In certain embodiments, the matrix may be prepared from a decellularized plant or fungal tissue which is cellulose-based, hemicellulose-based, chitin-based, chitosan-based, pectin-based, lignin-based, lignan-based, or any combinations thereof. In certain embodiments, the cross-linked matrix may comprise at least two structurally different celluloses. In certain embodiments, the at least two structurally different may be are derived from different plant or fungal sources, may be derived from different parts of the same plant or fungal source, may be derived from two different species of plant or fungal source, may exhibit different Young's modulus properties, may comprise different cell types, may comprise different hydrogels, or any combinations thereof.

In certain embodiments, there is provided herein a method for preparing a hydrogel having one or more channels, such as a cellulose-based hydrogel having one or more channels, said method comprising:

- providing a first cross-linkable material or gel, such as a natural or modified cellulose-, chitin-, lignin-, lignan-, hemicellulose-, or pectin-based material or gel;
- providing a temporary space filler;
- generating a 3-dimensional structure comprising the first cross-linkable material or gel with the temporary space filler distributed therein such that the temporary space filler templates one or more channels in the first cross-linkable material or gel, and cross-linking the first cross-linkable material or gel during or after generating the 3-dimensional structure; and removing the temporary space filler from the 3-dimensional structure to provide the hydrogel having one or more channels.

In certain embodiments, the first cross-linkable material or gel and the temporary space filler may be printed in an x-y plane, layer by layer, via one or more extruders (for example, a dual extruder using one extruder for the first cross-linkable material or gel and one extruder for the temporary space filler) to generate the 3-dimensional structure.

In certain embodiments, the temporary space filler may comprise a gel. In certain embodiments, the temporary space filler may comprise gelatin, and the structure may be cooled to maintain the gelatin in place. In certain embodiments, the first cross-linkable material or gel may comprise cellulose or a derivative thereof, and the cellulose may be cross-linked while printing, or after printing. In certain embodiments, after formation of the 3-dimensional structure and cross-linking of the cellulose, the temperature may be increased to melt the gelatin out of the 3-dimensional structure. Alternatively, in certain embodiments, the temporary space filler may comprise alginate gel crosslinked with calcium, and following generation of the 3-dimensional structure and cross-linking of the first cross-linkable material or gel the calcium may be exchanged with sodium in a wash salt to dissolve the alginate out of the 3-dimensional structure.

In still another embodiment, there is provided herein a scaffold biomaterial comprising:

a decellularized plant or fungal tissue from which cellular materials and nucleic acids of the tissue are removed, the decellularized plant or fungal tissue comprising a 3-dimensional porous structure;

at least a portion of the decellularized plant or fungal tissue being functionalized, complexed, or covalently bonded with one or more agents such as a therapeutic drug, a signalling molecule, a growth factor, a metabolite, an ECM protein or component, or any combinations thereof.

In certain embodiments, the decellularized plant or fungal tissue may be modified with a linker, such as a succinyl linker, which may be used for covalent bonding with the one or more agents; or wherein the decellularized plant or fungal tissue may be modified with carboxymethyl and/or hydroxyl ethyl cellulose functional groups, which may be used for covalent bonding with the one or more agents via citric acid and heat-based coupling.

In another embodiment, there is provided herein a use of any of the composite scaffold biomaterials, the hydrogels, or the scaffold biomaterials, or any combinations thereof, as described herein, for tissue repair or regeneration; in an implant; for culturing one or more cell types in vitro or in vivo; for mimicking an in vivo tissue or tissue interface; for bone tissue engineering; for repair or regeneration of bone; for transporting a fluid or liquid; for mimicking a tissue interface; for wound healing; for delivery of an agent such as a therapeutic drug, a signalling molecule, a growth factor, a metabolite, an ECM protein or component, or any combinations thereof; or any combinations thereof.

In yet another embodiment, there is provided herein a method for tissue repair or regeneration; for providing an implant; for culturing one or more cell types; for mimicking an in vivo tissue or tissue interface; for bone tissue engineering; for repair or regeneration of bone; for transporting a fluid or liquid; for mimicking a tissue interface; for wound healing; for delivery of an agent such as a therapeutic drug, a signalling molecule, a growth factor, a metabolite, an ECM protein or component, or any combinations thereof; or any combinations thereof; in a subject in need thereof, said method comprising:

providing a composite scaffold biomaterial as described herein, a hydrogel as described herein, or a scaffold biomaterial as described herein, or any combinations thereof; and introducing the composite scaffold biomaterial, the hydrogel, or the scaffold biomaterial, or any combinations thereof, to the subject at a site in need thereof.

In still another embodiment, there is provided herein a method for guiding cell alignment comprising:

providing a decellularized scaffold biomaterial comprising one or more channels or grooves;

seeding the deceullarized scaffold biomaterial with cells, or implanting the decellularized scaffold biomaterial at a position in contact with cells; and culturing the cells on the deceullarized scaffold biomaterial, thereby aligning the cells along the one or more channels or grooves.

In certain embodiments, the decellularized scaffold biomaterial may comprise grooves or channels derived from those naturally occurring in the structures formed from vascular bundles of the plant or fungal source. In certain embodiments, the grooves or channels may typically be about 1-100 micrometers in size, or any subrange or value therebetween. In certain embodiments, structures may be matched with a mammalian cell-type or structure of interest including, for example, fibroblasts, myofibroblasts, neurons, neuronal structures such as axons, endogenous stem cells, neutrophils, mesenchymal stem cells, satellite cells, myoblasts, myotubes, muscle progenitor cells, chondrocytes, tendon progenitor cells, tenocytes, periodontal ligament stem cells, or any combinations thereof.

In certain embodiments, the decellularized scaffold biomaterial may comprise a decellularized celery tissue. In certain embodiments, the cells may comprise muscle cells or precursors thereof. In certain embodiments, the cells may comprise myoblasts. In certain embodiments, the cells may comprise C2C12 myoblasts.

In certain embodiments, composite structures as described herein may be provided forming microchannels, which may be suitable for transporting water, nutrients, and/or for guiding directional cellular growth. In certain embodiments, composite structures as described herein may be prepared integrating diverse materials having different structural characteristics, so as to provide features such as stress shielding (i.e. hard and soft material), and/or soft and hard bone (i.e. trabecular and cortical).

In certain embodiments, unlike many commercial biomaterials, plant/fungus derived biomaterials as described herein may be substantially non-resorbable or poorly resorbable (i.e. they will not substantially breakdown and be absorbed by the body). The non-resorbable characteristic of these scaffolds may offer certain benefits. For example, in certain embodiments, biomaterials described herein may be resistant to shape change, and/or may hold their intended geometry over long periods of time. In certain embodiments, since they may have a minimal footprint compared to certain other products, they may be considered effectively invisible to the body, eliciting almost no immune response. When resorbable biomaterials break down, their by-products often illicit an adverse immune response, as well as induce oxidative stress and result in an increase of pH in the recovering tissue, which may be avoided by using a non-resorbable biomaterial.

Indeed, in certain embodiments, the decellularized plant or fungal tissues and/or scaffold biomaterials as described herein may further comprise living cells on and/or within the scaffold biomaterials. In certain embodiments, the living cells may be animal cells, mammalian cells, or human cells.

In certain embodiments, the plant or fungal tissue may be genetically altered via direct genome modification or through selective breeding, to create an additional plant or fungal architecture which may be configured to physically mimic a tissue and/or to functionally promote a target tissue effect. The skilled person having regard to the teachings herein will be able to select a suitable scaffold biomaterial to suit a particular application. In certain embodiments, a suitable tissue may be selected for a particular application based on, for example, physical characteristics such as size, structure (porous/tubular), stiffness, strength, hardness and/or ductility, which may be measured and matched to a particular application.

Moreover, chemical properties such as reactivity, coordination number, enthalpy of formation, heat of combustion, stability, toxicity, and/or types of bonds may also be considered for selection to suit a particular application. Such characteristics (physical and chemical) may also be directly modified before or after decellularization and/or functionalization to respond to the specific application.

In certain embodiments, scaffold biomaterials may be sourced from the same tissue or part of the plant or fungus, or from different parts or tissues of the plant or fungus. In certain embodiments, scaffold biomaterials may be sourced from the same individual plant or fungus, or from multiple plants or fungi of the same species. In certain embodiments, the scaffold biomaterials may be sourced from plants or fungi of different species, such that the scaffold comprises structures from more than one species. In certain embodiments, the scaffold biomaterials may be selected so as to provide particular features. For example, in certain embodiments, scaffold biomaterials having porosity and/or rigidity falling within a certain range may be selected, so as to mimic natural tissues and/or structures. In certain embodiments, the plant or fungal tissue may comprise apple, or apple hypanthium, tissue, or another plant or fungal tissue having similar porosity and/or rigidity characteristic(s).

In certain embodiments, the scaffold biomaterial may be a scaffold biomaterial configured to physically mimic a tissue of the subject and/or to functionally promote a target tissue effect in the subject. Methods of using such scaffold biomaterials as are described herein may, in certain embodiments, include a step of selecting a scaffold biomaterial as described herein for which the decellularised plant or fungal tissue is configured to physically mimic a tissue of the subject and/or to functionally promote a target tissue effect in the subject.

In certain embodiments, the decellularized plant or fungal tissue and/or scaffold biomaterials as described herein may further comprise living cells on and/or within the plant or fungal tissue. In certain embodiments, the living cells may be animal cells, mammalian cells, or human cells. In certain embodiments, the cells may be cells introduced or seeded into and/or onto the scaffold biomaterials and/or decellularized plant or fungal tissue, or may be cells infiltrating into or onto the scaffold biomaterials and/or decellularized plant or fungal tissue following implantation of the scaffold biomaterials and/or decellularized plant or fungal tissue into a living animal or plant subject, for example.

In an embodiment, there is provided herein a method for producing a scaffold biomaterial, said method comprising:

providing a plant or fungal tissue;

extracting one or more structures from the plant of fungal tissue; and preparing the scaffold biomaterial from the one or more extracted structures.

In certain embodiments, the extraction of the one or more structures from the plant or fungal tissue may comprise one or more manual steps which may be performed to extract or separate the one or more structures of interest from the surrounding plant or fungal tissue. Such manual steps may involve cutting, slicing, peeling, and/or other physical separation techniques. As will be understood, for large scale operations, such manual steps may become burdensome. As described herein, the present inventors thus developed extraction techniques which may be less burdensome and/or readily amendable to scale-up, for example. Accordingly, in certain embodiments, the step of extracting may comprise a liquid-based extraction to isolate the one or more structures from the plant or fungal tissue.

As will be understood, liquid-based extraction may comprise any suitable process for treating and extracting one or more structures from the plant or fungal tissue (which may be either native plant tissue or fungal tissue, or decellularized plant tissue or fungal tissue, or a combination thereof) using a liquid extraction solution. Typically, the liquid based extraction produces maceration of the plant or fungal tissue, whereby the plant or fungal tissue is disassembled into tissue/cellular components (including, for example, vascular bundles, lignocellulosicmatrixes or structures, single cells, and/or other structures of interest, or any combinations thereof). In certain embodiments, the liquid extraction solution may comprise a maceration solution, such as a salt solution, an acid solution, an acid and peroxide solution, or an alkaline/base solution. In certain embodiments, more than one treatment or solution may be used, either simultaneously or sequentially.

In certain embodiments, the step of extracting may comprise maceration with at least one of treatment with a salt solution; treatment with a base solution; treatment with an acid solution; or treatment with an acid and peroxide solution.

In certain embodiments, the step of extracting may comprise at least one treatment with a salt solution. As will be understood, the salt solution may comprise generally any suitable salt, such as any suitable salt capable of osmotic shock and/or disruption of hydrogen bonding and/or polymer crystal structure so as to extract intact tissue structures. As will be understood, particularly for food and/or medical applications, the salt may be selected to be appropriate for the particular application and may, for example, be selected to be physiologically occurring, easily washed away, nonharmful, and/or selected accordingly to a variety of factors relevant to the particular application, as desired. In certain embodiments, the salt may comprise NaCl, LiCl, $AlCl_3$, magnesium sulfate, potassium chloride, or calcium chloride, or any combinations thereof. In certain embodiments, the salt may comprise NaCl, LiCl, or any combination thereof. In certain embodiments, the salt may be monovalent, divalent, or trivalent. As will be understood, in certain embodiments the salt may be selected, at least in part, based on the intended application. Using different salts may have different electoscreening properties, activities, coordination profiles, and solubilties, for example. The salt may be dissolved/mixed in a suitable solvent to form the salt solution. Typically, the solvent may comprise water, although other solvents, or combinations of solvents (such as, for example, a mixture of water and ethanol), are also contemplated. The salt concentration in the salt solution may be tailored to suit the particular application of interest, particular solubilities, and/or other factors. Typically, the salt solution may comprise a salt concentration of about 0.1 to 10M, or any concentration therebetween (optionally rounded to the nearest 0.1), or any subrange spanning between any two of these concentrations. In certain embodiments, the salt concentration may be about 0.5M to 3M, or any value (optionally rounded to the nearest 0.1) therebetween, or any subrange spanning between any two of these concentrations. By way of example, in certain embodiments, the salt solution may comprise an aqueous solution of NaCl or LiCl, having a salt concentration of about 0.5M-3M. As will be understood, the salt solution, as well as the treatment conditions (i.e. heating, stirring) may be tailored to suit the particular application, desired structures to be extracted, plant or fungal tissue being used, etc. . . . , as desired.

In certain embodiments, salts may include a salt selected from the group consisting of salts having a cation selected from Lithium; Sodium; Potassium; Magnesium; Calcium; Iron; Copper; Zinc; Aluminum; or Ammonium; and an anion selected from Chloride; Acetate; Carbonate; Citrate; Fluoride; Nitrate; Phosphate; Sulfate; Iodide; or Borate, in any suitable combination. An example of a medicinal salt may include ibuprofenate. Depending on the salt and/or intended use of the products, neutralization and/or washing may be performed to remove residual salt and other reagents so as to prevent undesirable contamination, for example.

In certain embodiments, the step of extracting may comprise at least one treatment with a base solution. As will be understood, the base solution may comprise generally any suitable base, such as any suitable base capable of osmotic shock and/or disruption of hydrogen bonding and/or polymer crystal structure so as to extract intact tissue structures. As will be understood, particularly for food and/or medical applications, the base may be selected to be appropriate for the particular application and may, for example, be selected to be physiologically occurring, easily washed away, non-harmful, and/or selected accordingly to a variety of factors relevant to the particular application, as desired. In certain embodiments, the base may comprise NaOH, KOH, or a combination thereof. In an embodiment, the base may be dissolved/mixed in a suitable solvent, to form the base solution. Typically, the solvent may comprise water, although other solvents, or combinations of solvents (such as, for example, a mixture of water and ethanol), are also contemplated. The base concentration in the base solution may be tailored to suit the particular application of interest. Typically, the base solution may comprise a base concentration of about 0.1 to 10M, or any concentration therebetween (optionally rounded to the nearest 0.1), or any subrange spanning between any two of these concentrations. In certain embodiments, the base concentration may be about 0.5M to 3M, or any value (optionally rounded to the nearest 0.1) therebetween, or any subrange spanning between any two of these concentrations. By way of example, in certain embodiments, the base solution may comprise an aqueous solution of NaOH, having a concentration of about 0.5M-3M. As will be understood, the base solution, as well as the treatment conditions (i.e. heating, stirring) may be tailored to suit the particular application, desired structures to be extracted, plant or fungal tissue being used, etc. . . . , as desired.

In certain embodiments, bases may include a base selected from the group consisting of: Carbonates; Nitrates; Phosphates; Sulfates; Ammonia; Sodium hydroxide; Calcium hydroxide; Magnesium hydroxide; Potassium hydroxide; Lithium hydroxide; Zinc hydroxide; Sodium carbonate; Sodium bicarbonate; Butyl lithium; Sodium azide; Sodium amide; Sodium hydride; Sodium borohydride; or Lithium diisopropylamine Depending on the base and/or intended use of the products, neutralization and/or washing may be performed to remove residual base and other reagents so as to prevent undesirable contamination, for example.

In certain embodiments, the step of extracting may comprise at least one treatment with an acid solution. As will be understood, the acid solution may comprise generally any suitable acid, such as any suitable acid capable of osmotic shock and/or disruption of hydrogen bonding and/or polymer crystal structure so as to extract intact tissue structures. As will be understood, particularly for food and/or medical applications, the acid may be selected to be appropriate for the particular application and may, for example, be selected to be physiologically occurring, easily washed away, non-harmful, and/or selected accordingly to a variety of factors relevant to the particular application, as desired. In certain embodiments, the acid solution may comprise acetic acid, hydrochloric acid (HCl), $H_2SO_4$, or combinations thereof. In certain embodiments, the acid may be dissolved/mixed in a suitable solvent, to form the acid solution. Typically, the solvent may comprise water, although other solvents, or combinations of solvents (such as, for example, a mixture of water and ethanol), are also contemplated. In certain embodiments, the acid may be used "neat", i.e. without solvent. For example, acetic acid was used in certain examples described herein. The acid concentration in the acid solution may be tailored to suit the particular application of interest. Typically, the acid solution may comprise an acid concentration of about 0.1 to 10M, or any concentration therebetween (optionally rounded to the nearest 0.1), or any subrange spanning between any two of these concentrations. By way of example, in certain embodiments, the acid solution may comprise glacial acetic acid; acetic acid diluted with water (such as 50% diluted acetic acid); or HCl in water at a concentration of about 4M or less. As will be understood, the acid solution, as well as the treatment conditions (i.e. heating, stirring) may be tailored to suit the particular application, desired structures to be extracted, plant or fungal tissue being used, etc. . . . , as desired.

In certain embodiments, acids may include an acid selected from the group consisting of: Acetic acid; Boric acid; Carbonic acid; Hydrochloric acid; Citric acid; Hydrofluoric acid; Nitric acid; Oxalic acid; Phosphoric acid; Sulfuric acid; Boron trifluoride; Oxalic acid; Malonic acid; Succinic acid; or Malic acid. Additional examples may include dicarboxylic acids, such as linear saturated dicarboxylic acids, branched dicarboxylic acids, unsaturated dicarboxylic acids, substituted dicarboxylic acids, and aromatic dicarboxylic acids. Depending on the acid and/or intended use of the products, neutralization and/or washing may be performed to remove residual acid and other reagents so as to prevent undesirable contamination, for example.

In certain embodiments, the step of extracting may comprise at least one treatment with an acid and peroxide solution. As will be understood, the acid and peroxide solution may comprise generally any suitable acid and peroxide, such as any suitable acid and peroxide capable of osmotic shock and/or disruption of hydrogen bonding and/or polymer crystal structure so as to extract intact tissue structures. As will be understood, particularly for food and/or medical applications, the acid and peroxide may be selected to be appropriate for the particular application and may, for example, be selected to be physiologically occurring, easily washed away, non-harmful, and/or selected according to a variety of factors relevant to the particular application, as desired. Typically, the solution may comprise a suitable acid and a suitable peroxide mixture. In certain embodiments, the acid may comprise acetic acid, HCl, $H_2SO_4$, or any combinations thereof; and the peroxide may comprise generally any suitable peroxide, such as hydrogen peroxide. In certain embodiments, the acid and peroxide may be dissolved/mixed in a suitable solvent to form the acid and peroxide solution. Typically, the solvent may comprise water, although other solvents, or combinations of solvents (such as, for example, a mixture of water and ethanol), are also contemplated. The concentrations of the acid and peroxide in the solution may be tailored to suit the particular application of interest. Typically, the solution may comprise an acid concentration of about 0.1 to 15M, or any concentration therebetween (optionally rounded to the nearest 0.1), or any subrange spanning between any two of these concentrations; and a peroxide concentration of about 0.1 to 10M, or any concentration therebetween (optionally rounded to the nearest 0.1), or any subrange spanning between any two of these concentrations. In certain embodiments, the maceration solution may comprise a ratio of acid to peroxide of about 3:1 (such as a solution containing 13.05M acetic acid and 2.45M hydrogen peroxide) to about 1:3 (such as a solution containing 4.35M acetic acid and 7.35M hydrogen peroxide), or any ratio value therebetween (optionally rounded to the nearest 0.1), or any subrange spanning between any two of these ratios. By way of example, in certain embodiments the acid and peroxide solution may comprise acetic acid and hydrogen peroxide. In certain embodiments, the solution may comprise a solution of glacial acetic acid and 30% hydrogen peroxide in a ratio of 1:1 (by volume); or a solution of glacial acetic acid and 30% hydrogen peroxide in a ratio of 1:1 (as above), which has been diluted by 50% in water. As will be understood, the acid and peroxide solution, as well as the treatment conditions (i.e. heating, stirring) may be tailored to suit the particular application, desired structures to be extracted, plant or fungal tissue being used, etc. . . . , as desired.

In certain embodiments, acids may include an acid selected from the group consisting of: Acetic acid; Boric acid; Carbonic acid; Hydrochloric acid; Citric acid; Hydrofluoric acid; Nitric acid; Oxalic acid; Phosphoric acid; Sulfuric acid; Boron trifluoride; Oxalic acid; Malonic acid; Succinic acid; or Malic acid. Additional examples may include dicarboxylic acids, such as linear saturated dicarboxylic acids, branched dicarboxylic acids, unsaturated dicarboxylic acids, substituted dicarboxylic acids, and aromatic dicarboxylic acids. Depending on the acid and/or intended use of the products, neutralization and/or washing may be performed to remove residual acid and other reagents so as to prevent undesirable contamination, for example.

In certain embodiments, peroxides may include a peroxide selected from the group consisting of: hydrogen peroxide; peroxy acids, such as peracetic acid; metal peroxides (for example Lithium peroxide, barium peroxide); or organic peroxides (for example, dibenzoyl peroxide, benzoyl peroxide, methyl ethyl ketone peroxide). Depending on the peroxide and/or intended use of the products, neutralization and/or washing may be performed to remove residual peroxide and other reagents so as to prevent undesirable contamination, for example.

In certain embodiments, the step of extracting may comprise heating the plant or fungal tissue in the salt solution, the base solution, the acid solution, or the acid and peroxide solution. In certain embodiments, the heating may comprise heating to, or near, boiling, such as heating to a temperature of about 80-100° C., or any temperature value therebetween (optionally rounded to the nearest 0.1), or any subrange spanning between any two of these temperatures, for example. As will be understood, treatment temperature may be tailored to suit the particular application, solution being used (for example, treatment temperature may be reduced for harsh treatment solutions, or increased for weak treatment solutions), treatment time, desired structures to be extracted, plant or fungal tissue being used, for example. In certain embodiments, treatment temperature may change over course of treatment, for example starting hotter and ending cooler, or vice-versa.

In certain embodiments, treatment may be performed for at least about 1 minute, at least about 5 minutes, at least about 10 minutes, at least about 20 minutes, at least about 25 minutes, at least about 30 minutes, at least about 1 hour, at least about 2 hours, at least about 3 hours, or longer, or any time value or subrange therebetween. As will be understood, treatment time may be tailored to suit the particular application, solution being used (for example, treatment time may be lessened for harsh treatment solutions, or extended for weak treatment solutions), treatment temperature, desired structures to be extracted, plant or fungal tissue being used, for example.

In certain embodiments, examples of solvents may include a solvent selected from the group consisting of: Polar protic (such as propanol, ethanol, methanol, ammonia, acetic acid, water); Polar aprotic (such as acetone, dimethylformamide, dimethylsulfoxide); Organic; inorganic; or Amphiphilic solvents or colloids. Depending on the solvent and/or intended use of the products, neutralization and/or washing may be performed to remove residual solvent and other reagents so as to prevent undesirable contamination, for example.

As will be understood, treatment conditions may be tailored for the particular structure(s) of interest to be extracted. In the Examples below, individual structural cells were extracted from apple and pear, and substantially intact vascular bundles were extracted from celery and asparagus. For the vascular bundles, treatment conditions may be selected to be relatively less harsh (and/or treatment may be stopped earlier) so as to prevent destruction of the vascular bundles, whereas for individual structural cells a relatively more harsh treatment may be desirable, for example.

Detailed studies and description of liquid-based extraction/maceration techniques for extracting one or more structures from plant or fungal tissue can also be found in PCT patent application no. PCT/CA2020/050654 entitled "High Density Microchannels", which is herein incorporated by reference in its entirety.

In certain embodiments, the step of extracting may further comprise mechanically agitating, for example stirring, the plant or fungal tissue in the salt solution, the base solution, the acid solution, or the acid and peroxide solution.

As will be understood, in certain embodiments, the one or more structures from the plant or fungal tissue extracted during the step of extracting may comprise any suitable plant or fungal-derived 3-dimensional structure, such as one or more structures derived from hypanthium or pulp cellulose structures, microchannels such as xylem and/or phloem, or any combinations thereof.

In certain embodiments, the hypanthium or pulp structures (or any other plant or fungal structures/components of interest) may comprise an extended 3D structure (which may be comprised of any one or more of cellulose, hemicellulose, pectin, lignin, or the like; typically, the extended 3D structure may comprise a lignocellulosic structure/material) (which in certain embodiments may comprise a plurality of structural cells), single structural cells or groups of structural cells derived from the extended 3D structure, or any combinations thereof. In certain embodiments, the single structural cells or groups of structural cells derived from the extended 3D structure may comprise isolated structural cells, or small groups of clustered structural cells, the structural cells having a substantially intact 3-dimensional structure typically resembling a hollow cell or pocket, such as those shown in FIGS. 27-28. As will be understood, such structures may typically comprise lignocellulosic materials, such as cellulose and/or lignin-based structures. It will be understood that in certain embodiments, such structures may comprise other building blocks such as chitin and/or pectin, for example.

In certain embodiments of any of the above method or methods, the step of extracting may further comprise performing centrifugation. In certain embodiments, the centrifugation may separate extended 3D structures and/or microchannels such as xylem and/or phloem, from single structural cells or groups of structural cells derived from the extended 3D structures. In certain embodiments, the step of extracting may further comprise performing centrifugation, which separates extended 3D structures from single structural cells or groups of structural cells derived from the extended 3D structures. By way of example, in certain embodiments, centrifugation may produce an upper band or pellet comprising the single structural cells or groups of structural cells derived from the extended 3D structures. In still another embodiment, the one or more structures from the plant or fungal tissue may comprise the single structural cells or groups of structural cells derived from the extended 3D structures localized to the upper band or pellet.

In another embodiment of any of the above method or methods, the step of extracting may further comprise washing the one or more structures from the plant of fungal tissue.

In still another embodiment of any of the above method or methods, the step of preparing the scaffold biomaterial from the one or more extracted structures may comprise mixing, agitating, or physically manipulating the extracted structures to excise residual undesirable plant tissue materials; washing the one or more extracted structures from the plant or fungal tissue; or both.

In yet another embodiment of any of the above method or methods, the plant or fungal tissue may comprise decellularized plant or fungal tissue from which cellular materials and nucleic acids of the tissue are removed. In another embodiment of any of the above method or methods, the method may further comprise a step of decellularizing the plant or fungal tissue prior to the step of extracting. In still another embodiment of any of the above method or methods, the method may further comprise a step of decellularizing the one or more structures extracted from the plant of fungal tissue. Decellularization methods have already been described in detail herein.

In certain embodiments, the conditions for the step of extracting may be selected such that no, minimal, partial, or extensive decellularizing occurs during the extraction. In some applications, no, mimimal, or partial decellularization may be sufficient or desired. In other applications, particularly where thorough removal of remaining plant/fungal nucleic acids, proteins, etc. . . . , is desired, a deliberate decellularization treatment may be performed (such as the decellularization treatments described herein, including those employing SDS) either before or after the step of extracting.

In yet another embodiment of any of the above method or methods, the method may further comprise a step of decellularizing the plant or fungal tissue, or decellularizing the one or more structures from the plant or fungal tissue, or both. In another embodiment of any of the above method or methods, the step of preparing the scaffold biomaterial from the one or more extracted structures may comprise decellularizing the one or more extracted structures.

In still another embodiment of any of the above method or methods, the step of preparing the scaffold biomaterial from the one or more extracted structures may comprise grinding the one or more extracted structures. In certain embodiments of any of the above method or methods, a step of grinding may be performed on the plant or fungal tissue prior to extraction, and/or on the one or more extracted structures following extraction.

In yet another embodiment of any of the above method or methods, the step of preparing the scaffold biomaterial from the one or more extracted structures may comprise incorporating the one or more extracted structures into a matrix; or gluing or adhering extracted structures and/or scaffold biomaterials together; drying or lyophilizing the one or more extracted structures or scaffold biomaterials; seeding or culturing cells, such as animal cells, on the extracted structures and/or scaffold biomaterials; associating two or more extracted structures and/or scaffold biomaterials via layering, stacking, or other complementary/interlocking geometry; or any combinations thereof.

In certain embodiments, the matrix may comprise a hydrogel, forming a composite hydrogel.

In certain embodiments, the matrix or glue may comprise an alginate matrix, gelatin matrix, collagen matrix, or hyaluronic acid matrix, for example. In certain embodiments, the glue or matrix may comprise an alginate matrix.

In another embodiment, there is provided herein a scaffold biomaterial produced by any of the above method or methods.

In still another embodiment, there is provided herein a scaffold biomaterial comprising one or more structures extracted from plant or fungal tissue. Examples of such extracted structures may include those as described in detail hereinabove.

In still another embodiment of the above scaffold biomaterial, the one or more structures are extracted from the plant or fungal tissue by a liquid-based extraction, as described in detail hereinabove. In certain embodiments, the one or more structures may be extracted from the plant or fungal tissue by treatment with a salt solution; treatment with a base solution; treatment with an acid solution; or treatment with an acid and peroxide solution. Examples of such maceration solutions are detailed in the preceding paragraphs above.

In yet another embodiment, the one or more structures from the plant or fungal tissue may comprise a 3-dimensional structure, such as one or more structures derived from hypanthium or pulp cellulose structures, microchannels such as xylem and/or phloem, or any combinations thereof. In certain embodiments, the hypanthium or pulp cellulose structures may comprise an extended 3D structure, single structural cells or groups of structural cells derived from the extended 3D structure, or any combinations thereof. Such structures are described in detail in the preceding paragraphs above.

In still another embodiment of any of the above scaffold biomaterial or scaffold biomaterials, the one or more structures may comprise single structural cells or groups of structural cells derived from the extended 3D structures by centrifugation separation, as already described.

In yet another embodiment of any of the above scaffold biomaterial or scaffold biomaterials, the scaffold biomaterial may be a decellularized scaffold biomaterial lacking cellular materials and nucleic acids of the plant or fungal tissue. Approaches for decellularization have already been described in detail herein.

In another embodiment of any of the above scaffold biomaterial or scaffold biomaterials, the one or more structures may have been ground to reduce particle size, as described hereinabove.

In still another embodiment of any of the above scaffold biomaterial or scaffold biomaterials, the scaffold biomaterial may comprise a matrix into which the one or more structures are incorporated; a product formed by gluing or adhering extracted structures and/or scaffold biomaterials together; a product formed by drying or lyophilizing the one or more extracted structures or scaffold biomaterials; a product formed by seeding or culturing cells, such as animal cells, on the extracted structures and/or scaffold biomaterials; a product formed by associating two or more extracted structures and/or scaffold biomaterials via layering, stacking, or other complementary/interlocking geometry; or any combinations thereof.

In yet another embodiment of any of the above scaffold biomaterial or scaffold biomaterials, the matrix may comprise a hydrogel. In another embodiment of any of the above scaffold biomaterial or scaffold biomaterials, the matrix or glue may comprise alginate or another suitable matrix or glue described herein or known to the person of skill in the art having regard to the teachings herein.

In another embodiment, there is provided herein a food product comprising a scaffold biomaterial, the scaffold biomaterial comprising one or more 3-dimensional structures derived or extracted from a plant or fungal tissue.

As will be understood, a wide variety of scaffold biomaterials (also referred to herein as composite scaffold biomaterials) are described in detail herein, many of which may be suitable for such food products. The skilled person having regard to the teachings herein will recognize that scaffold biomaterials may be selected from those described herein to tailor characteristics, such and structure and/or texture, to suit the particular food product application of interest.

In certain embodiments, the food product may comprise a scaffold biomaterial, the scaffold biomaterial comprising one or more 3-dimensional structures derived or extracted from a plant or fungal tissue, wherein the one or more 3-dimensional structures may comprise any suitable plant or fungal-derived 3-dimensional structure, such as one or more structures derived from hypanthium or pulp structures, microchannels such as xylem and/or phloem, or any combinations thereof.

In certain embodiments, the hypanthium or pulp structures (or any other suitable plant or fungal structures/components) may comprise an extended 3D structure (which may comprise any one or more of cellulose, hemicellulose, pectin, lignin, or the like; typically, the extended 3D structure may comprise a lignocellulosic structure) (which in certain embodiments may comprise an extended network comprising plurality of structural cells), single structural cells or groups of structural cells derived from the extended 3D structure, or any combinations thereof. In certain embodiments, the single structural cells or groups of structural cells derived from the extended 3D structure may comprise isolated structural cells, or small groups of clustered structural cells, the structural cells having a substantially intact 3-dimensional structure typically resembling a hollow cell or pocket, such as those shown in FIGS. 27-28. As will be understood, such structures may typically lignocellulosic materials, such as cellulose and/or lignin-based structures. It will be understood that in certain embodiments, such structures may comprise other building blocks such as chitin and/or pectin, for example.

In yet another embodiment of any of the above food product or food products, the one or more structures derived from hypanthium or pulp structures may comprise an extended 3D structure, single structural cells or groups of structural cells derived from the extended 3D structure, or any combinations thereof, as already described in detail hereinabove.

In another embodiment of any of the above food product or food products, the scaffold biomaterial (or the one or more 3-dimensional structures thereof) may be decellularized, the one or more 3-dimensional structures lacking cellular materials and nucleic acids of the plant or fungal tissue. Approaches for decellularization have already been described in detail hereinabove.

In still another embodiment of any of the above food product or food products, the scaffold biomaterial may comprise any of the scaffold biomaterial or scaffold biomaterials as described herein, selected to suit the particular or desired application.

In yet another embodiment of any of the food product or food products, the scaffold biomaterial may comprise a matrix into which the one or more 3-dimensional structures are incorporated; a product formed by gluing or adhering the one or more 3-dimensional structures and/or scaffold biomaterials together; a product formed by drying or lyophilizing the one or more 3-dimensional structures or scaffold biomaterials; a product formed by seeding or culturing cells, such as animal cells, on the 3-dimensional structures and/or scaffold biomaterials; a product formed by associating two or more extracted structures and/or scaffold biomaterials via layering, stacking, or other complementary/interlocking geometry; or any combinations thereof.

In another embodiment of any of the above food product or food products, the scaffold biomaterial may comprise a matrix into which the one or more 3-dimensional structures are incorporated; a product formed by gluing or adhering the one or more 3-dimensional structures and/or scaffold biomaterials together; or any combination thereof.

In still another embodiment of any of the above food product or food products, the matrix or glue may comprise alginate or another suitable matrix or glue described herein or known to the person of skill in the art having regard to the teachings herein.

In yet another embodiment of any of the food product or food products, the scaffold biomaterial may comprise two or more different 3-dimensional structures derived or extracted from the same, or different, plant or fungal tissues. In another embodiment, the food product may comprise two or more different scaffold biomaterials having different structural or physical properties. In still another embodiment, the two or more different 3-dimensional structures, and/or the two or more different scaffold biomaterials, may be selected so as to provide a target stiffness, mouth-feel, and/or texture to the food product. Considerations for scaffold biomaterial selection and combination, and benefits which may be obtained therefrom particularly in terms of tunability of structural properties, are described in detail throughout the present specification.

In yet another embodiment of any of the above food product or food products, one or more cells are seeded or cultured on the scaffold biomaterial and/or 3-dimensional structures. In certain embodiments, the one or more cells may comprise animal cells, such as cells of a livestock animal, fish, insect, or other animal of interest. In certain embodiments, the animal cells may comprise bovine, porcine, fish, elk, chicken, turkey, or avian cells, for example. In certain embodiments, the one or more cells may comprise muscle cells, fat cells, connective tissue cells (i.e. fibroblasts), cartilage, bone, epithelial, or endothelial cells, or any combinations thereof.

In still another embodiment of any of the above food product or food products, the food product may comprise at least a first layer of scaffold biomaterial and a second layer of scaffold biomaterial, one of the layers being seeded with muscle cells and the other of the layers being seeded with fat cells.

In yet another embodiment of any of the above food product or food products, the one or more cells may be aligned along one or more channels or grooves of the scaffold biomaterial and/or of the 3-dimensional structures. In certain embodiments, the one or more cells may comprise muscle cells. Cell alignment is described in further detail in Example 6 below. In certain embodiments, it is contemplated that such cell alignment may be used to more closely mimic meat tissue characteristics, for example.

In still another embodiment of any of the above food product or food products, the food product may comprise one or more 3-dimensional structures derived from hypanthium or pulp structures, and one or more microchannel structures. In yet another embodiment of any of the above food product or food products, the 3-dimensional structures derived from hypanthium or pulp structures comprise an extended 3D structure, single structural cells or groups of structural cells derived from the extended 3D structure, or any combinations thereof. In another embodiment of any of the above food product or food products, the microchannel structures may comprise xylem and/or phloem. In still another embodiment of any of the above food product or food products, the xylem and/or phloem may be provided in the form of vascular bundles. Such 3-dimensional structures have already been described in detail hereinabove.

In yet another embodiment of any of the above food product or food products, the scaffold biomaterial may comprise any of the composite scaffold biomaterials as described herein, selected to suit the particular application of interest.

As will be understood, a food product may refer to any suitable edible product, or precursor thereof or starting material therefor. The food product may be provided in a variety of different forms. In certain embodiments, the food product may comprise the scaffold biomaterial, and may be in a ready-to-use, ready-to-cook, pre-cooked, smoked, cured, dried/lyophilized, frozen, vacuum sealed, or other suitable form or format, either with or without one or more additional components, seasonings, dyes, preservatives, or other food product-related agents. Food products may be decellularized, or ready for decellularization, to remove plant and/or fungal cells. Food products may be pre-seeded with cell(s) of interest, may be ready for seeding with cells of interest, or may be cell-free. The skilled person having regard to the teachings herein will be aware of a variety of different forms and formats for the food products described herein, and will recognize that the food product may be adapted as desired to suit the particular application of interest.

In certain embodiments, scaffold biomaterials and/or food products as described herein may be for use as a base scaffold, that can be used with one or more other materials, agents, cells, fillers, etc. . . . to impart one or more additional characteristics, such as those relating to color, taste, and/or mouthfeel or texture, for example.

In certain embodiments, food products as described herein may be for use as, or in the preparation of, meat alternatives/mimics. While the food products described herein may have a wide variety of different applications in the food industry, meat alternatives/mimics are of particular interest given the environmental issues often associated with livestock. Food products as described herein may be considered as being akin to plant-based meat alternatives/mimics; however, it will be recognized that food products as described herein may also be well-suited for growth/culturing of animal cells (such as muscle and/or fat cells of livestock animals) within the scaffolds, which may be used to improve mouth-feel, texture, structure, appearance, and/or food experience of the food products in certain examples, and so in some embodiments the food products may additionally include animal cells, and so may not be entirely plant-based in such embodiments. In embodiments where animal cells are used, such food products may be considered as being more akin to lab-grown food products, for example.

In another embodiment, there is provided herein a method for preparing a food product, the method comprising:

producing a scaffold biomaterial by:

providing a plant or fungal tissue;

deriving or extracting one or more 3-dimensional structures from the plant of fungal tissue; and preparing the scaffold biomaterial from the one or more derived or extracted 3-dimensional structures; and preparing the food product from the scaffold biomaterial.

In another embodiment of the above method, the step of producing the scaffold biomaterial may comprise performing any of the method or methods described hereinabove. Indeed, methods for producing scaffold biomaterials have already been described in detail hereinabove.

In still another embodiment of any of the above method or methods, the step of preparing the food product from the scaffold biomaterial may comprise any one or more of incorporating the one or more derived or extracted 3-dimensional structures into a matrix; or gluing or adhering derived or extracted 3-dimensional structures and/or scaffold biomaterials together; drying or lyophilizing the one or more derived or extracted 3-dimensional structures or scaffold biomaterials; seeding or culturing cells on the derived or extracted 3-dimensional structures and/or scaffold biomaterials; associating two or more derived or extracted 3-dimensional structures and/or scaffold biomaterials via layering, stacking, or other complementary/interlocking geometry; or any combinations thereof.

In yet another embodiment of any of the above method or methods, the step of preparing the food product from the scaffold biomaterial may comprise seeding or culturing cells on the derived or extracted 3-dimensional structures and/or scaffold biomaterials.

In another embodiment of any of the above method or methods, the one or more cells may comprise animal cells, such as cells of a livestock animal, fish, insect, or other animal of interest. In certain embodiments, the cells may comprise bovine, porcine, fish, elk, chicken, turkey, or avian cells, for example. In certain embodiments, the one or more cells may comprise muscle cells, fat cells, connective tissue cells (i.e. fibroblasts), cartilage, bone, epithelial, or endothelial cells, or any combinations thereof.

In still another embodiment of any of the above method or methods, the method may comprise producing at least a first layer of scaffold biomaterial and a second layer of scaffold biomaterial, one of the layers being seeded with muscle cells and the other of the layers being seeded with fat cells.

In yet another embodiment of any of the above method or methods, the method may comprise aligning the one or more cells along one or more channels or grooves of the scaffold biomaterial and/or of the 3-dimensional structures. Approaches for cell alignment are already described in detail hereinabove, and in Example 6 below. In certain embodiments, the one or more cells may comprise muscle cells.

In still another embodiment of any of the above method or methods, the method may comprise producing two or more different scaffold biomaterials having different structural or physical properties; producing one or more scaffold biomaterials comprising two or more different 3-dimensional structures derived or extracted from the same, or different, plant or fungal tissues; or any combinations thereof. In yet another embodiment, the two or more different 3-dimensional structures, and/or the two or more different scaffold biomaterials, may be selected so as to provide a target stiffness, mouth-feel, and/or texture to the food product, for example.

EXAMPLES

Living tissues are complex structures consisting of a collection of different cell types. Various cell types may interact to perform specialized functions within the body. Cellular and extracellular matrix organization is often directly related to function; consequently, impaired cellular, tissue, and/or organ function may result from both biochemical and physical defects, ranging from genetic disorders to physical injuries. Biochemical and physical environments in the body may vary within, at the interface, and between different tissue types and organs. As such, recreating or approximating the natural in vivo environment of the cell is difficult. Substantial research has been directed toward producing biomimetic constructs. A variety of approaches have been proposed as potential avenues to recapture the native environment including synthetic biology, regenerative medicine, grafting, templating, and scaffolding. However, recreation of the cellular microenvironment has been challenging. As tissues are themselves complex composite materials, simple materials typically do not allow for biochemical and physical complexity to mimic the natural environment. Thus, extensive research has been dedicated to composite materials developed from one or more of the aforementioned approaches to biomaterial production.

An attractive approach for biomaterial design is decellularization, wherein a scaffolding material made of the ECM proteins void of cells replaces the damaged tissue. This concept is based on an idea that the damaged tissue may be replaced with a scaffold of the same tissue or organ; the scaffold may be repopulated by healthy cells, and proper tissue or organ function may be restored. Typically such organ decellularization approaches have had several challenges including reliance on donor tissue, compatibility issues, and practical limitations. Alternatively, synthetic approaches may provide several other biomaterial production methods including 3D printing, casting, and electrospinning which have been developed to create custom structures that may circumvent certain shortcomings of the organ decellularization approach. Ideally, the high degree of complexity in the structures obtained by organ decellularization or grafting may be combined with the customizability and control associated with the synthetic biomaterial approach. By combining both techniques, it may be possible to produce materials that more closely replicate healthy tissue, for example.

Example 1—Composite Biomaterials Assembled by Gel Casting

In this example, different scaffold biomaterial subunits are combined via gel casting using a hydrogel to join the subunits together. Although it is contemplated that many different hydrogels may be used, this example mainly relates to gelatin, collagen, and agarose hydrogels. In certain embodiments, hydrogels may comprise gelatin, collagen, agarose, hyaluronic acid, alginate, fibrin, fibronectin, agar, PEG, PVA, or any combinations thereof, for example. In certain embodiments, two or more scaffold biomaterial subunits may be used as a scaffold for the hydrogel to form around, wherein the hydrogel may have one or more features tailored for the desired application. In certain embodiments, materials having different properties may be joined together in such manner. For example, in certain embodiments different regions of the material(s) may have different topographies, densities, chemical functional groups, mechanical properties, porosities, or any combinations thereof.

In the following studies, scaffold biomaterial subunits were generated by carving the scaffold biomaterials into desired shapes using a CNC or biopsy bunch to provide precision and reproducibility. The desired shapes were then removed from the bulk material by slicing on a mandolin slicer. The thickness of the Mandolin slice was used to set the z thickness of the material. Subsequently, the material was decellularized and sterilized as described in WO2017/136950, entitled “Decellularised Cell Wall Structures from Plants and Fungus and Use Thereof as Scaffold Materials”, herein incorporated by reference in its entirety. The scaffold biomaterial subunits were then ready for cell culture and/or implantation, and may be readily assembled into final form by coating with the hydrogel. It is contemplated that either temporary or permanent hydrogels may be used, and may provide time-dependent biochemical and/or physical cues, for example By way of example, it is contemplated that in certain embodiments a synthetic vessel may be generated by stacking subunits (for example, ring-shaped subunits) on top of one another and coating the structure with a hydrogel such as agarose. In such examples, the agarose may be a liquid at higher temperatures (i.e. above about 65° C.), but remain solid at physiological temperatures, such that the agarose may solidify around the stack of subunits following application, creating a synthetic vessel (for example, a flexible tube-like structure).

3D biocompatible scaffolds consisting of decellularized plant tissue have been developed. These biomaterials may support cell growth, invasion, and/or proliferation in vitro and in vivo. As described, composite materials of cellulose scaffolds and hydrogels have been developed, where the presence of the hydrogel may allow for distinct biochemical and physical cues to be temporarily or permanently introduced. The cellulose scaffolding may be an attractive base material because of its high biocompatibility, natural abundance, simple production, low cost, and/or complex structures. Plants have evolved to produce complex specialized structures. Remarkably, many of these structures are related to those found in the human body. Creating composite materials comprising these plant structures may create biomimetic materials for tissue engineering. In certain embodiments, preparing larger sizes may create difficulties due to size of the source materials. Accordingly, composite plant-based materials may be a solution to size limitations imposed by nature. Multicomponent systems may be used to retain features of the source material, but expand the configurability though designing materials with different chemical and/or physical environments, for example. By way of example, a composite material may be designed to have regions with different porosities and/or mechanics, while maintaining the intricate features of the source plant structures. An example of a direct result of using materials with different mechanical properties is the phenomenon of stress shielding. Stress shielding may occur in the body and may be a key issue with bone implants. Inadequate or abundant stress shielding may result in damage or degradation of the surrounding healthy tissue. Further, the interfaces between different tissues often separate regions of radically different microenvironments. By designing composite materials, interfaces of different cell populations and environments may be mimicked.

This example investigates creating composite cellulose-based, plant-derived scaffolds. The scaffolds were combined by gel casting. These gel-casted composites may provide an appealing approach to biomaterial design. This example shows that a complex biomaterial may be assembled from subunits, and the subunits may be held together with a biocompatible hydrogel. The cells which are cultured on and/or in the resultant composites may be exposed to different structural, mechanical, and/or chemical environments. Cells may invade the scaffolds and may proliferate in the gels connecting the subunits and across their interfaces. Moreover, the cell migration may be impeded with the presence of existing cells on adjacent scaffolds, or by using less porous hydrogels, for example. The composite materials demonstrated stress shielding, supported the growth of different cell types, and created interfaces between distinct tissues in these studies.

Accordingly, results indicate that the hydrogel may keep the overall structure together, providing structural integrity. Although many different hydrogels may be used, this illustrative example is focused on gelatin, collagen, and/or agarose. First, the starting material was carved into its desired shape. To perform the carving, a CNC or a biopsy punch was used to allow greater precision and reproducibility. The desired shape was then removed from the bulk material by slicing on a Mandolin slicer. The thickness of the Mandolin slice set the z thickness of the material.

Subsequently, the material was decellularized and sterilized as per established protocol, see WO2017/136950, entitled "Decellularised Cell Wall Structures from Plants and Fungus and Use Thereof as Scaffold Materials", herein incorporated by reference in its entirety. The material was then ready for cell culture/implantation and was readily assembled into the final form by coating with the hydrogel. Temporary and permanent hydrogels may be used to provide time-dependent biochemical and physical cues, for example. For instance, in certain embodiments, a synthetic vessel may be created by stacking rings of scaffold biomaterial on top of one another, and coating with a hydrogel such as agarose. The agarose may be liquid at high temperatures (above 65° C., but may remain solid at physiologically relevant temperatures). The agarose may solidify around the stack of rings, creating a vessel or flexible tube-like structure.

Materials and Methods

Scaffold production: A mandolin slicer was used to slice McIntosh Red apples (Canada Fancy) into thin 1.2 mm sections, measured with a Vernier caliper. A 5 mm diameter disk with a 1.2 mm thickness was then carved out of the hypanthium tissue of the slice, and a 2 mm disk was removed from the centre of the 5 mm disk with a Carbide 3D Shapeoko 3 CNC machine and the Chilipeppr jpadie software. The scaffolds were cut at a speed of 1 mm/s with a 0.8 mm diameter drill bit and an angle of 180°. The subunits were designed using Inkscape and were converted into the gcode using Jscut. Thus, a macroscopic ring was obtained with an inner diameter of 2 mm, an outer diameter of 5 mm, and a thickness of 1.2 mm. The samples were transferred to a 0.1% SDS solution and decellularized for 48 h while being shaken at 180 RPM. After decellularization, the samples were washed three times with $dH_2O$. Next, the rings were incubated in 100 mM $CaCl_2$ for 24 h at room temperature to remove any surfactant residue. The samples were washed three times with $dH_2O$ to remove the salt residue, and then they were incubated with 70% ethanol for sterilization. After the removal of the ethanol, three washes with $dH_2O$ were performed to yield a sterile ring, free of contaminants. Alternatively, the samples may be autoclaved to be sterilized.

Artificial vessel construction: The decellularized apple-derived cellulose scaffold rings were stacked on a needle and assembled into a vessel by coating with 1.5% agarose. The vessel was left to cool for 30 minutes.

In vivo biocompatibility test: Vessels containing two subunits were implanted subcutaneously into rats and later resected to assess biocompatibility and integrity.

Chemically crosslinked hydrogel glue: 5×5×1.2 mm pieces of decellularized apple were cut and prepared according to established protocol (see Hickey et al., 2018, Customizing the Shape and Microenvironment Biochemistry of Biocompatible Macroscopic Plant-Derived Cellulose Scaffolds Ryan J. Hickey, Daniel J. ACS Biomaterials Science & Engineering 2018 4 (11), 3726-3736 and WO2017/136950;). The subunits were combined by using a gelatin crosslinked with glutaraldehyde glue. The glutaraldehyde was reduced with sodium borohydride. Cells were plated on the constructs and evaluated for viability.

Figure 8:
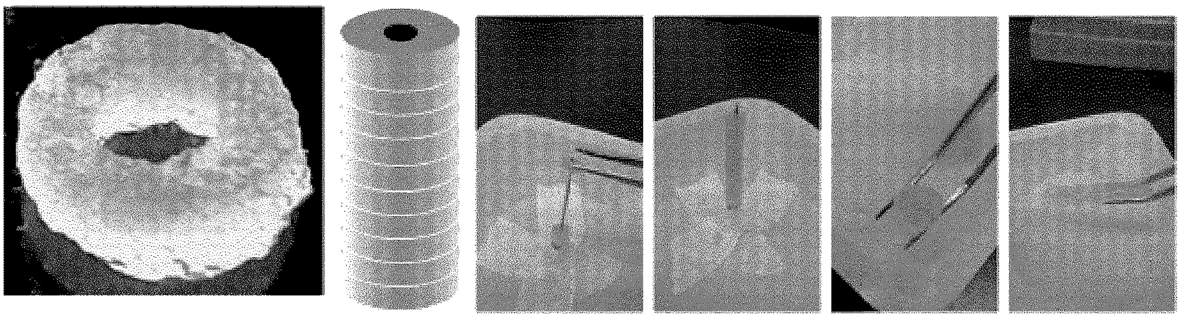
FIG. 8 shows images relating to an artificial vessel and assembly thereof from ring-like subunits. Ring subunits were stacked and coated with 1.5% agarose to make an artificial vessel.

Results and Discussion:

Composite material production—The process of combining subunits with a hydrogel was successfully established. The hydrogel used in this example was 1.5% agarose. Apple-sourced rings were stacked and assembled by coating with a hydrogel (1.5% agarose). The resulting structure was a vessel. FIG. 8 shows, from left to right, images of a ring subunit, a model of the tube-like structure, the tube-like structure at various stages of assembly, and the final ring structure artificial vessel product.

Figure 9:
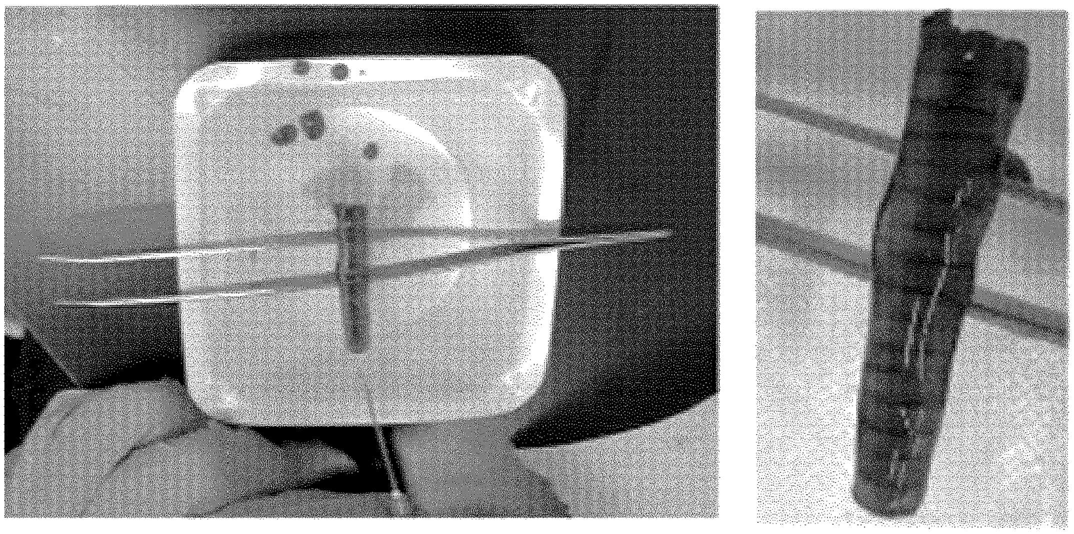
FIG. 9 shows results of a fluid transport test, in which congo red stain was flowed through the vessel depicted in FIG. 8.

Liquid flow test—a congo red solution was passed through the vessel to demonstrate the ability of the tube-like structure to flow/transport liquid. FIG. 9 shows results of the fluid transport test, in which congo red stain was successfully flowed through the vessel depicted in FIG. 8.

Figure 25:
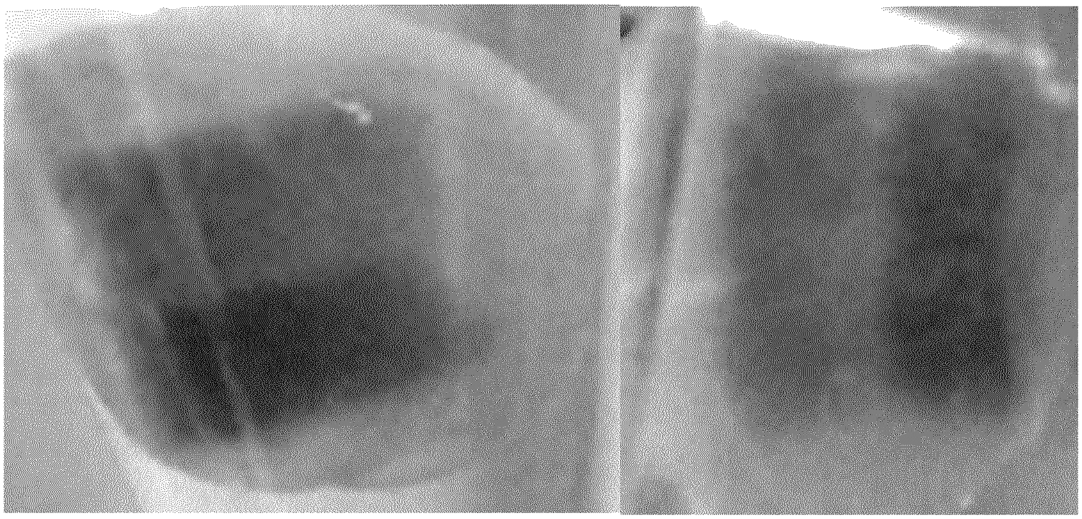
FIG. 25 shows resected composite vessels. The composite vessels were formed by casting 1.5% agarose around two stacked decellularized apple-derived cellulose rings. The samples were implanted subcutaneously in rats for 4 weeks. They were then resected and it was observed that they remained intact and showed no signs of infection or encapsulation/rejection.

Biocompatibility—the vessels/unit remained intact in vivo and were biocompatible, cells grew on the scaffold. FIG. 25 shows the resected composite vessels. The composite vessels were formed by casting 1.5% agarose around two stacked decellularized apple-derived cellulose rings.

The samples were implanted subcutaneously in rats for 4 weeks. They were then resected (removed) and it was observed that they remained intact and showed no signs of infection or encapsulation/rejection.

Figure 10:
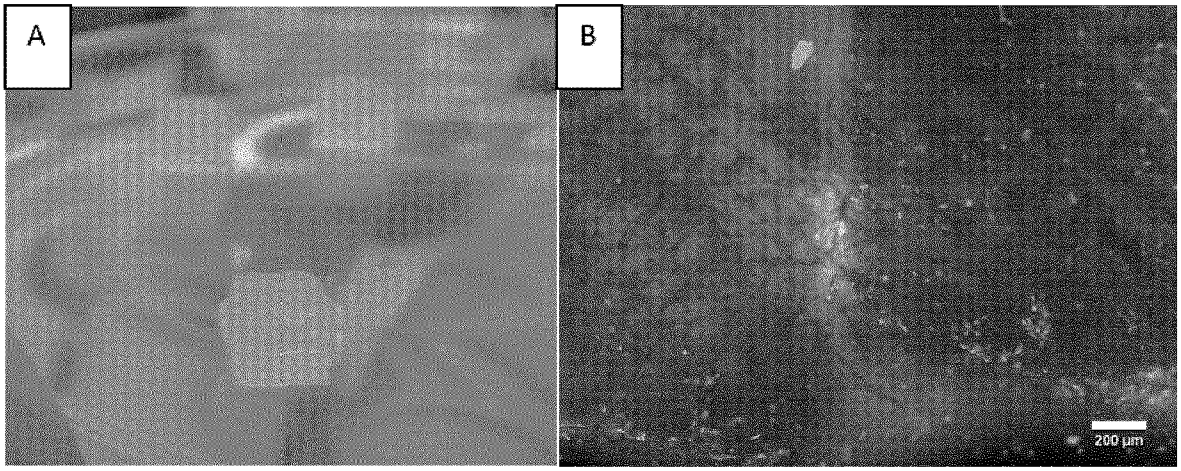
FIG. 10 shows images of glued composite biomaterials. Biomaterials were glued with gelatin crosslinked with glutaraldehyde and reduced with sodium borohydride. (A) shows two subunits of apple-derived cellulose scaffold glued together. (B) shows that the glued construct supported cell growth of GFP 3T3 cells.

Biomaterial glue—A gelatin crosslinked with glutaraldehyde gel was used to glue subunits together in another exemplary structure. The intact unit supported cell growth in vitro. FIG. 10 shows images of glued composite biomaterials made by gluing with gelatin crosslinked with glutaraldehyde. The biomaterials were glued with gelaten crosslinked with glutaraldehyde and reduced with sodium borohydride. (A) shows two subunits of apple-derived cellulose scaffold glued together, and (B) shows that the glued construct supported cell growth of GFP 3T3 cells.

Modifications such as gluing, gel casting, chemical functionalization, loading with one or more agents (i.e. drugs, signalling molecules, growth factors, metabolites, etc.) may further expand the functionality of materials and devices described herein.

Gel casted composites may allow for designing of structures and features that are not found in nature, while exploiting the natural complexity of the scaffold material in the individual subunits. Moreover, approaches as described herein may allow for more complicated physical and/or mechanical properties (i.e. stress shielding and site-specific moduli, channels, pores, etc.). These composites may be used to combine different cell types in different regions. This approach may provide an alternative, or a complement, to interlocking composites particularly in applications where physical connections are not desirable, inapplicable, or insufficient. Agarose is an example of a hydrogel which may be used, and it will be understood that many others are also contemplated such as materials including one or more of gelatin, collagen, and hyaluronic acid, for example.

The approach in this example may provide an ability to have tunable biochemical, biophysical, and mechanical properties of cellulose, hemicellulose, chitin, chitosan, pectin, lignin-based, and/or lignan-based scaffold biomaterials. Further, time dependent/independent release of drugs, signalling molecules, growth factors, metabolites, and/or ECM proteins and/or components (i.e. ions, sugars, proteoglycan, metabolites, etc. . . . ), or any combinations thereof, may be combined in the composite hydrogel. This may also allow for creating larger macro objects with varying degrees of flexibility and articulation, for example.

FIG. 1 shows an example of a contemplated application of composite materials as described herein, wherein the composite materials may be generated in the form of blood vessels. Blood vessels are complex structures with different layers of tissues (upper left and central images). In the examples provided herein, ring structures have been prepared (also see top and bottom centre images) from apple derived cellulose that may be stacked and coated with a hydrogel such as 1.5% agarose to produce a vessel (bottom right and left images). This vessel may be wrapped with different layers or membranes containing different cell types. A sample material for the membrane may be decellularized orange pith membranes (see upper right image), for example Combining multiple elements may be used to more closely recreate complex structures such as blood vessels, which have different tissues and cell types organized radially. The central image of this figure has been adapted from Blausen.com staff (2014), Medical Gallery of Blausen Medicial 2014, Wiki Journal of Medicine 1(2).

It is contemplated that by assembling subunits in this manner using a hydrogel for providing structural integrity and holding the structure together, a wide variety of larger and/or diverse structures may be generated. This approach may also allow for significant customization and control of structural properties. Through selection of scaffold biomaterial (which may be all the same, or may be a mixture of two or more different scaffold biomaterials, as desired), selection of subunit shape, and/or selection of hydrogel, a high level of control and tunability over resulting structures may be achieved.

In certain embodiments, it is contemplated that the present approaches may provide for structures and/or features that are not found in nature, while exploiting the natural complexity of the scaffold biomaterial source(s) within the individual subunits. As well, such approaches may allow for control and/or creation of complex physical and mechanical properties (i.e. stress shielding and site specific moduli, channels, pores, etc., as desired). It is contemplated that such approaches may allow for the combination of different cell types in different regions of the resultant structures. Further, by using hydrogel or other gel, it is contemplated that such approaches may allow for combining subunits even in applications where simple physical connections are not desirable, inapplicable, and/or insufficient. In certain embodiments, it is contemplated that such approaches may be used to provide structures having seals for flowing liquid and/or for creating semipermeable interfaces, for example. In certain embodiments, it is contemplated that the hydrogel may be or comprise agarose, gelatin, collagen, or hyaluronic acid hydrogel, or any combinations thereof.

In certain embodiments, scaffold biomaterials as described herein may be functionalized and/or loaded with one or more agents tailored for a desired application. Such agents may include, for example, any one or more of a therapeutic drug, a signalling molecule, a growth factor, a metabolite, an ECM protein or component, or any combinations thereof. In certain embodiments, agents may provide for time-dependent or time-independent release of such agents. In certain embodiments, one or more agents may be covalently bonded, directly or indirectly via a linker, to a cellulose-based, hemicellulose-based, chitin-based, chitosan-based, pectin-based, lignin-based, and/or lignan-based scaffold biomaterial. In certain embodiments, one or more acylation and alkylation-type reactions, or other suitable reactions using sulfur, nitrogen, boron, and/or halide compounds (i.e. thiols, imides, amines, amides, borohydrides, borohydrates, and halides) may be used.

In certain embodiments, it is contemplated that structures as described herein may be designed such that one or more sections of the structure are more or less hydrophobic or hydrophilic versus one or more other sections of the structure.

In certain embodiments, it is contemplated that structures as described herein may be designed such that site and/or cell-type specific attractants and/or deterrents are employed at appropriate regions of the structure to suit the particular application.

In certain embodiments, scaffold biomaterial subunits as described herein may be customizable with respect to shape and/or structure. In certain embodiments, larger and/or more complex structures may be prepared from such subunits, which may have varying and/or controllable flexibility and/or articulation.

While this example focuses on using a hydrogel, it is also contemplated that any of a glue, coating, gel, and/or paste, or any combinations thereof, may be used for holding the subunits together within the structure.

In certain embodiments, scaffold biomaterials as described herein may be cellulose-based, hemicellulose-based, chitin-based, chitosan-based, pectin-based, lignin-based, lignan-based, or any combinations thereof. In certain embodiments, composite structures as described herein may be tunable with respect to their biochemical, biophysical, and/or mechanical properties.

While this example mainly relates to gel casting approaches, it is contemplated that in certain embodiments the scaffold biomaterial may be immersed in a hydrogel or other gel instead of casting, and then a subtractive production method may be used to obtain a final product.

In this example, a gel is used to combine two or more separate scaffold biomaterial subunits to provide a composite biomaterial structure having a larger and/or more complex structure with tunable characteristics.

In certain embodiments, it is contemplated that structures as described herein, comprising two or more scaffold biomaterial subunits, may overcome and/or improve on certain difficulties associated with larger sizes and corresponding lengthy decellularization times, and/or with diffusion in large constructs. In certain embodiments, structures as described herein may allow for designing of certain structures and features that are not found in nature while exploiting the natural complexity of the source of the scaffold material in the individual subunits. In certain embodiments, structures are described herein may allow for increased complexity in physical and/or mechanical properties (i.e. stress shielding and site specific moduli, channels, pores, etc.). In certain embodiments, structures as described herein may allow for permeability modification through the use of different glues and/or coatings (for example, sealants for vessels, semipermeable membranes, and/or junctions). In certain embodiments, structures as described herein may provide for tunable mechanical properties and/or junctions, based on the glue or coating used (i.e. varying the Young's modulus). In certain embodiments, structures as described herein may be articulated structures, which may confer varying degrees of flexibility and movement (i.e. ring stack blood vessel) as desired. In certain embodiments, suitable drugs, signalling molecules, growth factors, metabolites, and/or ECM proteins and/or components may be added to structures as described herein for providing desired responses which may be general or cell/tissue type specific, and/or which may be positive or inhibitory as appropriate for the particular application. In certain embodiments, scaffolds as described herein may be loaded or functionalized with a drug, and used to administer the drug thereby providing for at least some site specific drug delivery, which in certain embodiments may lower dosage and/or increase efficiency of the drug.

In certain embodiments, structures as described herein may provide for time-dependent and/or time-independent release of one or more agents, which may be achieved by loading the agent(s) in a hydrogel, or other gel, with varying release properties used on the scaffold biomaterial subunits, and/or by covalently binding the agent(s) to the scaffold biomaterial(s) with a suitable chemical functionalization method. In certain embodiments, structures as described herein may be vessels containing the agent(s), which may be packed into the vessels that are covalently linked through linker molecules such as succinic acid (i.e. in certain embodiments, temporary or permanent cues may be added to guide desired outcomes, for example agent(s) may be added to promote endothelial growth, while other agents may be added to reduce clotting and/or inflammation, for example). These vessels may be oriented in site specific locations, and may have time specific release properties. In certain embodiments, such chemical modification may allow for steric hindrance difficulties to be reduced or resolved, and/or may allow for increased complexity of site specific modifications. In certain embodiments, linker molecules may be used to mediate connections to drugs, signalling molecules, growth factors, metabolites, ECM proteins and components, etc., as well as vessels containing such compounds, or any combinations thereof.

Sterics may present difficulties in certain circumstances. For example, different cell attachment densities may lead to different cell responses in the absence of any other biochemical or biophysical modification or signalling. In certain embodiments of the structures described herein, the degree of substitution may now be tuned to suite specific functions, for example.

In certain embodiments, structures as described herein may be for use in complex tissue design, as biomaterial implants for tissue repair/regeneration, for drug delivery, for growth factor incorporation, or any combinations thereof.

In certain embodiments, structures as described herein may be for use in non-therapeutic type applications such as in articulating parts for synthetic biorobotics, and/or in electrical circuitry integration.

In certain embodiments, materials as described herein may be suitable for 3D printing of biomaterial in gel and/or paste form. By way of example, if carboxymethyl and hydroxyl ethyl groups are present, a gel or paste may be crosslinked with chemical crosslinker (i.e citric acid, glutaraldehyde, etc.) and temperature. Dissolution of the biomaterial with polar solvent (i.e. dimethylacetamide/LiCl) follow by a reconstruction (via casting, printing or molding) with evaporation, dilution or leeching of the solvent may be performed. Multiple applications such as 3D printing, injectable hydrogels, moulds, and glues are contemplated, for example.

Example 2—Composite Interlocking Biomaterials

In this example, different scaffold biomaterial subunits were combined via shape-based interlocking. Geometry of the subunits was used to hold the assembled structure together. Although a wide varied of interlocking geometries are contemplated, this example mainly used a peg-and-hole type interlocking similar to that of Lego blocks. By interlocking, customization of shape and/or structure may be achieved, and larger macro structures may be provided having varied degrees of flexibility and articulation, as desired for the particular application.

3D biocompatible scaffolds consisting of decellularized plant tissue have been developed. These biomaterials may support cell growth, invasion, and/or proliferation in vitro and in vivo. As described, composite materials of cellulose scaffolds and hydrogels have been developed, where the presence of the hydrogel may allow for distinct biochemical and physical cues to be temporarily or permanently introduced. The cellulose scaffolding may be an attractive base material because of its high biocompatibility, natural abundance, simple production, low cost, and/or complex structures. Plants have evolved to produce complex specialized structures. Remarkably, many of these structures are related to those found in the human body. Creating composite materials comprising these plant structures may create biomimetic materials for tissue engineering. In certain embodiments, preparing larger sizes may create difficulties due to size of the source materials. Accordingly, composite plant-based materials may be a solution to size limitations imposed by nature. Multicomponent systems may be used to retain features of the source material, but expand the configurability though designing materials with different chemical and/or physical environments, for example. By way of example, a composite material may be designed to have regions with different porosities and/or mechanics, while maintaining the intricate features of the source plant structures. An example of a direct result of using materials with different mechanical properties is the phenomenon of stress shielding. Stress shielding may occur in the body and may be a key issue with bone implants. Inadequate or abundant stress shielding may result in damage or degradation of the surrounding healthy tissue. Further, the interfaces between different tissues often separate regions of radically different microenvironments. By designing composite materials, interfaces of different cell populations and environments may be mimicked.

In these studies, scaffold biomaterial was first carved into subunits of desired shapes using a CNC to provide for precision and reproducibility. The desired shapes were then removed from the bulk material by slicing on a mandolin slicer. The thickness of the mandolin slice was used to set the z thickness of the material. Subsequently, the scaffold biomaterial subunits were decellularized and sterilized, see WO2017/136950, entitled "Decellularised Cell Wall Structures from Plants and Fungus and Use Thereof as Scaffold Materials", herein incorporated by reference in its entirety. The material was then ready for cell culture and/or implantation, and was readily assembled into the final structure by pressing the subunits together using tweezers.

This example investigates creating composite cellulose-based, plant-derived scaffolds. The scaffolds were combined by geometry alone, without the use of external agents such as glues, crosslinkers, and hydrogels (although any or all of these may also be used in combination with the present geometry constructs). These interlocking composites present an appealing approach to biomaterial design. The results of this example show that a complex biomaterial may be assembled from subunits in a manner similar to that of assembling Lego. Cells may invade the scaffolds, and may cross the subunit interfaces. Moreover, the cells may integrate the distinct subunits through matrix deposition, and cell migration may be impeded with the presence of existing cells on adjacent scaffolds, for example. The composite materials demonstrated stress shielding, supported the growth of different cell types, and created interfaces between distinct tissues. The present approaches may be appealing for creating larger and/or more complex composites, for example.

Materials and Methods

Scaffold production: McIntosh Red apples (Canada Fancy) were cut to create two flat parallel faces. The apple was cut into peg (5 mm×5 mm×2 mm with a 2 mm peg extending from the centre) and hole (5 mm×5 mm×2 mm with a 2 mm diameter hole in the centre) Lego-style pieces with a Carbide 3D Shapeoko 3 CNC machine and the Chilipeppr jpadie software. The scaffolds were cut at a speed of 1 mm/s with a 0.8 mm diameter drill bit and an angle of 180°. The subunits were designed using Inkscape and were converted into the gcode using Jscut. The samples were removed from the bulk apple tissue by inverting and slicing on a Mandolin slicer set to the appropriate thickness (4 mm for the pegs and 2 mm for the holes). The samples were transferred to a 0.1% SDS solution and decellularized for 72 h while being shaken at 180 RPM. After decellularization, the samples were washed three times with $dH_2O$. Next, the subunits were incubated in 100 mM $CaCl_2$ for 24 h at room temperature to remove any surfactant residue. The samples were washed three times with $dH_2O$ to remove the salt residue, and then they were incubated with 70% ethanol for sterilization. After the removal of the ethanol, three washes with $dH_2O$ were performed to yield a sterile scaffold, free of contaminants. For the stress shielding experiments, carrots were cut into the hole subunit shapes as described above.

Cell culture: GFP NIH 3T3 mouse fibroblasts, NIH 3T3 mouse fibroblasts, and MC 3T3 E1 subclone 4 preosteoblasts were maintained at 37° C. and 5% $CO_2$. The GFP 3T3s and 3T3s cells were cultured in Delbecco's Modified Eagle Medium-High Glucose (DMEM) supplemented with 10% fetal bovine serum and 1% penicillin/streptomycin (100 U/mL and 100 μg/mL respectively) (Hyclone Laboratories Inc.). The MC 3T3 E1 cells were cultured in Minimum Essential Medium α (MEM α) without ascorbic acid. Serum supplementation and antibiotics were the same as previously mentioned. The cells cultured on cell culture plates were rinsed with phosphate buffered saline, trypsinized, and resuspended in media. The cells were counted and centrifuged in order to separate the cells from the trypsin and the media. The supernatant was aspirated, and the pellet containing $5\times10^4$ cells was resuspended in 25 μL of fresh culture medium. Cells were seeded onto the scaffolds and incubated for 1 h. After 1 h, the culture plate was filled with the appropriate media to submerge the sample. The seeding was repeated after 1 week. The cells were allowed to proliferate and invade the scaffold for 2 weeks prior to subunit assembly and migration analysis. The culture media was replaced every day and the samples were transferred to new culture plates after 1 week of growth.

In the case of the preosteoblast differentiation, the cells proliferated for an additional 3 weeks on the respective subunits before assembly during the differentiation process. The GFP 3T3 cells were maintained in DMEM, while the MC 3T3 E1 cells were cultured in differentiation media (MEM α with 4 mM sodium phosphate dibasic and 50 μg/mL ascorbic acid). The media was changed every day. Subunits were combined and cultured for 1 week prior to mechanical investigation, and fixation and imaging.

Subunit assembly: The complementary peg and hole-type Lego-style pieces/subunits were combined to create a composite unit. The two subunits were assembled by manually pressing them together with tweezers until they clicked into place. For the experiments involving different cell types, the cells were grown on their respective subunits for the 2-week period prior to assembly.

Staining: Biocompatible live cell scaffold staining was used to image the decellularized scaffolds. Two different stains were used to give blue and red scaffolds: Calcofluor White (0.1 mg/mL in media) and Congo Red (0.1 mg/mL in media) respectively. The staining was performed without fixation for the migration experiments. Prior to staining, the cells were washed 3 times with PBS and then fixed with 3.5% paraformaldehyde for 10 minutes for the higher resolution imaging. The cells were stained with 10 μg/mL Hoechst 33342 (Invitrogen), 5 μM of cell tracker red (Thermo Fisher), and 1 M SiR-actin (Spirochrome Cytoskeleton) for 1 hour. The samples were then washed with PBS and mounted in Vecta Shield mounting medium during imaging.

Microscopy: The cells and biomaterials were imaged with epi-fluorescence and laser scanning confocal microscopy. The samples were imaged with a Nikon TiE A1-R high speed resonant scanner confocal microscope with a 4× and 60× objective. ImageJ (Fiji) was used to process the images. Confocal images presented here are maximum intensity projections of confocal volumes as well as 3D reconstructions. Brightness/contrast settings were adjusted to maximize the fluorophore signal; otherwise, no other image manipulations were performed.

Cell migration quantification: Phase contrast images allowed the (x,y) coordinates of the subunits to be recorded on Fiji (ImageJ). The areal coverage of the scaffolds was monitored by the projected area of the GFP 3T3 cells. The confocal images were thresholded using the Fiji (ImageJ) adaptive threshold plugin, and the analyze particles plugin was used to measure the areal coverage of the cells on the subunit of interest bound by the (x.y) coordinates. The ratio of the cell:scaffold area was calculated every week for three weeks post-assembly. The values presented are mean values ±the standard error of the mean (s.e.m.).

Mechanics: The Young's modulus was measured after 2 weeks of culture by compressing the material to a 10% strain, at a strain rate of 50 μm/s, using a custom-built Dynamic Mechanical Analysis (DMA) device and LabVIEW software. The force-indentation curves were converted to stress-strain curves, and they were fitted in Origin 8.5 to calculate the Young's modulus. In addition, stress shielding was studied by compressing the Lego blocks parallel and perpendicular to the interface of the subunits. For this analysis, a mixed Young's modulus was obtained. The integration strength mediated by cell migration across the interface was investigated with tensile measurements. In the tensile measurements, the biomaterial was secured to the DMA device with Ultra Gel (LePage). The biomaterial was left to adhere to the device for 10 min prior to mechanical testing. The strain rate was identical to the compression device and the force was recorded as the subunits were pulled apart.

Histology: For histological analysis, serial 5 μm thick sections starting 1 mm inside the cellulose scaffold were cut. The sections were stained with Masson's Trichrome. A Zeiss MIRAX MIDI Slide Scanner (Zeiss, Toronto, Canada) with 40× objective was used to image slices for cell infiltration, extracellular matrix deposition, and vascularisation (angiogenesis). The micrographs were analysed with the Pannoramic Viewer (3DHISTECH Ltd., Budapest, Hungary) software.

Statistical analysis: In order to assess statistical differences between the cells cultured on the biomaterials under the different conditions, one-way ANOVA tests were used. The Tukey post hoc analysis was performed to determine the statistical difference between the individual samples. For the comparison of more than two samples, the one-way ANOVA was used instead of multiple Student's t-tests to reduce the risk of type 1 statistical errors. When only two samples were compared, the Student's t-test was used. All values presented are the mean±the standard error of the mean (s.e.m.). Statistical significance (indicated by an asterisk) refers to $P<0.05$.

Figure 11:
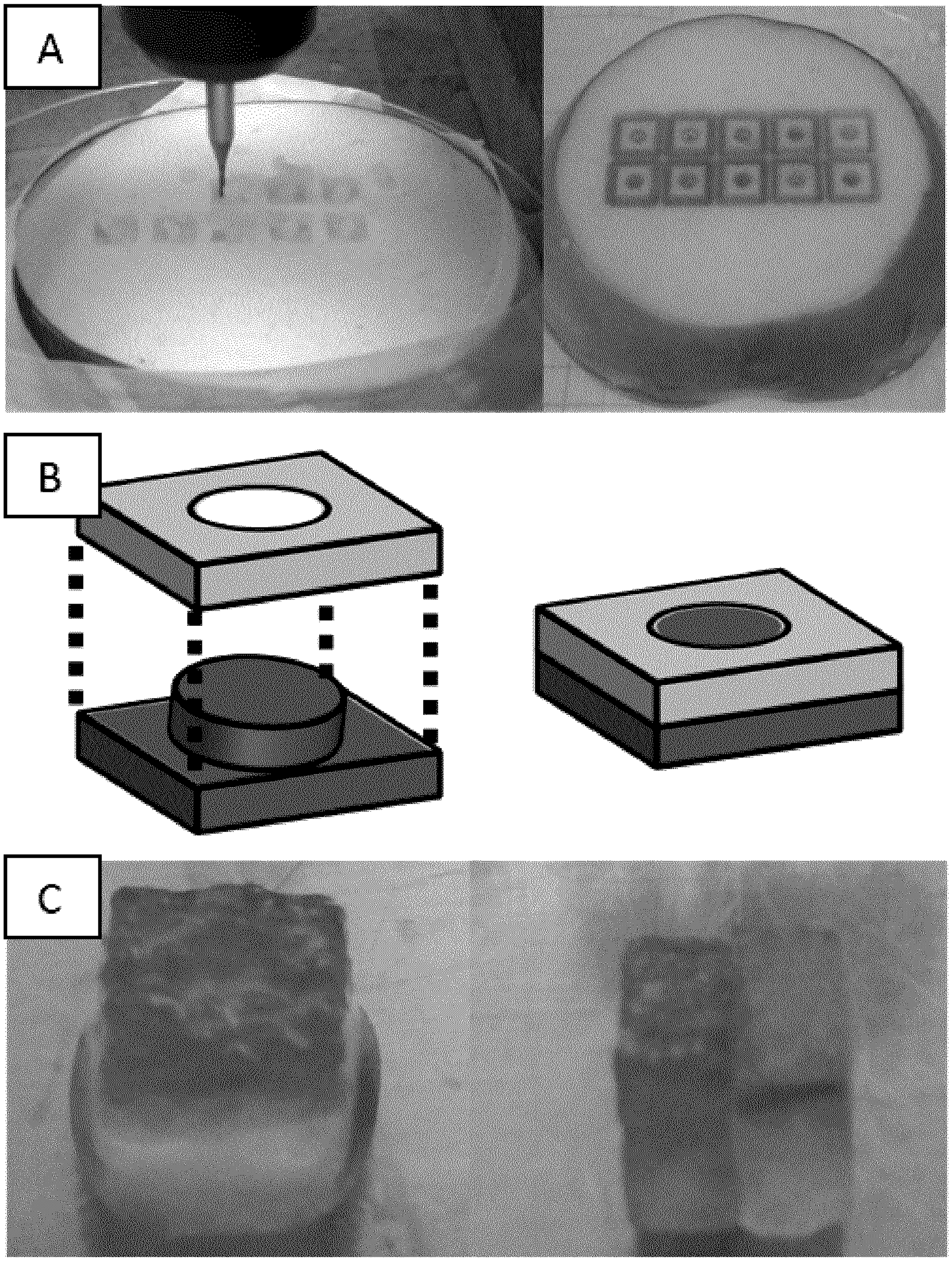
FIG. 11 shows fabrication, models, and products of lego-style subunits. (A) shows CNC cutting, (B) shows a schematic model of subunit assembly, and (C) shows an assembled composite structure comprising the two assembled subunits.

Results and Discussion:

Composite Lego fabrication: In order to create composite biomaterials that were assembled via geometry alone, a proof of concept Lego-style subunit block was designed. The fabrication of such shapes was a relatively slow process using a hand carving technique. Computer Numerical Control router cutting (CNC) was therefore preferred for providing reproducible materials in several minutes. Complementary "peg" and "hole" subunit Lego-style pieces were carved out of apple hypanthium tissue (FIG. 11). This resultant material was decellularized, processed, and then repopulated with mammalian cells to form composite biomaterials for tissue engineering and 3D cell culture. The subunits were easy combined manually and clicked into place (FIG. 11). The tight-fitting geometry of the Lego design kept the unit intact throughout weeks of culture and manipulation.

Figure 12:
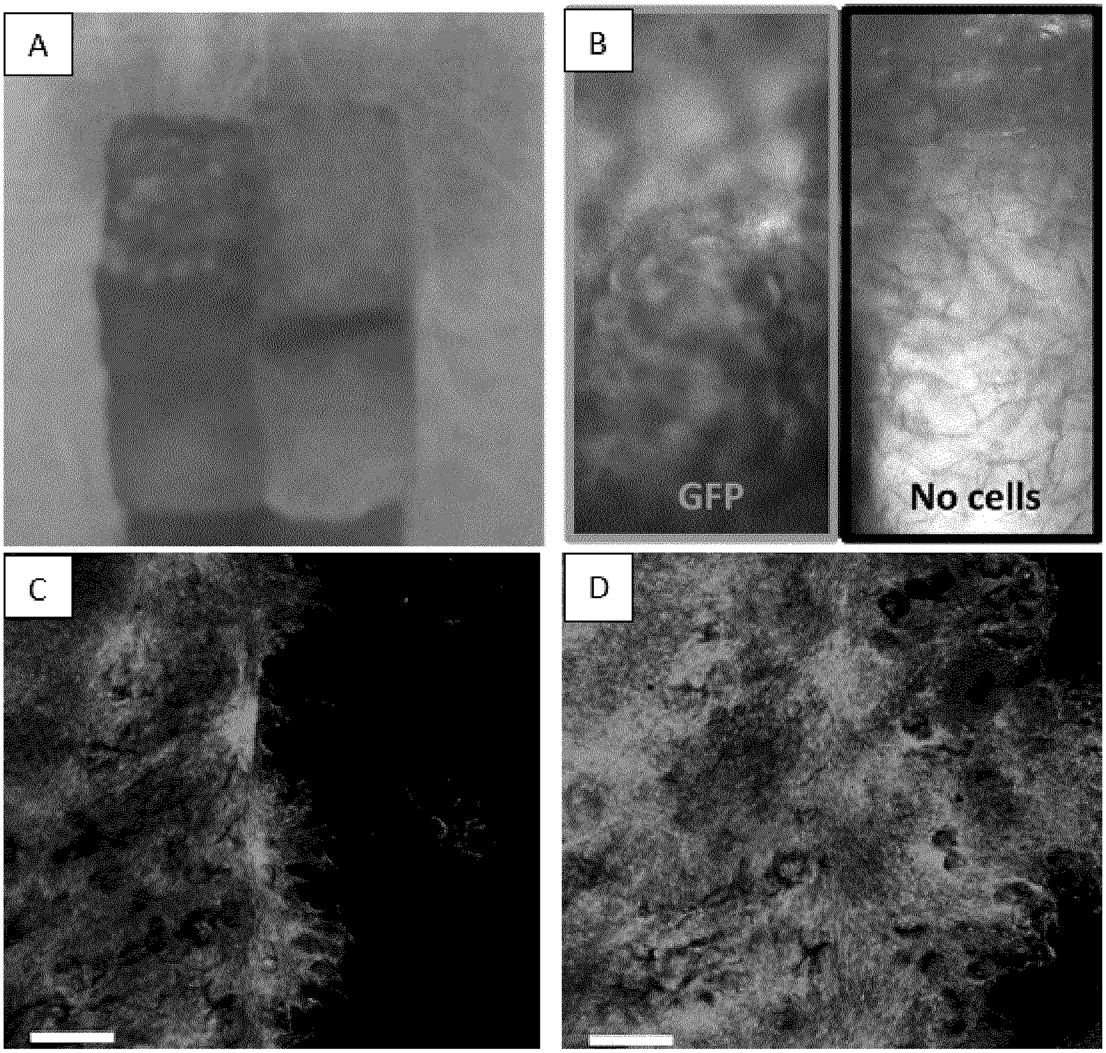
FIG. 12 shows results of single cell-type migration. (A) shows combined peg-and-hole subunits used. (B) shows identification of subunit preloading. (C) shows cell migraction of 3T3 GFP fibroblasts 1-week post-assembly. (D) shows cell migration of 3T3 GFP fibroblasts 3 weeks post-assembly.
Figure 13:
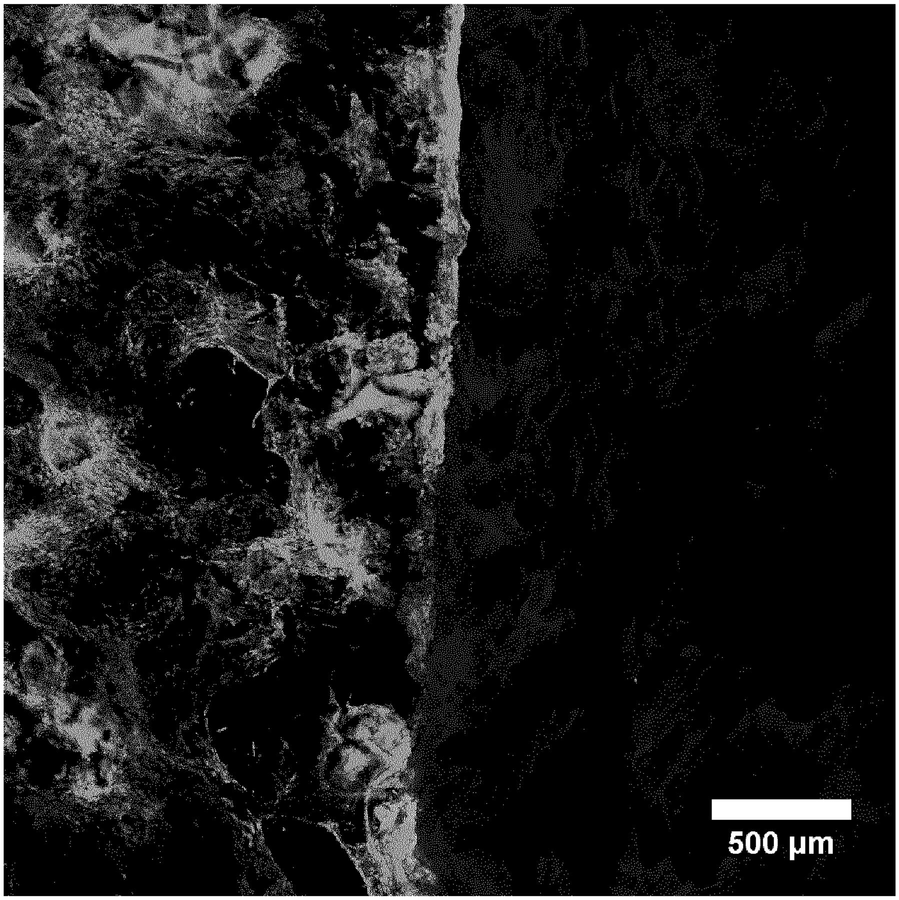
FIG. 13 shows results of dual cell-type migration. Two cell populations were seeded on the two subunits of the composite (green=GFP 3T3 cells, blue=3T3 cells stained with Heochst. The subunits were then combined (T=0)

Cell migration across composites: In order to assess the migration of cells across the interface between the two subunits of the composite material, single cell type migration and dual cell type migration studies were performed. In the single cell type migration assay, GFP 3T3 cells were loaded on one subunit and proliferated and invaded the scaffold for 2 weeks, while the second subunit remained bare. Upon interlocking the material, the cell coverage of the bare scaffold was monitored every week for three weeks with confocal microscopy (FIG. 12). Conversely, in the dual cell type assay, 3T3 fibroblasts (void of GFP) were seeded onto the complimentary subunit, and the experiment was repeated to investigate the effect of the presence of existing cells on the migration profile (FIG. 13).

Figure 14:
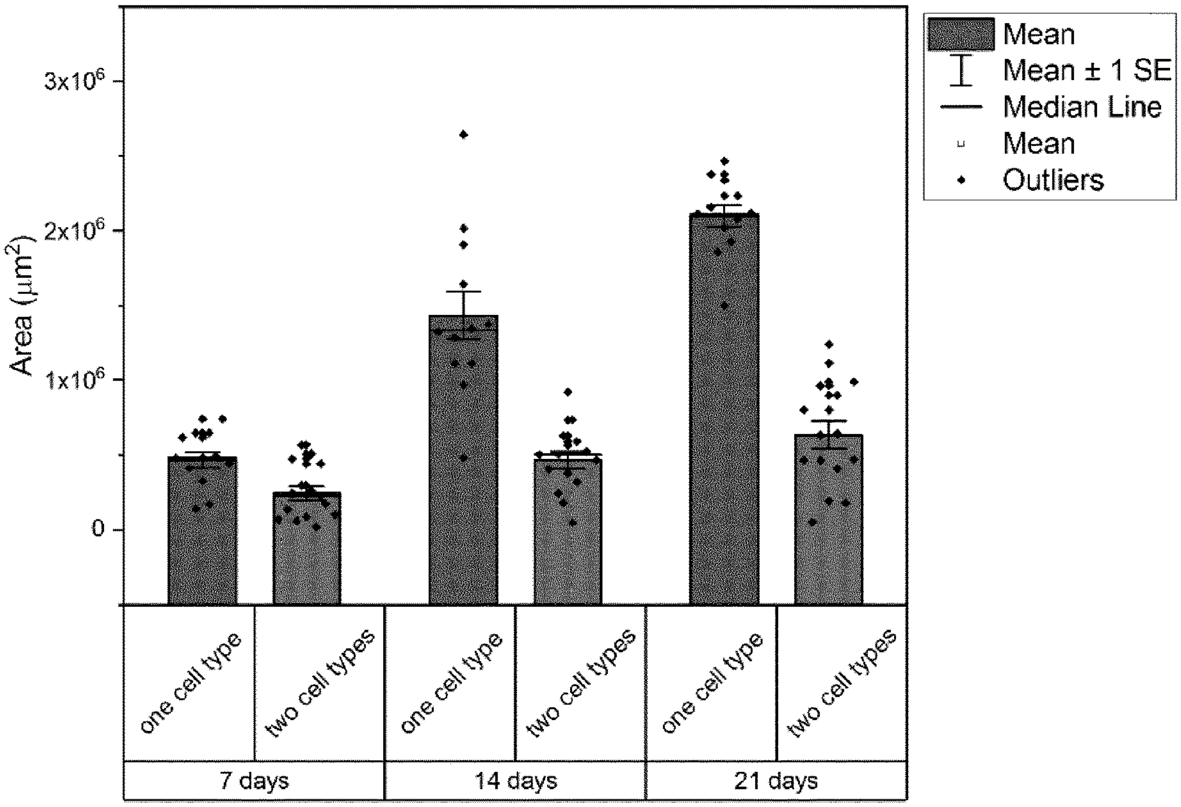
FIG. 14 shows cell area coverage in migration assays of single and dual cell-type migrations. The cell area coverage of the adjacent scaffold measured after 7, 14, and 21 days post assembly.

The result of the single cell type migration was a rapid increase in cell coverage on the bare scaffold (FIG. 12, FIG. 14). After, 3 weeks, the area coverage was comparable to that of the preloaded subunit. As a result, it was shown that the cells were able to transverse the interface and invade and proliferate on the adjacent biomaterial.

In the dual cell type migration experiments, the cell area coverage increased; however, the coverage was much less than that observed in the single cell type migration. The presence of the cells on the second subunit impeded cell migration (FIG. 13). The composite biomaterial allowed for two distinct populations of cells to interact and integrate. The cell types chosen in this study were contact-inhibited. Therefore, the two populations had a minor degree of intermixing, but also largely remained as two distinct groups (FIG. 14).

Figure 15:
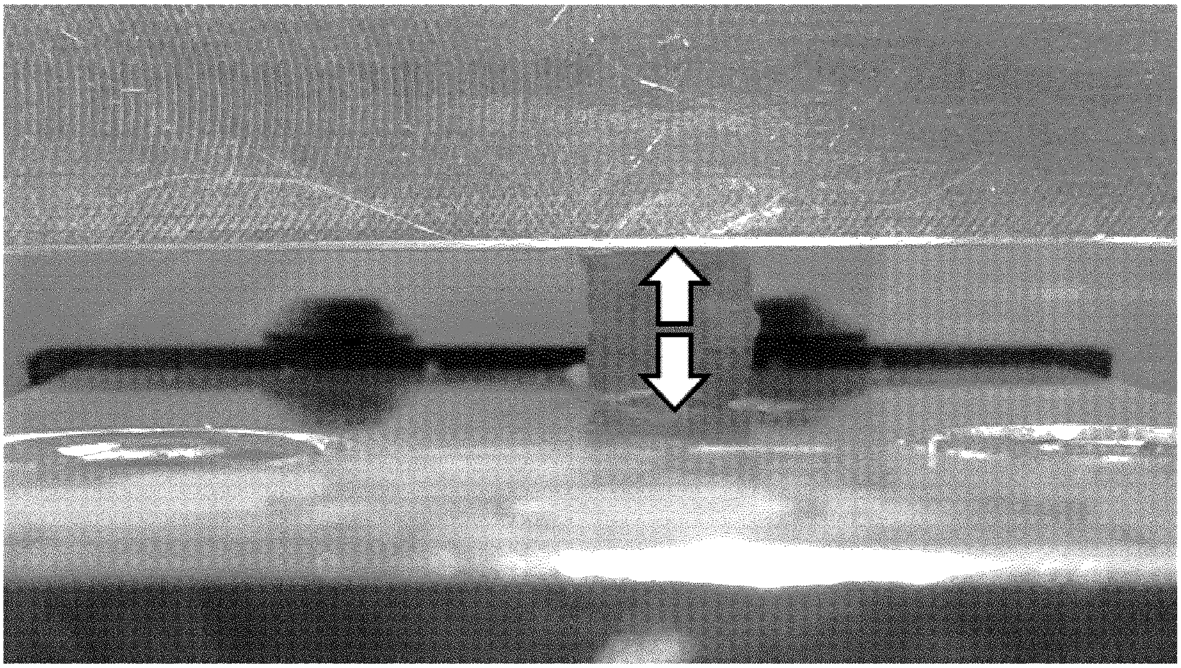
FIG. 15 shows tensile testing of apple interlocking composite. The combined piece was disassembled by pulling the two subunits apart. The force for separation was recorded.

Integration of click (interlocking) biomaterials: The migration studies above clearly showed that the cells migrated from one subunit to another when appropriate structures were used. As confirmed by histological analysis, the cells lay down ECM proteins as they invade and proliferate in the scaffolds. This migration and ECM deposition led to the integration of the two subunits. The Lego-like peg-and-hole design held the unit together through the friction of the tight-fitting geometry. In order to assess whether the presence of the cells resulted in a stronger integration of the subunits, the force required for the composite disassembly was measured. The measurement was carried out on a custom made dynamic mechanical analysis (DMA) device. The top and bottoms of the samples were glued to the parallel plate of the DMA device. The presence of cells resulted in greater tensile forces required to separate the subunits compared to the bare scaffolds void of cells. Consequently, cell invasion and migration across the interface fortified the composite unit in these studies (see FIG. 15).

Stress Shielding and Mechanics: The phenomenon of stress shielding is the difference in the force applied to each body in a composite system. The different elastic moduli of the components may result in different strains and stresses for each part of the system. An effective Young's modulus for the composite may be obtained from the geometry, direction of applied force, and/or the moduli of the constituents. A direct result of this phenomenon is an ability to have an effective Young's modulus that may be dependent on the direction of the applied force. The click/interlocking biomaterials described herein may allow stress shielding to occur by choosing source materials with different elastic properties. The design used in this example showed that applying the stress parallel or perpendicular to the plane of the interface yielded different effective moduli (see FIG. 16). To examine this concept, the two subunits were selected to have different elastic moduli. The two source materials were apple and carrot. Upon combination, the effective Young's modulus depended on the direction of the applied force and yielded a stress shielding biomaterial (see FIG. 16). The model ignored viscous effects of the media within the constructs and treated them as two elastic bodies for simplicity in this testing.

Figure 17:
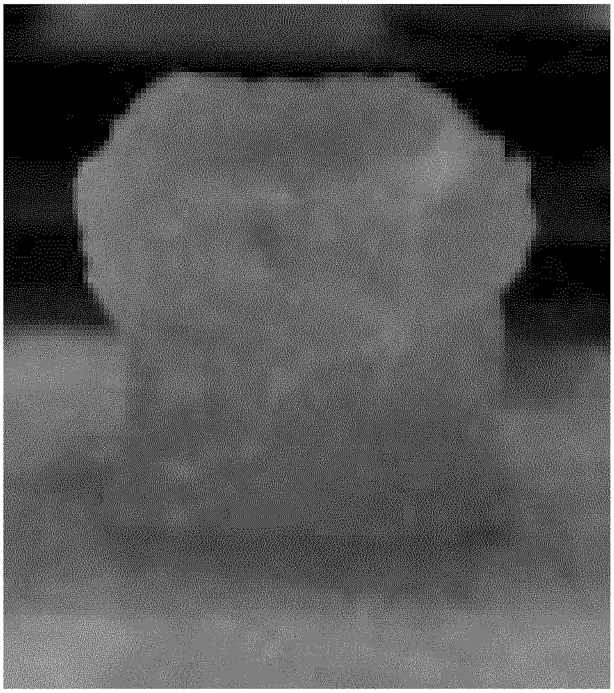
FIG. 17 shows a bone-fibroblast composite structure. Assembled interlocking Lego-style unit seeded with differentiated bone MC3T3 E1 subclone 4 cells (top) and GFP3T3 fibroblasts (bottom) is shown. The calcified scaffold can be seen in the top section. The bottom unit does not have calcium deposits.

Tissue Interfaces: As the migration, integration, and stress shielding results support, composite material comprising different tissue types may be fabricated. Here, MC 3T3 E1 subclone 4 cells were grown on one subunit for 2 weeks. The preosteoblasts differentiated in MEM α containing ascorbic acid and inorganic phosphate for 3 weeks. Calcium and collagen matrix deposition were observed on the scaffold. Subsequently, the biomaterial was combined with a complementary Lego-style subunit loaded with GFP 3T3 fibroblasts. Effectively, a bone-fibroblast tissue interface was created. The cells migrated across the interface as previously observed in the single tissue type investigation. In addition, the preosteoblast differentiation led to an increase in the modulus of the material. Resultantly, the two subunits had different elastic moduli; stress shielding applied to the bone-fibroblast composite. Thus, stress shielding was obtained both via different source materials for the subunits and by using different cell types to create distinct tissues. Here the choice of bone and fibroblast cells was made. This study supports that interlocking composite materials comprising different cell types and tissues may be fabricated with predefined interfaces (see FIG. 17).

The use of composite materials is appealing for designing biomaterials that mimic the natural environment of the cell or tissue. Different strategies have been used to integrate different components of the natural cellular milieu. The different constituents may be combined with crosslinkers, hydrogels, glues, and/or chemical modifications, for example. In many instances, it may be desirable to create composite biomaterials without using these secondary components; therefore, the present example developed an approach for creating composite materials that join together without need for secondary elements. In this example, interlocking "click" biomaterials were designed based on geometry alone. The geometry used was a peg-and-hole Lego-style block design. Using as CNC milling machine, reproducible and rapid cuts were made for a relatively high throughput production of the subunits. The tight-fitting geometry was sufficient to keep the unit intact over several weeks and through manual manipulation and handling.

The subunits were derived from decellularized plant tissue. The complexity and diversity of plant structure is well-suited to biomaterials. Although the organisms are in separate kingdoms, plant structures may be processed and matched to particular structures in the animal or human body. This class of biomaterials is highly biocompatible, tunable, and customizable. In vivo, angiogenesis has been observed in the absence of templating or preloading external agents such as growth factors. Likewise, cells may invade and proliferate in the scaffold in vitro and in vivo. Matrix deposition and a normal minimal immune response may be observed. The base structure of the material is typically cellulose; the chemical linkage of the glucose subunits results in a permanent scaffold that does not degrade to a significant extent in the body. These features, combined with the ability to tune chemical and physical properties, relatively cost-effective production, and the abundance of source materials make these biomaterials appealing for tissue engineering. The interlocking biomaterial method may allow for complex structures and products to be created that are not normally be found in nature. Of particular note, different structures derived from different plants or plant structures may be combined to produce materials with different sizes, mechanical properties, surface chemistries, porosities, and/or degradation rates.

In this study, the migration of cells across the interface between the two subunits of the composite material was investigated, to examine how the cells would respond to the interface between the two components. Both single cell type migration and dual cell type migration studies were performed. In the single cell type migration assay, one subunit was loaded with GFP 3T3 cells and combined with a bare scaffold. The cells crossed the interface, invaded, and proliferated on the bare scaffold. A rapid increase in cell area coverage was observed on the bare scaffold. After 3 weeks the second subunit had comparable coverage to that of the preloaded scaffold. A major implication of those findings is in wound healing. In the present study, the collective cell migration was 3-dimensional. 3D collective migration has shown to be different than 2D surface migrations. These results support use of composite cellulose-based biomaterials in wound healing; and further supports that in general, cells may be able to move from one unit to another and fill the secondary structure without the use of additional agents to mediate the migration across the interface. Conversely, the experiment was repeated using two subunits preloaded with two distinct cell populations. The results show that the cells migrate from one subunit to the other; however, the coverage was much less than that observed in the single cell type migration. The cell types used here were contact inhibited cells. Therefore, the preloading of the scaffold effectively prevented extensive migration onto the adjacent scaffold. The composite biomaterial allowed for two distinct populations of cells to interact and integrate at the interface, and the choice of the contact inhibited cell types reveals that composite materials may be used to create tissue interfaces separating two distinct groups of cells. In other applications, using cells that are not contact inhibited is also contemplated to create regions of overlapping cells and varying degrees of intermixing of cell types for particular tissue of interest.

The tight-fitting geometry of the interlocking design used in this example adequately kept the pieces together in one unit. The force required to separate the materials was investigated. The measurements were then repeated on scaffolds with cells. As discussed, the cells transversed the interface and invaded the neighbouring scaffold. Hence, there was a degree of integration of the two subunits by the cells and the ECM they deposit. The integration of the subunits by the cells resulted in higher tensile forces required to separate the units. This supports a variety of tissue engineering applications. These results show there was a fortification of the composite material interface as cells invaded the material. In regenerative medicine and medical applications involving biomaterials, tissue integration is of key interest. For example, in bone implants, the lack of tissue integration may result in loose implants that may eventually fail as a consequence of damage to the surrounding tissue and debris formation.

Similarly, stress shielding is of key interest in bone implants. The typical materials that have been used used have stiffnesses that greatly exceeds that of the native bone tissue. Previous approaches are often far from ideal; however, they are used as the alternative materials typically lack the mechanical properties two withstand the loads exerted on the bones. Stress shielding may result in the degradation of the surrounding healthy bone tissue by osteoclast resorption. In the absence of stress, the osteoclasts are signaled to resorb bone tissue. This lack of stress may occur via the shielding of the implant with a higher elastic modulus. Stress shielding has been identified as a key challenge in bone implants and bone tissue engineering. Nevertheless, it occurs throughout other tissues as well. For tissue interfaces stress shielding is present; thus, proper mimicking of the stress shielding is desirable for recreating certain microenvironments. The interlocking biomaterials approach as described herein may allow stress shielding to targeted and materials may be created with particular effective moduli. In this example, viscous effects of the media within the constructs were ignored and this study treated them as two elastic bodies for simplicity.

An appealing application for a composite biomaterial product with different cell types and/or mechanical properties may be the bone-fibroblast tissue interface. This example shows preosteoblasts may be differentiated on the apple-derived scaffolds and combined with a secondary scaffold loaded with fibroblasts. In this example, the bone tissue exhibited calcium and collagen matrix deposition. At the interface, the cells migrated across the interface and integrated the two tissues. In addition, the preosteoblast differentiation led to an increase in the modulus of the material. Accordingly, the bone-fibroblast composite produced displayed stress shielding. This investigation demonstrates that complex entities may be produced. The biomaterials may have different cell types and/or mechanical profiles. This concept may be extended to, or combined with, chemical modifications and/or further modifications with hydrogels and/or crosslinkers, for example, but this approach is not dependent on such additional factors to remain structurally intact. Interestingly, this approach may allow customized interfaces to be designed.

In this example, composite cellulose-based, plant-derived scaffolds were successfully combined by geometry alone, without the use of external agents such as glues, crosslinkers, and hydrogels. Interlocking subunits provides an attractive approach to biomaterial design as it may reduce demand for additional elements. The click biomaterials presented herein have a Lego-style design. The materials in this example supported cell growth and migration across interfaces and integration of the distinct subunits through matrix deposition. Cell migration was impeded with the presence of existing cells on adjacent scaffolds. The composite materials had the ability demonstrate stress shielding when the moduli of the subunits were different. It was also demonstrated that bone-fibroblast composites and interfaces may be created. The biomaterial interlocking composite approach shown here may provide for creating complex composite materials that more closely mimick the native in vivo environment.

Figure 2:
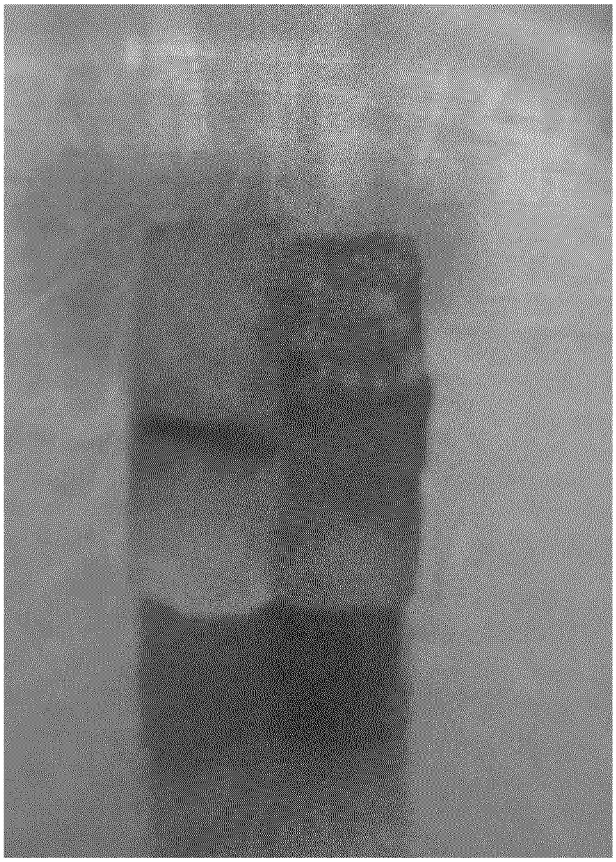
FIG. 2 shows interlocked cellulose-based biomaterials. A block may be assembled using a Lego-style peg-and-hole geometry, as shown. The tight-fitting subunits may be assembled/combined to provide a biocompatible intact structure.

FIG. 2 shows an image of an assembled structure comprising two subunits interlocked together. FIG. 2 shows interlocked cellulose-based biomaterials, wherein a block may be assembled using a Lego-style peg-and-hole geometry, as shown. The tight-fitting subunits may be assembled/combined to provide a biocompatible intact structure Using the interlocking approach described herein, it is contemplated that structures as described herein, comprising two or more scaffold biomaterial subunits, may overcome and/or improve on certain difficulties associated with larger sizes and corresponding lengthy decellularization times, and/or with diffusion in large constructs. In certain embodiments, structures as described herein may allow for designing of certain structures and features that are not found in nature while exploiting the natural complexity of the source of the scaffold material in the individual subunits. In certain embodiments, structures are described herein may allow for increased complexity in physical and/or mechanical properties (i.e. stress shielding and site specific moduli, channels, pores, etc.). In certain embodiments, structures as described herein may be articulated structures, which may confer varying degrees of flexibility and movement as desired. In certain embodiments, structures as described herein may allow for combination of different cell types in different regions.

In certain embodiments, gluing, hydrogel (or other gel) casting, coating, cross-linking, and/or pasting may be used to further secure and/or hold the subunit(s) together in the structure.

In certain embodiments, suitable drugs, signalling molecules, growth factors, metabolites, and/or ECM proteins and/or components may be added (i.e. functionalized or loaded on and/or in) to structures as described herein for providing desired responses which may be general or cell/tissue type specific, and/or which may be positive or inhibitory as appropriate for the particular application. In certain embodiments, scaffolds as described herein may be loaded or functionalized with a drug, and used to administer the drug thereby providing for at least some site specific drug delivery, which in certain embodiments may lower dosage and/or increase efficiency of the drug. In certain embodiments, structures as described herein may provide for time-dependent and/or time-independent release of one or more agents such as suitable drugs, signalling molecules, growth factors, metabolites, and/or ECM proteins and/or components.

In certain embodiments, scaffold biomaterials as described herein may be cellulose-based, hemicellulose-based, chitin-based, chitosan-based, pectin-based, lignin-based, lignan-based, or any combinations thereof. In certain embodiments, composite structures as described herein may be tunable with respect to their biochemical, biophysical, and/or mechanical properties.

In certain embodiments, it is contemplated that structures as described herein may be for use in custom in vitro 3D cell culture devices; in vivo applications and/or fundamental research; complex tissue design; biomaterial implants for tissue repair and/or regeneration; medical devices such as devices or implants for bone, connective tissue, skin, muscle, nerve, and/or interfaces; complex tissue repair and/or replacement; membranes and/or filters (for example, artificial kidneys and/or simple biochemistry separation columns); vectors for site specific and time specific drug delivery; increased biocompatibility of existing medical devices through coating or creating composites with materials as described herein; vectors for primary cell culture; cosmetic procedures (for example, implants and/or subdermal topographies); or stents and/or shunts; non-medical applications such as articulating parts for synthetic biorobotics or electrical circuitry integration; or any combinations thereof.

Example 3—Composite Biomaterials of Plant and Bacterial Cellulose

In this example, composite biomaterials comprising both plant and bacterial cellulose are provided. In certain embodiments, guided assembly based biolithography (GAB) techniques may be used to grow bacterial cellulose on decellularized or casted/printed plant cellulose sources to obtain a composite biomaterial with adjustable ratios of cellulose having different crystal structures located in different and configurable regions, and may allow for different microtopographies and densities. In certain embodiments, a bacterial source may deposit cellulose on a plant-derived cellulose-based scaffold biomaterial, for example, with the two different celluloses having different ratios and/or crystal structures. The resulting product may thus comprise different celluloses, which may have different functional chemistries, densities, porosities, and/or mechanical properties. By combining celluloses, the resulting products may provide increased complexity, configurability, and/or additional features over either cellulose alone. In certain embodiments, the manner in which the bacterial cellulose grows on the plant cellulose scaffold may be dictated or affected by geometry of the plant cellulose scaffold, culture conditions, or both. In certain embodiments, the resulting scaffold biomaterials may be customizable with respect to shape and/or structure, and/or may be used to provide macro structures having varying degrees of flexibility and/or articulation.

3D biocompatible scaffolds comprising decellularized plant tissue have been developed, see WO2017/136950, entitled "Decellularised Cell Wall Structures from Plants and Fungus and Use Thereof as Scaffold Materials", herein incorporated by reference in its entirety. These biomaterials may support cell growth, invasion, and proliferation in vitro and in vivo. The cellulose scaffolding may be an attractive base material because of its high biocompatibility, natural abundance, facile production, low cost, and complex structures. Plants have evolved to produce complex specialized structures. Remarkably, many of these structures relate to those found in the human body. Creating composite materials from these plant structures may create biomimetic materials for tissue engineering.

A challenge for such approaches arises when larger size substrates and/or implants are desired. Accordingly, composite plant-based materials may provide a solution to such size challenges imposed by nature. Multicomponent systems may retain the advantages of the plant-derived materials, but expand the potential applications though designing materials with different chemical and/or physical environments. For example, a composite material may be designed to have regions with different porosities and/or mechanics, while maintaining the intricate features of the plant-derived structures. By using materials with different mechanical properties, the phenomenon of stress shielding may be provided. Stress shielding occurs in the body and is a common issue with bone implants. Inadequate or abundant stress shielding may result in damage or degradation of the surrounding healthy tissue. Moreover, the interfaces between different tissues often separate regions of radically different microenvironments. By designing composite materials, interfaces of different cell populations and environments may be mimicked.

In certain embodiments, the present approaches may use guided assembly based biolithography (GAB) techniques. This technique may be used to grow bacterial cellulose on decellularized or casted/printed plant-derived cellulose sources to obtain a composite material with different ratios of cellulose with different crystal structures located in different regions. This technique may also allow for designing different microtopographies and/or densities. The bacterial sources may deposit cellulose on plant-based cellulose scaffolds (or other such scaffolds). The two different sources may have different ratios of crystal structures (cellulose Iα/β for example). As a result, the celluloses may have different functional chemistries, densities, porosities, and/or mechanical properties. Using such composites may expand the features of each material. The manner in which the bacterial cellulose grows on the plant cellulose source or scaffold may be at least in part determined by the geometry of the plant cellulose source or scaffold, as well as the culture conditions, for example.

Methods:

Scaffold production: Decellularized material may be prepared according to established protocols, see WO2017/136950, entitled "Decellularised Cell Wall Structures from Plants and Fungus and Use Thereof as Scaffold Materials", herein incorporated by reference in its entirety.

Bacterial cellulose production and (GAB): Several organisms may be used for this task. As per the methods in Bottan, S., Robotti, F., Jayathissa, P., Hegglin, A., Bahamonde, N., Heredia-Guerrero, J. A., et al. (2015). Surface-structured bacterial cellulose with guided assembly-based biolithography (GAB). ACS Nano 9, 206-219, which is herein incorporated by reference in its entirety. The scaffold biomaterial, which may be decellularized, may serve as the templating structure, thereby combining two different types of celluloses from two different sources in the resulting composites.

In certain embodiments, there is provided herein scaffold biomaterials comprising both plant-derived (or fungal-derived) cellulose and bacterial-derived cellulose. Such constructs may allow for generating structures and features that are not found in nature, while exploiting the natural complexity of the scaffold materials of the individual subunits used in the composite structure. In certain embodiments, it is contemplated that these approaches may allow for more complex and/or tunable physical and/or mechanical properties (i.e. stress shielding and site specific moduli, channels, pores, etc.). In certain embodiments, these approaches may be used to provide scaffold biomaterials allowing for the combination of different cell types in different regions. In certain embodiments, these approaches may provide for combining subunits in applications where simple physical connections are not desirable, inapplicable, or insufficient. In certain embodiments, it is contemplated that these approaches may be used to create seals for flowing liquid and/or creating semipermeable interfaces. In certain embodiments, subunits may be glued, coated, or cast together to provide increased structural integrity using a glue, gel, or paste, such as agarose-, gelatin-, collagen-, and/or hyaluronic acid-based agents, for example.

In certain embodiments, gluing, hydrogel (or other gel) casting, coating, cross-linking, and/or pasting may be used to further secure and/or hold the subunit(s) together in the structure.

In certain embodiments, suitable drugs, signalling molecules, growth factors, metabolites, and/or ECM proteins and/or components may be added (i.e. functionalized or loaded on and/or in) to structures as described herein for providing desired responses which may be general or cell/tissue type specific, and/or which may be positive or inhibitory as appropriate for the particular application. In certain embodiments, scaffolds as described herein may be loaded or functionalized with a drug, and used to administer the drug thereby providing for at least some site specific drug delivery, which in certain embodiments may lower dosage and/or increase efficiency of the drug. In certain embodiments, structures as described herein may provide for time-dependent and/or time-independent release of one or more agents such as suitable drugs, signalling molecules, growth factors, metabolites, and/or ECM proteins and/or components.

In certain embodiments, it is contemplated that time-dependent and/or time-independent release may be provided by loading the agents in a gel with varying release properties, and or covalently binding the agents to the scaffold with via chemical functionalization methods. For example, in certain embodiments vessels containing the agents may be packed into vessels that are covalently linked through linker molecules such as succinic acid. These vessels may be oriented in site specific locations and have time specific release properties. In certain embodiments, chemical modification may allow for steric hindrance to be suitable to allow for increased complexity of site specific modifications. In certain embodiments, linker molecules may be used to mediate connections to drugs, signalling molecules, growth factors, metabolites, ECM proteins and/or components, or any combinations thereof, as well as vessels containing such compounds. Different cell attachment densities may lead to different cell responses in the absence of other biochemical or biophysical modification or signalling, and the present approaches may allow for the degree of substitution to be tuned for specific functions, for example.

In certain embodiments, scaffold biomaterials as described herein may be cellulose-based, hemicellulose-based, chitin-based, chitosan-based, pectin-based, lignin-based, lignan-based, or any combinations thereof. In certain embodiments, composite structures as described herein may be tunable with respect to their biochemical, biophysical, and/or mechanical properties.

In certain embodiments, the scaffold biomaterials described herein may be prepared by using a plant-derived scaffold biomaterial structure as a scaffold and/or guide onto which the bacterial cellulose may be grown or deposited. In other embodiments, bacterial cellulose may be used as a template, or a synthetic source such as plastic may be used as a template. In certain embodiments, guided assembly based biolithography (GAB) may be used, in which a template may be used to transfer topographies to a biomaterial. In certain embodiments of GAB, the template may serve as a guide for the bacterial cellulose to grow onto the biomaterial, providing a composite structure of plant and bacteria derived cellulose with designed topographies and/or densities.

In certain embodiments, scaffold biomaterials as described herein may be functionalized and/or loaded with one or more agents tailored for a desired application. Such agents may include, for example, any one or more of a therapeutic drug, a signalling molecule, a growth factor, a metabolite, an ECM protein or component, or any combinations thereof. In certain embodiments, agents may provide for time-dependent or time-independent release of such agents. In certain embodiments, one or more agents may be covalently bonded, directly or indirectly via a linker, to a cellulose-based, hemicellulose-based, chitin-based, chitosan-based, pectin-based, lignin-based, and/or lignan-based scaffold biomaterial. In certain embodiments, one or more acylation and alkylation-type reactions, or other suitable reactions using sulfur, nitrogen, boron, and/or halide compounds (i.e. thiols, imides, imines, amines, amides, borohydrides, borohydrates, and halides) may be used.

In certain embodiments, it is contemplated that structures as described herein may be designed such that one or more sections of the structure are more or less hydrophobic or hydrophilic versus one or more other sections of the structure. In certain embodiments, it is contemplated that scaffold biomaterials as described herein may be configured for site and/or cell-type specificity using functionalization with suitable attractants and/or deterrents.

Using the approaches described herein, it is contemplated that structures as described herein, comprising plant and bacterial celluloses, may overcome and/or improve on certain difficulties associated with larger sizes and corresponding lengthy decellularization times, and/or with diffusion in large constructs. In certain embodiments, structures as described herein may allow for designing of certain structures and features that are not found in nature while exploiting the natural complexity of the source of the scaffold material in the individual subunits. In certain embodiments, structures are described herein may allow for increased complexity in physical and/or mechanical properties (i.e. stress shielding and site specific moduli, channels, pores, etc.). In certain embodiments, the constructs described herein may allow for modification or adjustment of permeability through use of through use of different glues and/or coatings (i.e. sealants for vessels, semipermeable membranes and junctions). In certain embodiments, the constructs described herein may be tunable with regard to mechanic properties and/or junctions based on use of a glue or coating (i.e. varying the Young's modulus). In certain embodiments, structures as described herein may be articulated structures, which may confer varying degrees of flexibility and movement as desired. In certain embodiments, structures as described herein may allow for combination of different cell types in different regions.

In certain embodiments, scaffold biomaterials as described herein may be for use in complex tissue design and/or biomaterial implants for tissue repair and/or regeneration, in drug delivery, and/or for growth factor incorporation. In certain embodiments, scaffold biomaterials as described herein may be for use in non-medical applications such as articulating parts for synthetic biorobotics or electrical circuitry integration; or any combinations thereof.

Example 4—Crosslinking Plant-Derived Cellulose and Chemical Functionalization In this example, crosslinkable cellulose is derived and produced from plant sources. In embodiments where carboxymethyl and hydroxyl ethyl cellulose are present, a cellulose gel or paste may be crosslinked with citric acid and heat. Carboxymethyl and hydroxyl ethyl cellulose functional groups are generally not found in plant-derived cellulose. Accordingly, functional group addition may be performed. Collagen may be covalently bonded to cellulose in such manner. In this example, using such synthetic strategy, a chemical linker molecule with carboxyl end group(s) may be used to obtain a desired functional group on the cellulose. The introduction of citric acid in the presence of heat may create a cross-link between these functional groups, with a benefit of this approach using a non-toxic crosslinker (i.e. citric acid is a natural metabolite). Such approaches may have applications in 3D printing, injectable hydrogels, moulds, and glues, for example 3D biocompatible scaffolds having been developed comprising decellularized plant tissue. These biomaterials may support cell growth, invasion, and proliferation in vitro and in vivo. Composite materials of cellulose scaffolds and hydrogels have also been investigated. The presence of the hydrogel may allow for distinct biochemical and physical cues to be temporarily or permanently introduced. Cellulose scaffolding is an attractive base material, as it may provide high biocompatibility, natural abundance, simple production, low cost, and/or complex structures. Plant have evolved to produce complex specialized structures. Remarkably, many of these structures are related to those found in the human body. Creating composite materials of these plant structures may create biomimetic materials for tissue engineering, for example Creating implants and/or scaffolds of large size may, however, be difficult due, for example, to size of the source material. Accordingly, composite plant-based materials may provide a solution to the size limitations imposed by nature. Multi-component systems may retain features of the materials, but expand customizability and/or applicability by designing materials with different chemical and/or physical environments. For example, a composite material may be designed to have regions with different porosities and mechanics, while maintaining the intricate features of the plant structures from which they are derived. An example of a direct result of using materials with different mechanical properties is the phenomenon of stress shielding. Stress shielding occurs in the body and is a key issue with bone implants, for example. Inadequate or abundant stress shielding may result in damage or degradation of the surrounding healthy tissue. Moreover, the interfaces between different tissues often separate regions of radically different microenvironments. By designing composite materials, interfaces of different cell populations and environments may be more closely mimicked.

Additionally, it is contemplated that modifications such as gluing, gel casting, chemical functionalization, and/or loading with one or more agents (i.e. drugs, signalling molecules, growth factors, metabolites, etc.) may further expand functionality of scaffolds and biomaterials described herein. By way of example, chemically functionalized and cross-linked materials may allow for designing of certain structures and features that are not found in nature while exploiting the natural complexity of the source material in the individual subunits. Moreover, it may provide for more complicated physical and/or mechanical properties (i.e. stress shielding and site-specific moduli, channels, pores, etc.). Such composites may be used to combine different cell types in different regions, for example. The present approaches may provide an alternative to interlocking, gluing, or gel casting of composites, for example when a more permanent strong covalent linkage is desired. As will be understood, the chemical crosslinking approaches described in this example represent illustrative examples, and a wide variety of suitable alternative chemical crosslinking approaches may also be used. Many other reactions may be used, which may employ different functional groups and/or crosslinkers as appropriate.

Materials and Methods

Scaffold production: Decellularized material may be prepared according to established protocols, see WO2017/136950, entitled "Decellularised Cell Wall Structures from Plants and Fungus and Use Thereof as Scaffold Materials", herein incorporated by reference in its entirety. In certain embodiments, it may be turned into a paste or gel with bleach treatment, basic solvents, and/or physical shearing step(s).

Chemical functionalization: Chemical functionalization of cellulose may be performed according to the methods described in Ribeiro-Viana, R. M., Faria-Tischer, P. C. S., and Tischer, C. A. (2016). Preparation of succinylated cellulose membranes for functionalization purposes. Carbohydr. Polym. 148, 21-28, which is herein incorporated by reference in its entirety.

Briefly, in certain embodiments, cellulose may be succinylated with succinic anhydride. Before reaction, the cellulose-based scaffold biomaterials may be subjected to solvent exchange in order to eliminate excess water. Then, cellulose-based scaffold biomaterials may be immersed in methanol and soaked for about five minutes. The solvent may then be discarded, and the procedure repeated two more times. Then, the cellulose-based scaffold biomaterials may be immersed in dichloromethane and gently soaked for about five minutes. The solvent may be discarded and the same procedure may be repeated two additional times. The succinylated cellulose-based scaffold biomaterials may be prepared by immersing the cellulose into 10 mL of dichloromethane, 174 μL of pyridine and 216 mg of succinic anhydride, performed in a static system. The reaction times may be varied (about 2-24 h), and two different temperatures, 25° C. and reflux, may be used for different experiments. After that time, the reaction may be quenched by adding 2 mL of methanol. Then, the material may be washed three times with water, then ethanol, and finally dried at room temperature.

If coupling to one or more functional components is desired, this may be performed in a flat bottom flask to which are added the succinylated cellulose, 8 mL of anhydrous DMF, 40 mg of 3-(ethyliminomethyleneamino)-N,N-dimethylpropan-1-amine (EDC) and 8 mg of 4-dimethylaminopyridine (DMAP), and mixed. The reaction may be kept at room temperature for one hour. Then, a suitably functionalized functional component may be added, and agitated in a tumbling table for 18 h at room temperature. After that time, the material may be washed three times with water, and finally dried at room temperature.

Citric Acid Crosslinking Chemical functionalization of the cellulose may allow for different functional groups to be covalently linked to the material Linking functional groups such as carboxymethyl cellulose and hydroxyl ethyl cellulose may allow for crosslinking using citric acid and heat. Other crosslinkers may be available and used. This example is intended for illustrative purposes, and may be preferred in certain applications since citric acid is generally non-toxic and is a natural by-product of cellular metabolism.

Citric acid crosslinking may be performed according to the methods described in Raucci, M. Alvarez-Perez, Demitri, C. et al. (2015). Effect of citric acid crosslinking cellulose-based hydrogels on osteogenic differentiation. Journal of Biomedical Materials Research-Part A. 103 (6), 2045-2056, which is herein incorporated by reference in its entirety.

Briefly, two different cellulose derivatives may be prepared and used in the preparation: a sodium salt of carboxymethyl cellulose (CMCNa) and hydroxyl ethyl cellulose (HEC). CMCNa is a cellulose derivative with carboxymethyl groups ($—CH_2—COOH$) bound to some of the hydroxyl groups of the glucopyranose monomers that make up the cellulose backbone. This functional group may be responsible of the high sorption capacity due to the Donnan effect. HEC is a non-ionic polymer that is able to form stable networks with a lower sorption capacity. The samples may be prepared via double esterification crosslinking using citric acid (CA). Briefly, hydrogel samples may be obtained by reacting, in distilled water, CMCNa and HEC with CA (20% [w/w] on polymer weight) as a crosslinking agent, respectively. First, a total polymer concentration of 2% by weight of water may be used for the two cellulose derivatives, by stirring gently at room temperature until a clear solution is obtained. This final solution may be used to mould 10-mm thick samples. Samples may first be pre-dried at 30° C. for 24 h to remove absorbed water and then kept at 80° C. for 12 h for the crosslinking reaction.

In this example, hydrolyzed collagen was covalently attached to modified cellulose, exemplifying reactions relating to the modification of cellulose followed by crosslinking or coupling to the modified cellulose.

Figure 6:
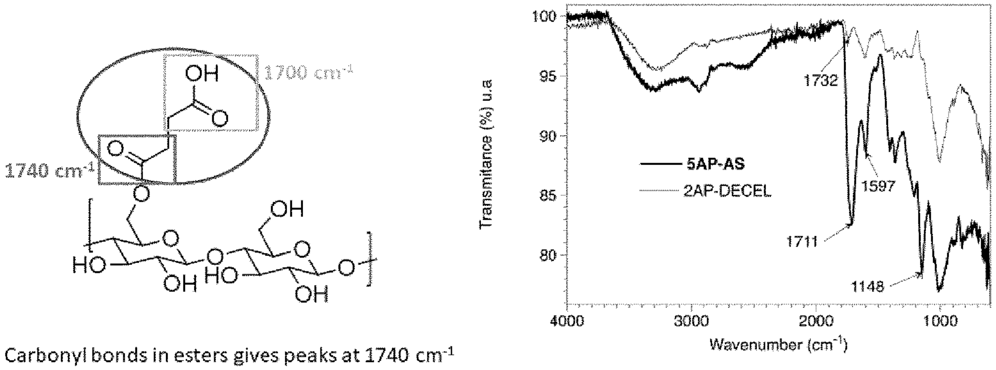
FIG. 6 shows chemical functionalization of cellulose with succinic anhydride. (A) Depiction of the covalent bonding of succinic acid to the cellulose chain along with the absorption bands in the IR spectrum. (B) The IR spectrum of the control (grey) and functionalized (black) scaffolds. The strong absorption peaks near the expected wavenumbers for the ester and carboxyl groups show the successful covalent addition of succinic anhydride to the cellulose chain. Note the shift in wavenumber is due to the neighbouring groups.
Figure 7:
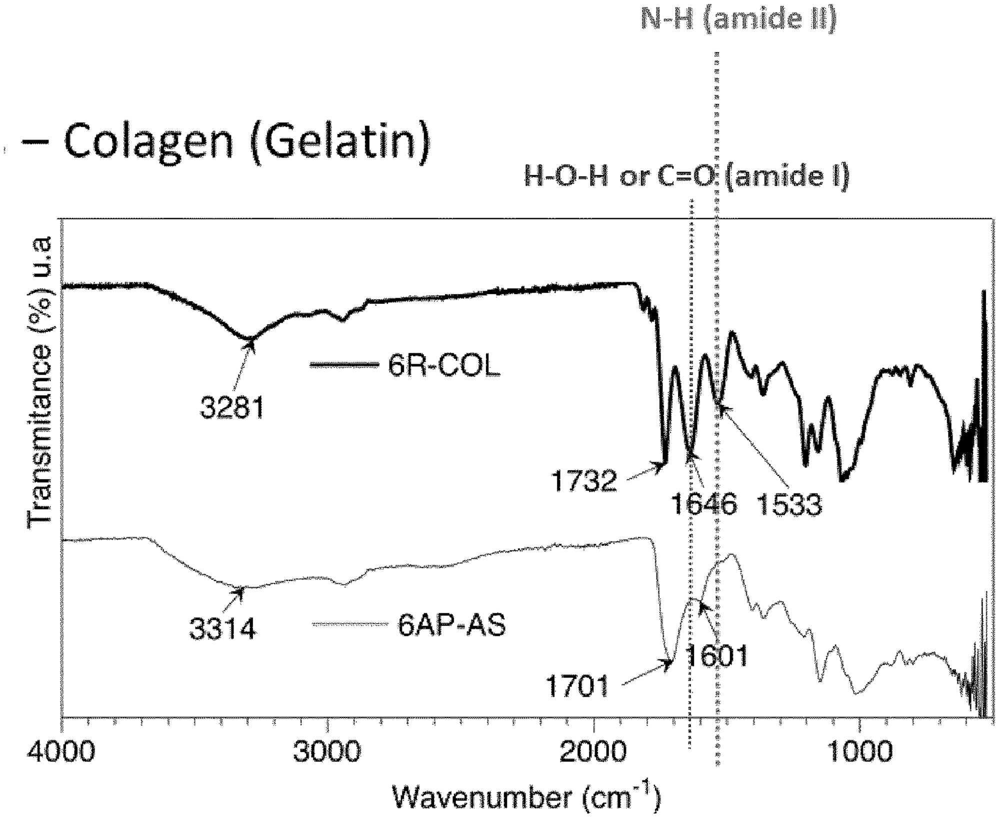
FIG. 7 shows results of chemical functionalization of cellulose with denatured collagen. The IR spectrum of the control (grey) and functionalized (black) scaffolds. The control scaffold was functionalized with the linker molecule of succinic acid, but was void of collagen. The absorption peaks of corresponding to the amide (I and II) bonds show the successful covalent addition of collagen to the cellulose chain via the linker molecule succinic acid.

Results and Discussion:

Succinic acid linker molecules were covalently attached to cellulose as shown in FIG. 6. Hydrolyzed collagen was then covalently attached to the linker groups on the cellulose, as shown in FIG. 7. FIG. 6 shows cellulose with monoesters of succinic acid, where succinic acid was covalently attached to the cellulose. The FTIR spectrum in FIG. 6 shows the carbonyl and carboxylic acid peaks, indicating a successful reaction. The grey spectrum is the control, while the black spectrum is the functionalized scaffold. In FIG. 7, cellulose with hydrolyzed collagen covalently linked is shown. Hydrolyzed collagen was covalently linked to the succinic acid linker molecules. The FTIR spectrum shows the amide peaks indicating a successful reaction. The grey spectrum is the succinated control, while the black spectrum is the functionalized scaffold.

Figure 3:
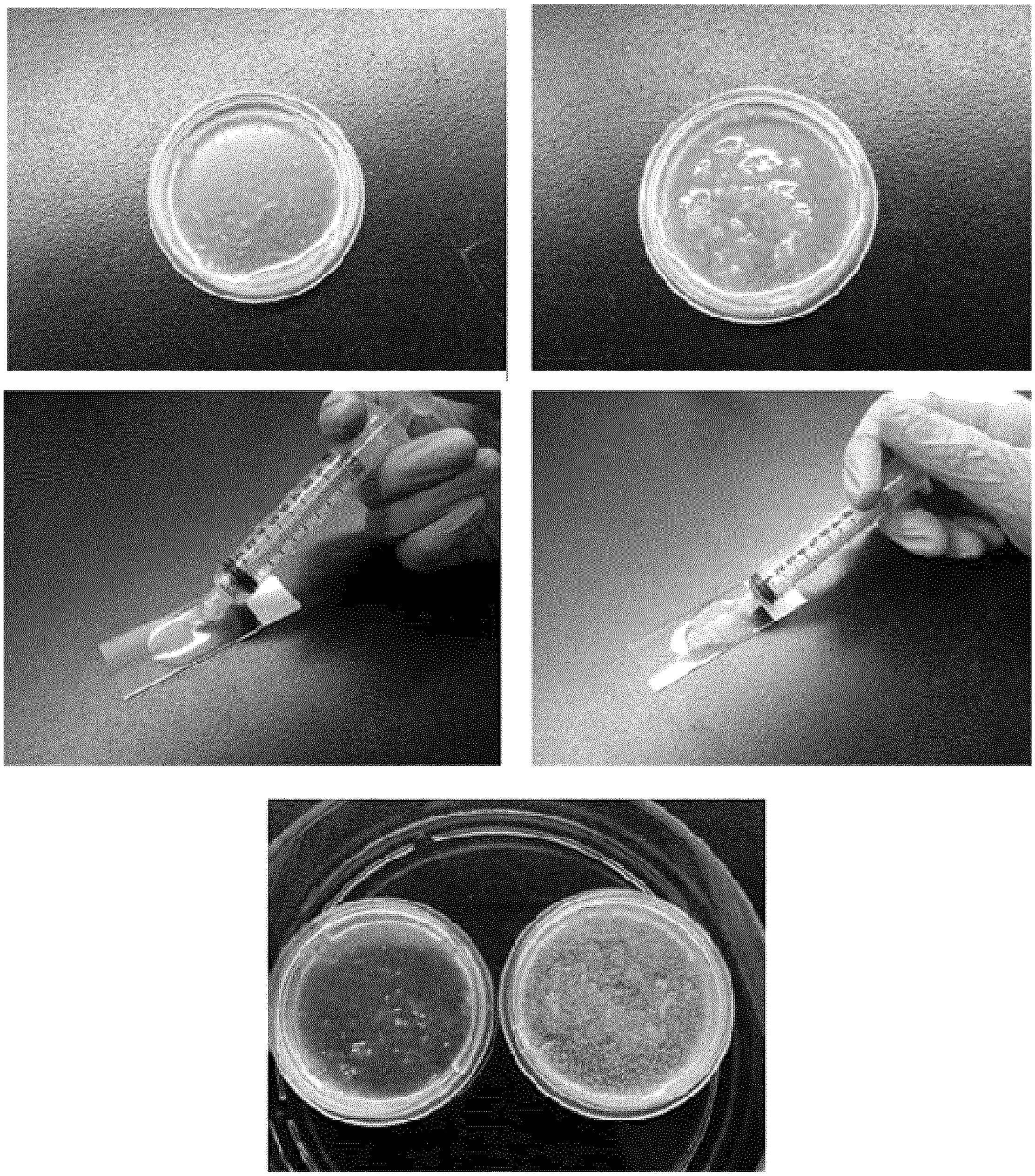
FIG. 3 shows that cellulose-based materials may be crushed into a gel. Different concentrations may have different consistencies (Left=low concentration, right=high concentration). Crosslinking with citric acid and heat may be achieved after chemical modification with carboxymethyl and hydroxyl ethyl groups. Without these groups, crosslinking did not occur. This figure depicts the uncrosslinked hydrogel in the absence of the chemical functional groups after exposure to heat and citric acid.

Without the carboxymethyl cellulose (CMCNa) and hydroxyl ethyl cellulose (HEC), the citric acid treatment did not crosslink manually crushed plant-derived cellulose gel. The cellulose was, however, successfully pressed into a gel/paste as shown in FIG. 3, depicting injectable cellulose gels and pastes showing cellulose may be dehydrated and grinded into a powder form that can then be rehydrated to a desired consistency to produce a gel or a paste. If the cellulose lacks carboxymethyl and hydroxyl ethyl cellulose, it does not crosslink in the presence of citric acid and heat.

This example may provide for crosslinkable cellulose derived from plant sources. If carboxymethyl and hydroxyl ethyl cellulose are present, a cellulose gel or paste may be crosslinked with citric acid and heat. These functional groups (carboxymethyl and hydroxyl ethyl cellulose) are not normally found in plant-derived celluloses. As a result, functional group addition may be performed. This example has successfully covalently bonded collagen to cellulose, supporting the approach proposed herein. The chemical linker molecule with carboxyl end groups may be exploited to obtain the desired functional group(s). The introduction of citric acid in the presence of heat may create a crosslink between these functional groups. An advantage of this approach may be use of a substantially non-toxic crosslinker (citric acid is a natural metabolite). Multiple applications, such as, but not limited to, 3D printing, injectable hydrogels, moulds, and glues are contemplated. Modifications such as gluing, gel casting, chemical functionalization, loading with one or more agents (i.e. drugs, signalling molecules, growth factors, metabolites, etc.) may further expand the functionality of these materials.

Chemically functionalized and crosslinked materials may allow for designing of certain structures and features that are not found in nature while exploiting the natural complexity of the scaffold source material(s) in the individual subunits. Moreover, it may allow for more complicated physical and mechanical properties (i.e. stress shielding and site-specific moduli, channels, pores, etc.). These composites may be used to combine different cell types in different regions. This crosslinking approach may provide an alternative, or a complement, to interlocking, gluing, or gel casted composites when a more permanent and/or strong and/or covalent linkage is required.

The presently described approaches may provide for tunable biochemical, biophysical, and/or mechanical properties of cellulose, hemicellulose, chitin, chitosan, pectin, lignin-based, and/or lignan-based scaffolds. Further, it is contemplated that in certain embodiments, time dependent or independent release of drugs, signalling molecules, growth factors, metabolites, and/or ECM proteins and components may be achieved, with our without use of an additional hydrogel. The presently described approaches may allow for creating larger macro objects with varying degrees of flexibility and/or articulation, for example.

Using the present approach, custom geometries may be created with customizable features while still preserving complex natural structure of the plant-derived scaffold biomaterials. By way of example, it is contemplated that customizable shapes and/or structures may be prepared, and may which may include use of composites, glues, coatings, gels, and/or pastes for providing a desired structure in certain embodiments. As well, in certain embodiments, it is contemplated that complex physical and/or mechanical properties (such as crystal structure, porosity, ductility, toughness, strength, elasticity, plasticity, or any combinations thereof) may be adjusted or controlled by varying the concentration and crosslinker concentration. By varying the amount of crosslinking, it is contemplated that mechanical properties may be controlled/changed. Typically, less crosslinking may lead to a softer material. Further, crosslinking may also change porosity. Typically, higher degrees of crosslinking may decrease porosity. In certain embodiments, such approaches may be minimally invasive for free form injections when used in vivo, and may provide for a gluing-type approach which may allow for control over diverse biochemical and/or biophysical properties.

In certain embodiments, crosslinking methods may include steps of providing a crushed cellulose, adding functional groups to the crushed cellulose, and then crosslinking the crushed cellulose via the added functional groups. In certain embodiments, the methods may also include a step of 3D-printing to provide a desired structure. Material may be moulded or printed into a desired shape, and then crosslinking may be performed to hold and provide structural integrity to the desired shape. By adjusting crosslinking extent and conditions, it is contemplated that density and/or directionality of resultant structures may be controlled.

In certain embodiments, scaffold biomaterials as described herein may be cellulose-based, hemicellulose-based, chitin-based, chitosan-based, pectin-based, lignin-based, lignan-based, or any combinations thereof. In certain embodiments, composite structures as described herein may be tunable with respect to their biochemical, biophysical, and/or mechanical properties.

In certain embodiments, suitable drugs, signalling molecules, growth factors, metabolites, and/or ECM proteins and/or components may be added (i.e. functionalized or loaded on and/or in) to structures as described herein for providing desired responses which may be general or cell/tissue type specific, and/or which may be positive or inhibitory as appropriate for the particular application. In certain embodiments, scaffolds as described herein may be loaded or functionalized with a drug, and used to administer the drug thereby providing for at least some site specific drug delivery, which in certain embodiments may lower dosage and/or increase efficiency of the drug. In certain embodiments, structures as described herein may provide for time-dependent and/or time-independent release of one or more agents such as suitable drugs, signalling molecules, growth factors, metabolites, and/or ECM proteins and/or components.

In certain embodiments, biomaterial scaffolds as described herein may feature customizable shapes and/or structures, and/or may allow for generating larger macro structures having varying degrees of flexibility and/or articulation as desired.

Examples of succinylated cellulose membranes and citric acid crosslinking of cellulose-based hydrogels may be found in Ribeiro-Viana, Renato & Faria Tischer, Paula & Tischer, Cesar. (2016). Title: Preparation of succinylated cellulose membranes for functionalization purposes. Carbohydrate Polymers. 148. 10.1016/j.carbpol.2016.04.033; and Raucci, M. G. & Alvarez-Perez, M. A. & Demitri, Christian & Giugliano, D & De Benedictis, Vincenzo & Sannino, A & Ambrosio, Luigi. (2014). Effect of citric acid crosslinking cellulose-based hydrogels on osteogenic differentiation: Effect of Cellulose-Based Hydrogels on Osteogenic Differentiation. Journal of Biomedical Materials Research Part A. 103. 10.1002/jbm.a.35343, each of which are herein incorporated by reference in their entireties.

Using the approaches described herein, it is contemplated that structures as described herein may overcome and/or improve on certain difficulties associated with larger sizes and corresponding lengthy decellularization times, and/or with diffusion in large constructs. In certain embodiments, structures as described herein may allow for designing of certain structures and features that are not found in nature while exploiting the natural complexity of the source of the scaffold material in the individual subunits. In certain embodiments, structures are described herein may allow for increased complexity in physical and/or mechanical properties (i.e. stress shielding and site specific moduli, channels, pores, etc.). In certain embodiments, the constructs described herein may allow for modification or adjustment of permeability through use of through use of different glues and/or coatings (i.e. sealants for vessels, semipermeable membranes and junctions). In certain embodiments, the constructs described herein may be tunable with regard to mechanic properties and/or junctions based on use of a glue or coating (i.e. varying the Young's modulus). In certain embodiments, structures as described herein may be articulated structures, which may confer varying degrees of flexibility and movement as desired. In certain embodiments, structures as described herein may allow for combination of different cell types in different regions.

In certain embodiments, suitable drugs, signalling molecules, growth factors, metabolites, and/or ECM proteins and/or components may be added (i.e. functionalized or loaded on and/or in) to structures as described herein for providing desired responses which may be general or cell/tissue type specific, and/or which may be positive or inhibitory as appropriate for the particular application. In certain embodiments, scaffolds as described herein may be loaded or functionalized with a drug, and used to administer the drug thereby providing for at least some site specific drug delivery, which in certain embodiments may lower dosage and/or increase efficiency of the drug. In certain embodiments, structures as described herein may provide for time-dependent and/or time-independent release of one or more agents such as suitable drugs, signalling molecules, growth factors, metabolites, and/or ECM proteins and/or components, which may be provided by loading the agent(s) in a suitable gel with varying release properties or by covalently binding the agent(s) to the structures via a chemical functionalization method. In certain embodiments, vessels containing the agent(s) may be packed into vessels which may be covalently linked through linker molecules such as succinic acid. In certain embodiments, vessels may be used to store one or more agents or compounds to be released at a particular time and/or location. In certain embodiments, they may be tethered to the cellulose in a specific region through the use of linker molecule(s) which may be covalently attached to the cellulose. Such vessels may be oriented in site specific locations, and may have time-specific release properties, for example.

In certain embodiments, such chemical modification may allow for steric hindrance difficulties to be reduced or resolved, and/or may allow for increased complexity of site specific modifications. In certain embodiments, linker molecules may be used to mediate connections to drugs, signalling molecules, growth factors, metabolites, ECM proteins and components, etc., as well as vessels containing such compounds, or any combinations thereof.

Sterics may present difficulties in certain circumstances. For example, different cell attachment densities may lead to different cell responses in the absence of any other biochemical or biophysical modification or signalling. In certain embodiments of the structures described herein, the degree of substitution may now be tuned to suit specific functions, for example.

In certain embodiments, cross-linked plant-derived scaffold biomaterials may be used in 3D printing and/or injectable hydrogel applications. In certain embodiments, cross-linked plant-derived scaffold biomaterials as described herein may be for use in non-medical applications such as in synthetic biorobotics or electrical circuitry integration; or any combinations thereof.

Cellulose may be prepared for cross-linking and/or chemical functionalization via a number of different approaches. See, for an example, Ribeiro-Viana, R. M., Faria-Tischer, P. C. S., and Tischer, C. A. (2016). Preparation of succinylated cellulose membranes for functionalization purposes. Carbohydr. Polym. 148, 21-28, which is herein incorporated by reference in its entirety. By way of example, in certain embodiments cellulose may be reacted to form cellulose monoesters of succinic acid, to facilitate cross-linking and/or functionalization with one or more agents such as proteins, enzymes, or therapeutic drugs. In certain embodiments, succinylation may be performed: (a) at a temperature from 30° to 85° C., the cellulose material may be kept in dimethylacetamide 5 to 20% by weight of cellulose and to 5 to 10% by weight LiCl; (b) the cellulose material may be kept in this solvent during 10 minutes to 1 hour and then may be reacted with anhydride succinic in a mol ratio from 1:2 up to 1:12, at 30° to 90° C.; and (c) the obtained cellulose material may be intensely washed with distillated water during 1 to 3 days and cellulose monoesters solid materials obtained may be submitted to step(s) for cross-linking and/or linkage of proteins, enzymes and/or drugs. In certain embodiments, dimethylacetamide and LiCl may be used as solvent in adequate amount avoiding dissolution of cellulose and may permit the reacting upon cellulose with a substantial amount of succinic anhydride. The molecules of succinic acid may combine with hydroxyl groups mainly in C6 group in the surface of cellulose, providing cellulose activated surfaces, for preparing commercial products from cellulose with application in tissue regeneration and pharmaceutical areas, for example. In certain embodiments, the reaction for production of succinic acid esters of cellulose may be performed in which the esterification may take place in one step, without any dissolution of cellulose, keeping its crystal structure and its original shape. The succinylation reaction using dimethylacetamide and LiCl as solvent may provide a process for producing succinic acid esters of cellulose which the esterification takes place in one step without dissolution of cellulose. This reaction may provide an alternative to producing cellulose esters material and may introduce carboxylic acid functional group(s) that may permit the functionalization on the cellulose through production of specific biochemical modification on the surface of cellulose while substantially maintaining the original shape of cellulose. By way of example, in an embodiment, the succinylated cellulose may be functionalized with collagen. This was performed in an example, and the spectra is shown in FIG. 7 evidencing collagen linkage.

FIG. 7 shows results of chemical functionalization of cellulose with denatured collagen. The IR spectrum of the control (grey) and functionalized (black) scaffolds. The control scaffold was functionalized with the linker molecule of succinic acid, but was void of collagen. The absorption peaks of corresponding to the amide (I and II) bonds show the successful covalent addition of collagen to the cellulose chain via the linker molecule succinic acid.

Figure 24:
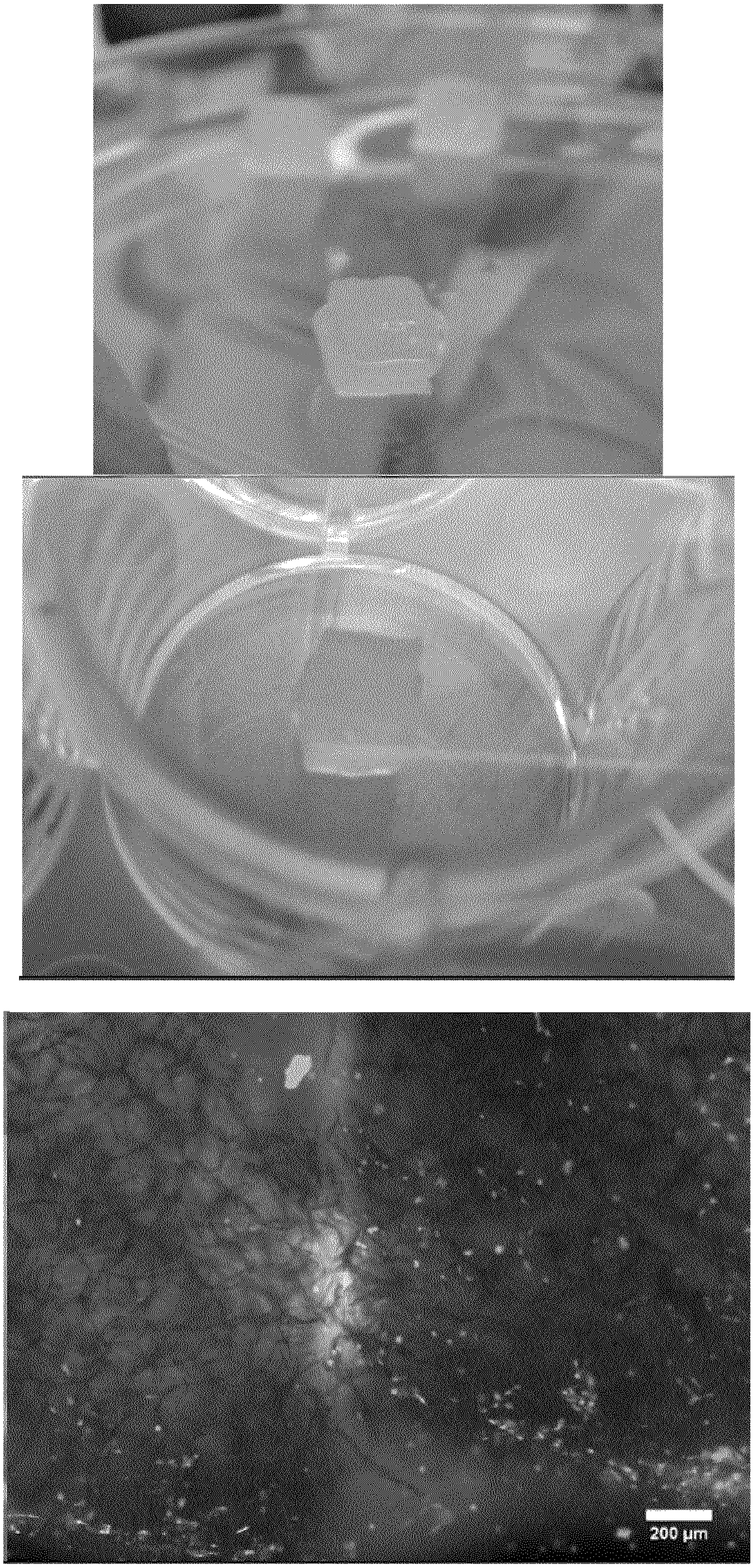
FIG. 24 shows composite cellulose-based materials. Two subunits were glued together with gelatin crosslinked with glutaraldehyde and reduced with sodium borohydride to yield a composite structure. These structures were biocompatible after reduction and support the growth of GFP 3T3 fibroblast cells.

FIG. 24 shows composite cellulose-based materials. Two subunits were glued together with gelatin crosslinked with glutaraldehyde and reduced with sodium borohydride to yield a composite structure. These structures were biocompatible after reduction and support the growth of GFP 3T3 fibroblast cells.

Example 5—3D Cellulose-Based Hydrogels with Channels

In this example, cellulose hydrogels comprising built-in channels derived from plant or fungal sources are provided. The cellulose of the hydrogels may be cross-linked according to methods already described herein, and may allow for preparation of scaffold biomaterials having custom channels configured in cross-linked hydrogels. As well be understood, the present approaches may also be adapted for other hydrogels, such as hemicellulose-based, chitin-based, chitosan-based, pectin-based, lignin-based, lignan-based, or cellulose-based hydrogels, or any combinations thereof. In certain embodiments, components may be sourced from plant and/or fungus. In certain embodiments, plant and/or fungus may be grown and sterilized. In certain embodiments, plant components may be enzymatically isolated and concentrated.

This example provides for hydrogels with built in channels, comprising materials derived from plant or fungal sources. The crosslinking of the cellulose (or other such structure, such as hemicellulose, chitin, chitosan, pectin, lignin, lignan, or any combinations thereof) of the hydrogel may be achieved by cross-linking techniques as described herein. Resulting biomaterials (i.e. 3D crosslinked hydrogels) may have custom channels built into the material. The gel may be printed or cast along with a temporary gel or filler (such as alginate hydrogel). The temporary gel may act as a space filler. Once the cellulose (or other such structure, such as hemicellulose, chitin, chitosan, pectin, lignin, lignan, or any combinations thereof) gel is crosslinked around the temporary gel, the secondary temporary gel may be removed. Several techniques may be used to remove the secondary template hydrogel, such as solution changes and/or temperature changes sufficient to cause a change in the temporary gel allowing for its removal, for example Such approach may provide a non-invasive method of producing channels in desired configurations within the cross-linked gel. Accordingly, more complicated 3D networks of channels and/or pores may be produced.

An example of this approach may be to use alginate as the temporary hydrogel which acts as a channel template. Cellulose (or other such structure, such as hemicellulose, chitin, chitosan, pectin, lignin, lignan, or any combinations thereof) may be printed around these channel templates, and then crosslinked Next, a calcium-free medium such as PBS may be introduced. The alginate will dissolve since it relies on a calcium-rich environment to maintain the crosslinks. The resultant structure may be a material with pre-defined channels and pores.

Ability to template and control channel density and/or positioning within scaffolds and/or crosslinked matrices may be desirable for several different applications. For example, in cell culture and/or in vivo implantation applications, channels may be desirable since, particularly for larger structures and/or implants without channels, diffusion alone may be insufficient in certain environments for providing suitable solution and nutrient exchange. Insufficient diffusion in such instances may risk resulting in a necrotic core where, even if cells are placed at the centre, they may not survive. By introducing suitably configured channels into the material to provide a flow passing through, such challenges may be reduced or overcome. For surgical applications, where an immediate blood supply is desired, there may not be time to wait for angiogenesis to provide channels, and thus providing predefined vasculature via templated channels may be desirable in such instances.

Materials and Methods

Scaffold Gel production: Decellularized material may be prepared according to methods and protocols described in detail herein, see also WO2017/136950, entitled "Decellularised Cell Wall Structures from Plants and Fungus and Use Thereof as Scaffold Materials", herein incorporated by reference in its entirety. The material may then be converted into a gel or paste, to be extruded or 3D printed. The gel state may be achieved mechanically or by treatment with bleach or basic solvents, for example. Moreover, the gel may be crosslinked via chemical functionalization techniques as are described herein.

Channel templating: Several temporary gels may serve as the template for the channels. The temporary gel may be used to block the scaffold gel. This blockage may be patterned in such a manner that once the temporary gel is removed, there will be channels perforating the material. The removal method of the temporary gel may be selected based on the nature and properties of the temporary gel (with due consideration to the nature and properties of the scaffold gel as well). Some methods may include, for example, those based on temperature changes (for example, using heating to change the state of the temporary gel allowing for its removal), ionic solution washes (for example, washing with a solution or agent that degrades or removes the temporary gel), and salt buffer exchanges (for example, exchanging salts to degrade or remove the temporary gel). In certain embodiments, the temporary gel may comprise an alginate gel, for example, which may remain relatively solid in the presence of calcium; however, upon a solvent exchange with a sodium based solvent, it may degrade and wash away.

3D printing: In certain embodiments, the fabrication process may involve, for example, a dual extruder system (one for the primary scaffold gel and the other for the temporary gel template). The material may be built up layer by layer, as in conventional 3D printing or resin printing, allowing for the channels to be templated throughout the scaffold gel as desired and/or as suitable for the particular intended application.

In certain embodiments, the cellulose hydrogels may be printed or cast along with a temporary hydrogel (such as alginate, for example). The temporary hydrogel may act as a space filler. Following crosslinking of the cellulose around the temporary hydrogel (space filler), the temporary hydrogel may be removed. Several techniques may be used for removing the temporary hydrogel, such as by subjecting the materials to solution changes and/or temperature changes. Such approaches may be relatively non-invasive for in vivo applications, while providing desired channels. In certain embodiments, complicated 3D networks of channels and/or pores may be designed.

In certain embodiments, an alginate-based temporary hydrogel may be used, which may act as a channel template. Cellulose may be printed or introduced around these alginate-based temporary hydrogel channel templates, and then the cellulose may be cross-linked Next, a calcium-free medium such as PBS may be introduced, in which the alginate-based temporary hydrogel may dissolve since alginate hydrogels typically prefer a calcium-rich environment in order to maintain crosslinking. The resultant structure may then provide a 3D cross-linked cellulose hydrogel having pre-defined channels and/or pores configured according to placement of the original temporary hydrogel.

In certain embodiments, such approaches may allow for generating customized geometries while substantially preserving structure of the plant-derived scaffold biomaterials.

Using the present approach, custom geometries may be created with customizable features while still preserving complex structure of the plant-derived scaffold biomaterials. In certain embodiments, it is contemplated that complex physical and/or mechanical properties (such as crystal structure, porosity, ductility, toughness, strength, elasticity, plasticity, or any combinations thereof) may be adjusted or controlled by varying the concentration and crosslinker concentration. In certain embodiments, such approaches may be used to provide a template for vascularization, for example. In certain embodiments, by providing configurable channels, difficulties associated with reliance on diffusion in certain applications may be reduced or eliminated.

In certain embodiments, approaches described herein may comprise steps of providing a crushed cellulose gel; functionalizing the cellulose of the crushed cellulose gel with functional moieties for cross-linking; positioning the cellulose gel and a temporary gel such that the temporary gel provides a template for desired channels on and/or within the cellulose gel; cross-linking the cellulose gel; and removing the temporary gel so as to provide a crosslinked cellulose gel comprising channels where templated by the temporary gel.

In certain embodiments, approaches as described herein may allow for molding or printing of the materials into a desired shape or structure, followed by cross-linking so as to provide structural integrity to the desired shape or structure, with channels and/or pores provided in the structure at positions and orientations pre-determined by placement of the temporary gel. In certain embodiments, it is contemplated that density, directionality, or both, of the microstructures, channels, and/or pores may be controllable as desired.

In certain embodiments, the cellulose gel or hydrogel may be or comprise cellulose, or may be replaced with or combined with another similar material such that the cellulose gel or hydrogel described above may be cellulose-based, hemicellulose-based, chitin-based, chitosan-based, pectin-based, lignin, lignan-based, or any combinations thereof. In certain embodiments, 3D hydrogels as described herein may be tunable with respect to their biochemical, biophysical, and/or mechanical properties.

In certain embodiments, suitable drugs, signalling molecules, growth factors, metabolites, and/or ECM proteins and/or components may be added (i.e. functionalized or loaded on and/or in) to 3D hydrogels as described herein for providing desired responses which may be general or cell/tissue type specific, and/or which may be positive or inhibitory as appropriate for the particular application. In certain embodiments, 3D hydrogels as described herein may be loaded or functionalized with a drug, and used to administer the drug thereby providing for at least some site specific drug delivery, which in certain embodiments may lower dosage and/or increase efficiency of the drug. In certain embodiments, 3D hydrogels as described herein may provide for time-dependent and/or time-independent release of one or more agents such as suitable drugs, signalling molecules, growth factors, metabolites, and/or ECM proteins and/or components, which may be provided by loading the agent(s) in a suitable gel with varying release properties or by covalently binding the agent(s) to the structures via a chemical functionalization method. In certain embodiments, vessels containing the agent(s) may be packed into vessels which may be covalently linked through linker molecules such as succinic acid. Such vessels may be oriented in site specific locations, and may have time-specific release properties, for example.

In certain embodiments, chemical modification may allow for steric hindrance to be suitable to allow for increased complexity of site specific modifications. In certain embodiments, linker molecules may be used to mediate connections to drugs, signalling molecules, growth factors, metabolites, ECM proteins and/or components, or any combinations thereof, as well as vessels containing such compounds. Different cell attachment densities may lead to different cell responses in the absence of other biochemical or biophysical modification or signalling, and the present approaches may allow for the degree of substitution to be tuned for specific functions, for example.

In certain embodiments, 3D hydrogels as described herein may be used to provide customizable shapes and/or structures, which may comprise composites, glues, coatings, gels, pastes, or any combinations thereof. In certain embodiments, larger macro structures may be prepared having varying degrees of flexibility and/or articulation.

Using the approaches described herein, it is contemplated that 3D hydrogels as described herein may overcome and/or improve on certain difficulties associated with larger sizes and corresponding lengthy decellularization times, and/or with diffusion in large constructs. In certain embodiments, structures as described herein may allow for designing of certain structures and features that are not found in nature while exploiting the natural complexity of the source of the scaffold material (i.e. cellulose, others) in the individual subunits. In certain embodiments, structures are described herein may allow for increased complexity in physical and/or mechanical properties (i.e. stress shielding and site specific moduli, channels, pores, etc.). In certain embodiments, the constructs described herein may allow for modification or adjustment of permeability through use of through use of different glues and/or coatings (i.e. sealants for vessels, semipermeable membranes and junctions). In certain embodiments, the constructs described herein may be tunable with regard to mechanic properties and/or junctions based on use of a glue or coating (i.e. varying the Young's modulus). In certain embodiments, structures as described herein may be articulated structures, which may confer varying degrees of flexibility and movement as desired. In certain embodiments, structures as described herein may allow for combination of different cell types in different regions.

In certain embodiments, 3D hydrogels as described herein may be used in 3D printing and/or injectable hydrogel applications. In certain embodiments, cross-linked plant-derived 3D hydrogels as described herein may be for use in non-medical applications such as in synthetic biorobotics or electrical circuitry integration; or any combinations thereof.

Example 6—Decellularized Celery Scaffold for Guided Cell Alignment of C2C12 Murine Myoblasts Cell culture in 2D flat Petri dishes fails to recreate directionality of cells in vitro, which is a major characteristic of functional tissue. A wide array of methods, including topographical cues, cyclic strain and electrical stimulation have been used to induce alignment. Nevertheless, these methods typically involve long and costly processing. In this example, the alignment of C2C12 murine myoblast on a decellularized vascular bundle of celery (*Apium graveolens*) is shown.

Alignment and orientation of cells in vivo, referred to as anisotropy, plays a key role in the functionality of tissue. The multinucleated structures in muscle tissue, known as myofibers, rely on uniaxial alignment to generate force along an axis; airways, arteries and veins rely on the circumferential alignment of smooth muscles to facilitate the transport of fluids and gases; and white matter in the brain relies on anisotropic axonal fibres for proper functioning. In the laboratory, however, 2D Petri dishes fail to recreate anisotropy. This in turn has shown a difference in gene expression, which may lead to inaccurate results. To overcome this discrepancy, a wide array of methods including topographical cues, cyclic strain and electrical stimulation have been used to induce alignment. However, these methods are often laborious and rely on the use of specialized equipment. The present example provides the alignment of C2C12 murine myoblast on the decellularized vascular bundle of celery (*Apium graveolens*). The xylem channels (38.50 μm±6.86) and phloem channels (21.52 μm±5.0) lie within the 10-100 μm diameter suitable for optimal myoblast alignment. Following 10 days in proliferation media, the actin filaments of C2C12 and apex of nuclei were observed to be oriented parallel to the vascular bundle-grooves. Subsequently, after 5 days in differentiation media, myotubes with an average length of 308.08±169.44 μm (N=103) were −2.44°±3.83 (N=14) from the mean direction of the vascular bundle. These results show that the microtopography of the vascular bundle guided muscle cell alignment. The results presented here highlight this plant-derived scaffold for in vitro applications of muscle myogenesis, and/or where structural anisotropy is desired to more closely resemble in vivo configuration and/or conditions.

The multinucleated structures in muscle tissue, known as myofibers, allow for the generation of force along an axis (Chal & Pourquié, 2017; Narayanan et al., 2002). Airways, arteries and veins rely on the circumferential alignment of smooth muscles to facilitate the transport of fluids and gases (Clark & Pyne-Geithman, 2005; Komuro et al., 1982); and white matter in the brain relies on anisotropic axonal fibres for proper functioning. (Feng et al., 2013). In the laboratory, however, in vitro studies are typically performed on flat 2D Petri dishes which lack biologically active adhesion sites, dimensionality, microtopography, and proper mechanical stimuli. This in turn causes cells to appear randomly scattered; and portray dissimilarities in proliferation, differentiation and overall gene expression. In order to further assimilate 2D cell culture to the in vivo environment, substrates with a wide array of topographical structures, such as posts (Goedecke et al., 2015;), microchannels (Humes et al., 2012), and nanofibers (Fee et al., 2016) have been developed (Goedecke et al., 2015). And to further understand the role of directionality, or in other words, induce cellular anisotropy, grooves, microchannels, cyclic strain and electrical stimulation have been shown to induce such phenomenon (Tanaka et al., 2014, Liu et al., 2008, Humes et al., 2012; Altomare et al., 2010; Charest et al., 2007). It was noted that smooth muscle cells (Kuppan et al., 2016), skeletal muscle cells (Cooper et al., 2010), neurons (Basso et al., 2018) and tendon derived cells (Foolen et al., 2018) portrayed a difference in gene expression when compared to the smooth surfaces of tissue culture dishes. Skeletal muscle cells portrayed upregulated troponin T, myosin heavy chain and myogenin on uniaxial grooves (Cooper et al., 2010). Substrate topography has also been shown to influence differentiation lineage of mesenchymal stem cells. Mesenchymal stem cells cultured on grooves and ridges committed to myogenic and adipogenic line, whereas smooth surface induced osteogenic differentiation (Wang et al., 2012).

Microchannel development has proven to be a popular method due to tunability and relative ease-of-use acquired through techniques, such as photolithography (Camelliti et al., 2006; Leclerc et al., 2013), femtosecond pulsed laser (Yeong et al., 2010), 3D printing (Tan et al., 2017; Tijore et al., 2018) and electron-beam lithography (Wang et al., 2010; Goto et al., 2007). It has been shown that microchannel width ranging from 5-200 μm may induce alignment of myoblast, where channels 20 to 100 μm wide allowed for optimal myotube maturation (Humes et al., 2012; Sun et al., 2013; Altomare et al., 2010; Charest et al., 2007). The depth of the channels has also been shown to play a role in cell alignment. Microgrooves 2 μm deep provide a temporary cue for cell alignment, whereas channels greater than 5 um deep have been shown to induce permanent alignment (Zhao et al., 2009; Hume et al., 2012). This observation appeared to be cell line specific: C2C12 responded to grooves below 0.5 μm differently than primary myoblast (Altomare et al., 2010). On the discussed substrates, cell alignment may be attributed to confinement and contact guidance. Cells were considered aligned if the mean angle of cells with reference to the direction of the substrate pattern was below 10° (Altomare et al., 2010 & Charest et al., 2007)

Biocompatibility of decellularized plant tissue in vitro and in vivo makes these substrates appealing. Through the use of surfactants, such as SDS, the cell membrane becomes compromised leading to cell lysis. (Fontana et al., 2017; Modulevsky et al., 2014; Brown and Audet, 2008; Modulevsky et al., 2016; Hickey et al., 2018) Immortalized cell lines were shown to proliferate throughout the relatively porous decellularized apple tissue without the need for biofunctionalization (Modulevsky et al., 2014; Hickey et al., 2018). Through biofunctionalization, however, cardiac muscle cells were shown to contract spontaneously (Gershlak et al., 2017). In vivo studies showed that implanted decellularized apple tissue showed minimal immune response and guided angiogenesis (Modulevsky et al., 2016). In addition to biocompatibility, the mechanical properties have been shown to resemble that of skeletal (Hickey et al., 2018) and cardiac muscle (Gershlak et al., 2017) tissue. Decellularized plant tissue lacks the biochemical cues natively found in mammalian extracellular matrix (Thorsteinsdóttir et al., 2011). Yet, the tunability potential of cellulose, including biofunctionalization, may be used to further extend its applications (Courtenay et al., 2018; Courtneay et al., 2017; Fontana et al., 2017).

Previous microchannel techniques may induce alignment; however, these methods are considered laborious and rely on the use of specialized equipment. As part of the wide arrays of structures found in plants, the vascularization of plants is composed of vessels with diameters in the micrometer scale (Scarpella & Meijer, 2004; Karam, 2005; Myburg et al., 2013). In the case of celery (*Apium graveolens*), a dicot plant, the vascularization is composed of two major structures: xylem and phloem (Scarpella & Meijer, 2004). The xylem (including cambium) is composed of 38.50 μm±6.86 wide channels, whereas the phloem is composed of 21.52 μm±5.0 wide channels. In contrast to the phloem, xylem tissue possesses a lignified helical secondary cell wall, which can be visualized through fluorescent staining (Tobimatsu et al., 2013).

In this example, C2C12myoblasts were aligned along the longitudinal direction of the vascular bundle (V.B). By measuring the preferred orientation of the myotubes, it is shown that C2C12 murine myoblast and myotubes align parallel to the V.B.

In this study a highly accessible, reproducible method for guided cell alignment is shown. The natural topography of the vascular bundle induces uniaxial orientation, or anisotropy, of muscle cells. The method presented here may facilitate investigation on the effects of cellular anisotropy, and may broaden understanding of cellular phenomena, such as myogenesis. Although the present example is focused on skeletal muscle, a variety of other cell types are also contemplated, as well as techniques further employing functionalization and/or tunable mechanical properties which may even further extend cell-type variety and/or applications.

Figure 18:
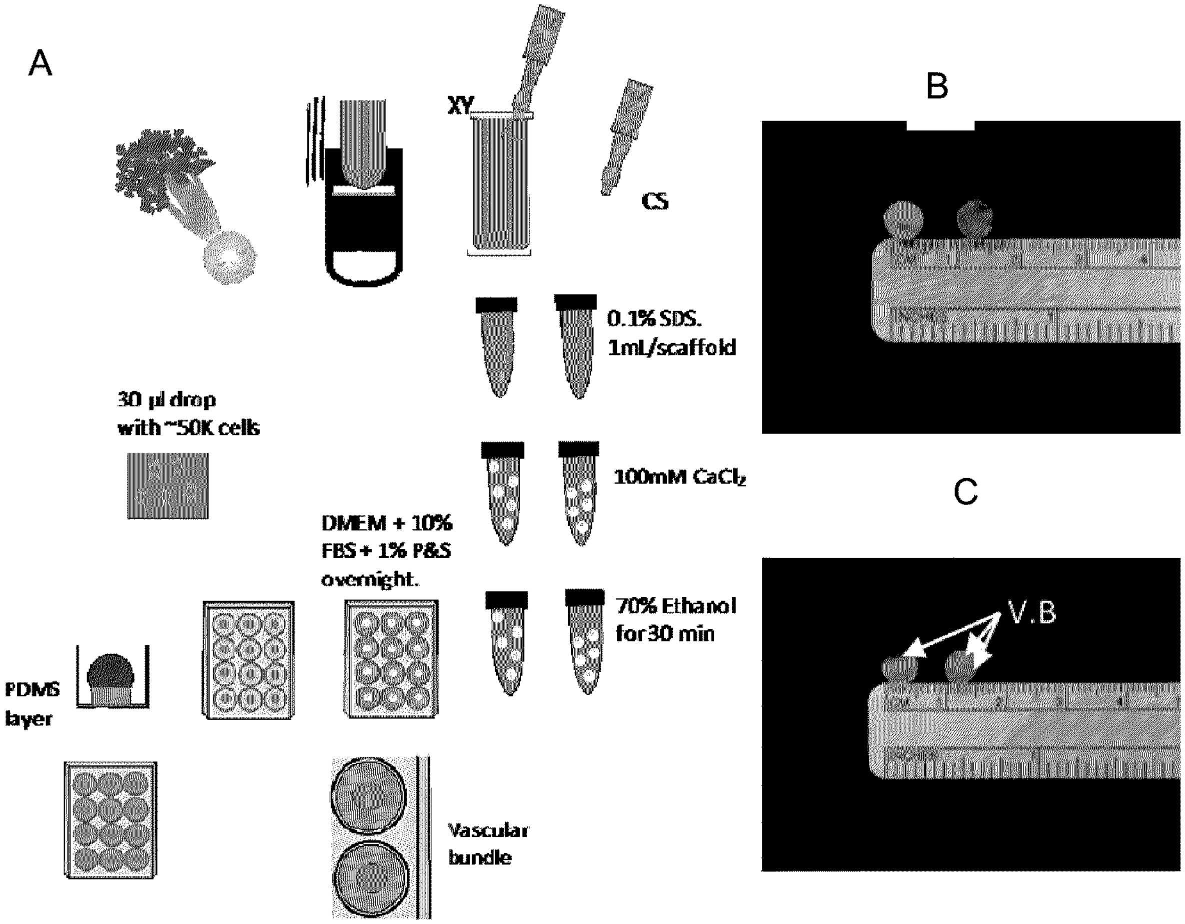
FIG. 18 shows (A) visual representation of celery-scaffold preparation. (B) Samples were 6 mm wide and 2.15±0.15 mm thick. "XY" corresponds to scaffolds cut longitudinally with respect to the celery stalk, whereas "CS" corresponds to cross sections. Approximately 50,000 Cells were seeded on (C) decellularized scaffolds and left on scaffold for 4.5 hours. V.B.=Vascular bundle.

Methods:

Scaffold Preparation: The decellularization protocol was based on that of Hickey, R. J., Modulevsky, D. J., Cuerrier, C. M., & Pelling, A. E. (2018). Customizing the shape and microenvironment biochemistry of biocompatible macroscopic plant-derived cellulose scaffolds. ACS Biomaterials Science & Engineering, doi:10.1021/acsbiomaterials.8b00178, and WO2017/136950, entitled "Decellularised Cell Wall Structures from Plants and Fungus and Use Thereof as Scaffold Materials", which are herein incorporated by reference in their entireties. Briefly, celery (*Apium graveolens*) stalk was cut parallel and perpendicular to the longitudinal axis using a mandolin slicer. A 6 mm biopsy punch was then used to obtain round scaffolds with the exposed vascular bundle in a longitudinal (XY) and cross section (CS) conformation. The samples were then transferred to a 15 mL Falcon tube containing 0.1% SDS at a ratio of one sample per mL of 0.1% SDS solution. Samples were then agitated in a shaker at 120 RPM for 72 hours. Following treatment with SDS, the samples were washed three times with deionized water. After the final wash, 100 mM solution of $CaCl_2$ (1 mL per scaffold) was added and samples were incubated at room temperature for 24 hours. After 24 hours, the samples were washed with distilled water three times. On the final wash, the water was removed and 70% ethanol was added for 30 min. At this point, the samples were brought into a class II biosafety cabinet and washed three times with sterile PBS. The samples were placed on PDMS coated 12-well plates with 2 mL of growth media (refer to next section). The samples were incubated overnight at 37° C. and 5% $CO_2$. Prior to cell seeding, the media was removed (FIG. 18).

The 0.1% SDS was used to lyse the plant cells, and 100 mM $CaCl_2$ solution was later used to reach the cloud point and facilitate removal of residual SDS (see Hickey, R. J., Modulevsky, D. J., Cuerrier, C. M., & Pelling, A. E. (2018). Customizing the shape and microenvironment biochemistry of biocompatible macroscopic plant-derived cellulose scaffolds. ACS Biomaterials Science & Engineering, doi: 10.1021/acsbiomaterials.8b00178, and WO2017/136950, entitled "Decellularised Cell Wall Structures from Plants and Fungus and Use Thereof as Scaffold Materials", which are herein incorporated by reference in their entireties). Myotubes were stained for MYHC and the celery scaffolds were stained with calcofluor white. The Directionality plug-in on Image-J FIJI was used to analyse the alignment of images containing 20-100 moyotubes (MYHC positive structures with two or more nuclei). Data presented as Mean±S.D.

Cell culture: C2C12 murine myoblast were plated on tissue culture plates and maintained at 37° C. with 5% $CO_2$. Cells were cultured in growth media consisting of high glucose DMEM with L-glutamine and sodium pyruvate (Hyclone) supplemented with 10% FBS (Wisent & Hyclone) and 1% penicilin (10000 U/mL) & streptomycin (10000 ug/mL) (Hyclone). Once the cells reached 70-80% confluency, they were trypsinized (0.05%), resuspended in growth media, and spun down in the centrifuge at 1000 RPM (97 g) for 3 min. Following centrifugation, the pellet was resuspended in growth media to acquire 1.7×106 cells/mL. Cells were counted using a hemocytometer and trypan blue to determine viability. 30 μL of media containing cells was placed on the scaffolds and incubated for 4.5 hours. Following the incubation, 2 mL of growth media was added and samples were incubated for the 10 days with media change every 48 hours until day 7, followed by daily media until day 10. For differentiation studies, cells were placed in differentiation media for 5 days. The differentiation media was composed of high glucose DMEM, 2% horse serum (Gibco) and 1% Penicillin and streptomycin.

Fluorescent staining: Following incubation, scaffolds were transferred to a microcentrifuge tube using a metal paddle (to minimize contact with exposed vascular bundle) and washed three times with phosphate buffered saline (PBS). The samples were fixed with 3.5% paraformaldahyde in 2% sucrose solution for 10 min and washed three times with PBS. Following the final PBS wash, room temperature triton-X100 was added to permeabilize the cells. The scaffolds were once again washed three times with PBS. For F-actin imaging, scaffolds were stained using Alexa Fluor 488 phalloidin (Invitrogen) in PBS at a 1:200 concentration and incubated for 20 min in the dark. Nuclei was stained by placing the scaffolds in 10% RNAse in PBS (DNase and protease-free) (Thermo Fisher) for 30 min at 37° C., followed by PBS wash (3×). After the third wash, propidium iodide(1 mg/mL) (Thermo Fisher) was added at a 1:1000 concentration for 30 min. Cellulose was stained with 10% calcoflour in PBS for 20 min at room temperature.

To test for the presence of myotubes, scaffolds from the 5-day differentiation treatment were fixed and permeabilized as described previously. These samples were then washed three times with cold wash buffer (5% FBS in PBS) and placed at 4° C. for 20 min. The cold wash buffer was removed and MF-20 (DSHB Hybridoma Product) was added at a 1:200 concentration made up in cold wash buffer and incubated for 24 hours at 4° C. The MF-20 solution was removed, and the scaffolds were washed three times with cold wash buffer. Samples were stored in cold wash buffer for 20 min at 4° C. before adding the secondary antibody.

Anti-Mouse IgG (whole molecule)—FITC (Sigma) was added at a 1:100 concentration and placed in the refrigerator for 1 hour. To confirm decellularization of the celery scaffolds, native and decellularized samples without C2C12 were placed in 1:500 hoescht 33342(Invitrogen) made up in PBS for 30 min at 37° C.

Microscopy: Scaffolds were placed on coverslips with mounting medium (Vectashield H-1000) was added prior to imaging. The samples were imaged with a Nikon TiE A1-R high speed resonant scanner confocal microscope with a 10× and 40× lens. Image processing was done on Image-J FIJI. The images presented throughout this manuscript are max projections of approximately 200 μm confocal volumes composed of images taken every 5 μm. Brightness of fluorophore signal was enhanced to improve contrast of structures.

Scanning electron microscopy: Sample preparation was performed as described previously (Murtey and Ramasamy, 2016). Briefly, the sample was washed three times with PBS and placed in a solution containing 3.5% paraformaldahyde (in 2% sucrose solution) and 1.5% glutaraldehyde (Final concentration) overnight. Post fixation, the sample was washed again with PBS and dehydrated through a sequential ethanol gradient (30,50,75,95 & 99%). The sample was dried using the Samdri-PVT-3D Critical point dryer in 99% ethanol. The dried sample was gold sputtered with a 5 nm layer (LEICA EM ACE 200). The samples were image with a JEOL JSM-7500F FESEM at 2.0 KV.

Directionality measurement and myotube length: Images of scaffolds containing between 20 to 100 Myotubes (MF-20 positive structures with two or more nuclei) and calcofluor/propidium iodide stained structures were taken 1 mm away from the edge of the vascular bundle due to potential damage brought upon by the biopsy punch and mandolin. The images were thresholded using the Adaptive Threshold plug-in on ImageJ-FIJI to isolate the stained myotubes and vascular bundle. The directionality of the structures was determined using the Directionality plug-in on Image J-FIJI. The mean direction from both structures (myotube and vascular bundle) was used to normalize the directionality data.

Statistical analysis: In order to test for isotropy, the normalized direction of the myotubes with reference to the vascular bundle was statistically analyzed using the Rayleigh test. Alpha value was set at 0.05. Values are displayed as mean±standard deviation.

Results and Discussion:

The diameter of the xylem and phloem was calculated to be 38.50 μm±6.86 and 21.52 μm±5.0. Following 10 days in proliferation media, the actin filaments and apex of nuclei were observed to be oriented along the vascular bundle-grooves. Subsequently, after 5 days in differentiation media, myotubes with an average length of 308.08±169.44 μm (N=103) were aligned −2.44°±3.83 (N=14) within the direction of the vascular bundle.

Figure 5:
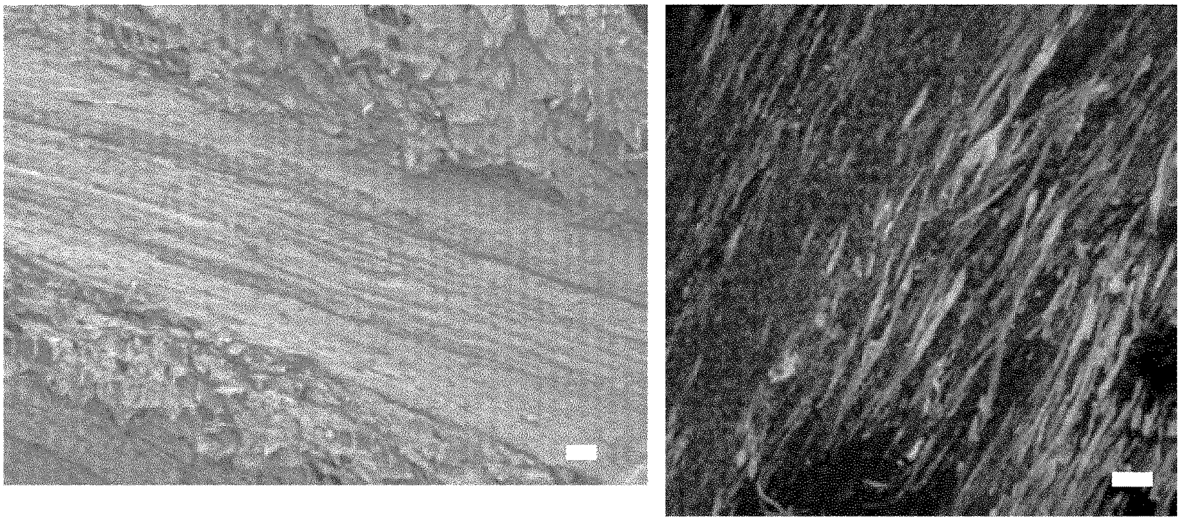
FIG. 5 shows (A) SEM image of longitudinally cut vascular bundle; and (B) C2C12 myotube alignment. Scale bar=100 μm.

Results are shown in FIGS. 4 and 5, in which FIG. 4 shows (A) 6×2 mm longitudinal scaffold, and (B) cross section of vascular bundle ((Blue) Ground tissue and phloem; (Red) Xylem). FIG. 5 shows (A) an SEM image of longitudinally cut vascular bundle, and (B) shows C2C12 myotube alignment (scale bar=110 μm.

Anisotropy is a key characteristic of functional muscle tissue. Studies have shown a difference in gene expression between anisotropic and isotropic muscle cells (see Cooper, A., Jana, S., Bhattarai, N., & Zhang, M. (2010). Aligned chitosan-based nanofibers for enhanced myogenesis. Journal of Materials Chemistry, 20(40), 8904. doi:10.1039/c0jm01841d, which is herein incorporated by reference in its entirety). In order to address this difference and further mimic in vivo conditions, methods have been shown to induce cell anisotropy. Here a low cost, readily performed and reproducible method is provided, through which guided alignment of C2C12 myoblast was achieved in these studies. By longitudinally cutting the vascular bundle of decellularized celery, grooves with diameters ranging from ~20 to approximately 40 μm were acquired. Following 10 days in growth media, the actin filaments and apex of nuclei were observed to be aligned. Subsequently, after 5 days in differentiation media, the myoblast fused and expressed MYHC. The 308.08±169.44 μm long myotubes were within −2.44°±3.83 (N=14) with respect to the direction of the vascular bundle/grooves.

Following 3 days in 0.1% SDS, the scaffold lost the green color due to the loss of cellular components (FIG. 18). In order to facilitate removal of SDS, 100 mM concentration of $CaCl_2$ was added to the scaffolds for 24 hours. The decellularization of the V.B. was determined using a membrane permeable stain, Hoescht 33342. Therefore, a comparison between native and decellularized images was expected to depict the nuclei of companion cells in the phloem, as opposed to the outline of companion cells lacking a nuclei in decellularized tissue. The xylem and sieve tube elements don't possess a nucleus (Schuetz et al., 2012).

Figure 19:
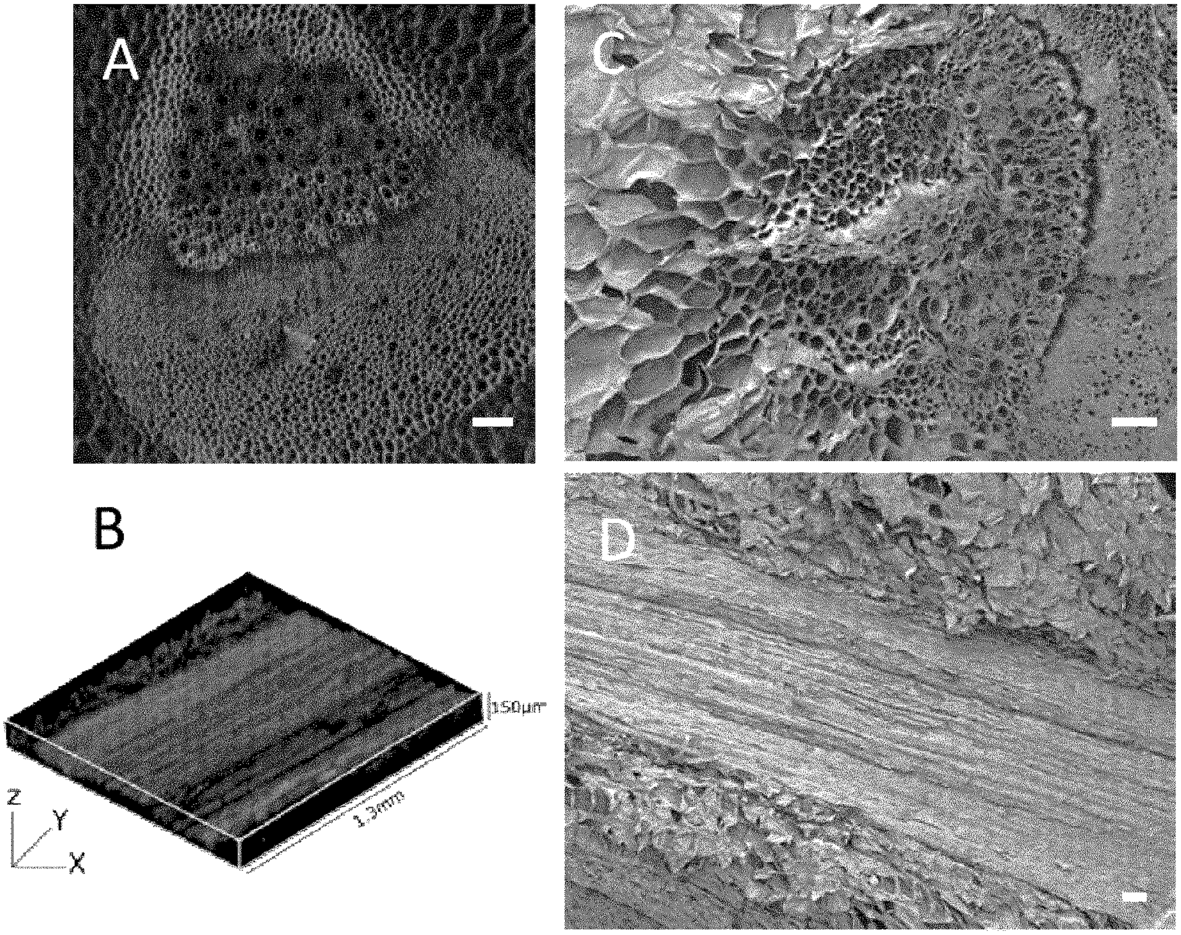
FIG. 19 shows vascular bundle of celery. (A) Max projection of cross section and (B) 3D reconstruction of longitudinal cut of vascular bundle. Phloem and ground tissue were stained with calcofluor (Green); lignified tissue was stained with propidium iodide (Red). SEM images of vascular bundle (C) cross section and (D) longitudinal cut. Scale bar=100 μm.

The vascular bundle of the celery (*Apium graveolens*) is composed of phloem and xylem (including cambium). The diameter of the phloem vessels was determined to be 21.52 μm±5.0 (N=53.), whereas the xylem vessels were 38.50 μm±6.86 (N=31) wide. By cutting the celery stalk parallel to the longitudinal axis, grooves of varying depth and width were acquired within that of the diameter of the intact channel. The exposed vascular bundle samples ("XY" conformation) were cut into round samples 6 mm in diameter to facilitate cell seeding. The phloem and xylem were distinguished based on their ability to interact with propidium iodide and calcoflour (see FIG. 19). The lignified tissue within the xylem interacted with propidium iodide leading to the red emission. In contrast, the phloem and ground tissue interacted with calcofluor, which led to a blue emission. It can also be observed on FIG. 20 that the secondary cell wall of xylem tissue is helical in shape. (Schuetz et al., 2012).

Cells were seeded on the decellularized scaffolds at a concentration of ~5×10$^5$ cells/mL. The 30 μm drop was left on the scaffold for 4.5 hours. By day 10 in proliferation media, it was observed that actin filaments and long axis of nuclei portrayed a preferred orientation with reference to the direction of the grooves (see FIG. 20). Following 5 days in differentiation media, the cells were expressing myosin heavy chain, which was detected through MF-20 interaction. The formation of myotubes shows that the substrate didn't interfere with early differentiation of myoblast. The average myotube length was determined to be 308.08±169.44 μm (N=103). For the most part, myotubes were observed to have an elongated morphology; yet, in some cases, an isotropic grouping of nuclei was noted. The alignment histogram from myotubes on ground tissue is relatively uniform (flat), in comparison to the histogram for the myotubes on the V.B, which clearly depicts skewness (see FIG. 21). The normalization of myotube orientation with respect to the vascular bundle (−2.44°±3.83 [N=14]) is presented in FIG. 21. The spread around 0 degrees was analyzed using the Rayleigh test, leading to rejection of the null hypothesis of equal spread or isotropy ($p \approx 0$)

In some cases, the formation of myotubes was observed to be isotropic. The lack of uniformity in the channel diameter and arrangement likely led to smooth or damaged areas, which disrupted the groove pattern.

Cell culture in flat 2D dish typically fails to recreate cell-cell and cell-matrix interactions in three dimensions, alongside a wide array of physical cues, such as biochemical, topographical and mechanical (Antoni et al., 2015; Fang & Eglen, 2017). In order to address the effects of the matrix, a wide array of substrates have been proposed. Microtopographies, such as micropost (Goedecke et al., 2015), fibers (Soliman et al., 2018; Cooper et al., 2010; Schoenenberger et al., 2018) and channels of various sizes have been used to study cell behavior (Hume et al., 2012; Huang et al., 2010; Leclerc et al., 2013). A major characteristic of functional tissue is anisotropy, which correlates with functionality. In-vitro studies have showed that myoblast alignment upregulated the expression of troponin T, myogenin and myosin heavy chain II (Cooper et al., 2010). Another group showed that cell viability and proliferation of smooth muscle cells increased on aligned PHBV nanofibers, alongside an increase in gene expression of contractile markers (Kuppan et al., 2015).

Anisotropy in vitro has been achieved through electrical stimulation (Tanaka et al., 2014), cyclic strain (Liu et al., 2008), confinement (Humes et al., 2012) and topographical cues (Zhao et al., 2009). Great emphasis has been placed on microchannel development techniques, such as 3D printing (Tan et al., 2017), electron-beam lithography (Goto et al., 2007), photolithography (Humes et al., 2012; Leclerc et al., 2013; Zhao et al., 2009) and Softlitography (Glawe et al., 2005). Yet, microchannel development has typically been a laborious and costly endeavour. It has been shown that channels 20-200 um wide induce alignment of muscle cells, where channels with a diameter 10-100 μm wide produced optimal myotube formation. (Humes et al., 2012; Sun et al., 2013).

The vascularization of plants may present a topography (Fontana et al., 2017) which may be appropriate for guided cell alignment. In the case of celery, the vascular bundle is composed of xylem (which includes cambium) and phloem. The xylem is composed of 38.50 μm±6.86 (N=31.) wide channels, whereas the phloem is composed of 21.52 μm±5.0 (N=53) wide channels (see FIG. 19). By cutting the celery stalk longitudinally, this example shows it was possible to acquire grooves with diameters within that of intact channels. The decellularization was done based on previously published protocol, which used a low concentration of SDS followed by incubation with $CaCl_2$ to reach the cloud point and simplify the removal of SDS (see FIG. 18) (Hickey et al., 2018). Decellularized plant tissue may be used as a substrate for 3D cell culture of immortalized and primary mammalian cells (Modulevsky et al. 2014; Gershalk et al., 2017; Fontana et al., 2017; Hickey et al., 2018) Moreover, Gershalk et al depicted the adherence and proliferation of primary cells on the vasculature of a spinach leaf (2017). In this example, it was hypothesized that C2C12 murine myoblast may adhere, proliferate and differentiate on the vascular bundle of celery.

Figure 20:
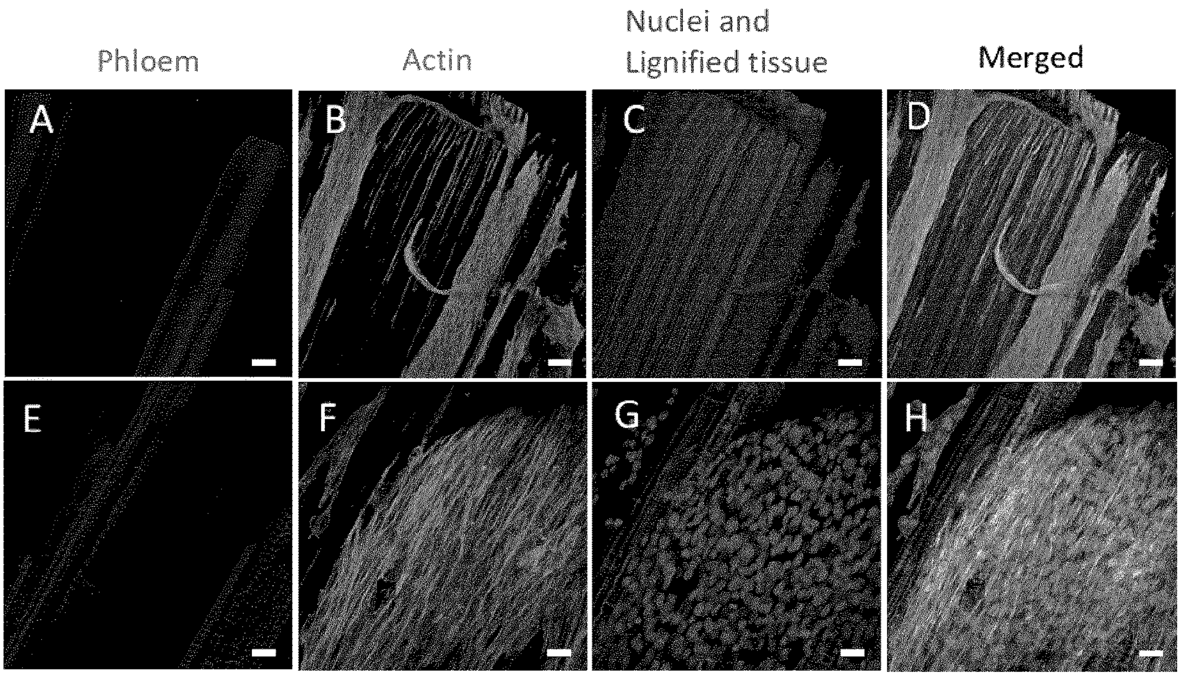
FIG. 20 shows myoblast alignment on the decellularized vascular bundle of celery (*A. graveolens*) at day 10. (A&E) Phloem and ground tissue: Blue (Calcoflour); (B&F) actin filaments: green (Phalloidin 488); (C&G) nuclei and lignified tissue: Red (propidium iodide).(A-D) scale bar=100 μm. (E-H) Scale bar=25 μm.
Figure 21:
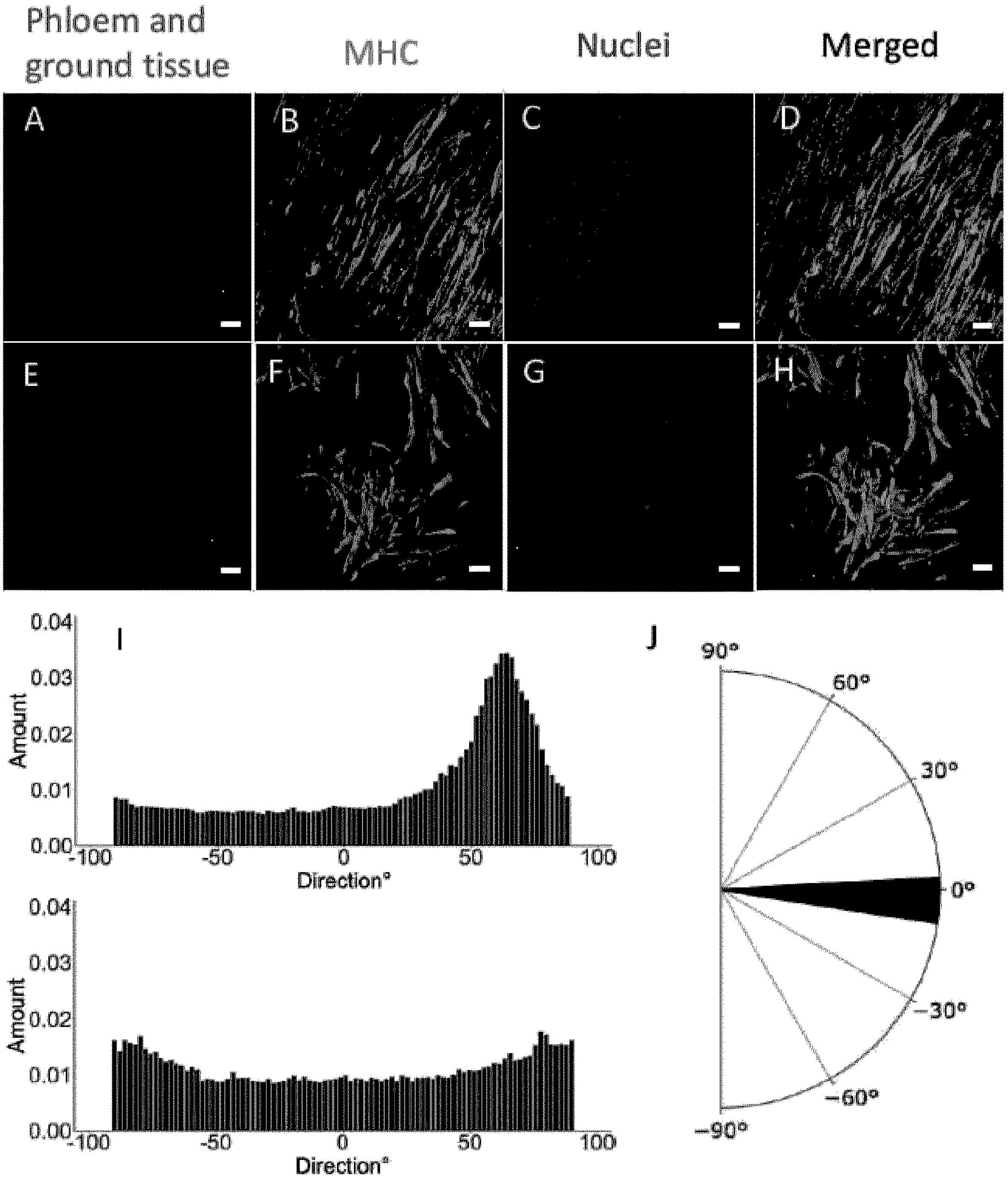
FIG. 21 shows (A-D) Myotube alignment on the decellularized vascular bundle of celery (*A. graveolens*). Myotubes: green (Myosin heavy chain antibody); nuclei: red (propidium iodide); Ground tissue and vascular bundle: Blue (calcofluor). Scale bar=100 μm. Alignment was based on the direction of the longitudinal axis of the myotubes. In (I), (Top) Skewed histogram corresponds to the directionality output of the (B) anisotropic myotubes. (E-H) Isotropic conformation of myotubes on ground tissue. In (I), (Bottom) Uniform histogram corresponds to the Directionality output of the (F) isotropic myotubes. (J) Polar coordinate graph of (Dark area) normalized myotube data (−2.44°±3.83), where 0 degrees corresponds to the direction of the vascular bundle.
Figure 22:
FIG. 22 shows orthogonal view of phloem stained with calcoflour. The image was taken using a multiphoton microscope. Arrows: Smooth areas. Scale bar=25 μm.
Figure 23:
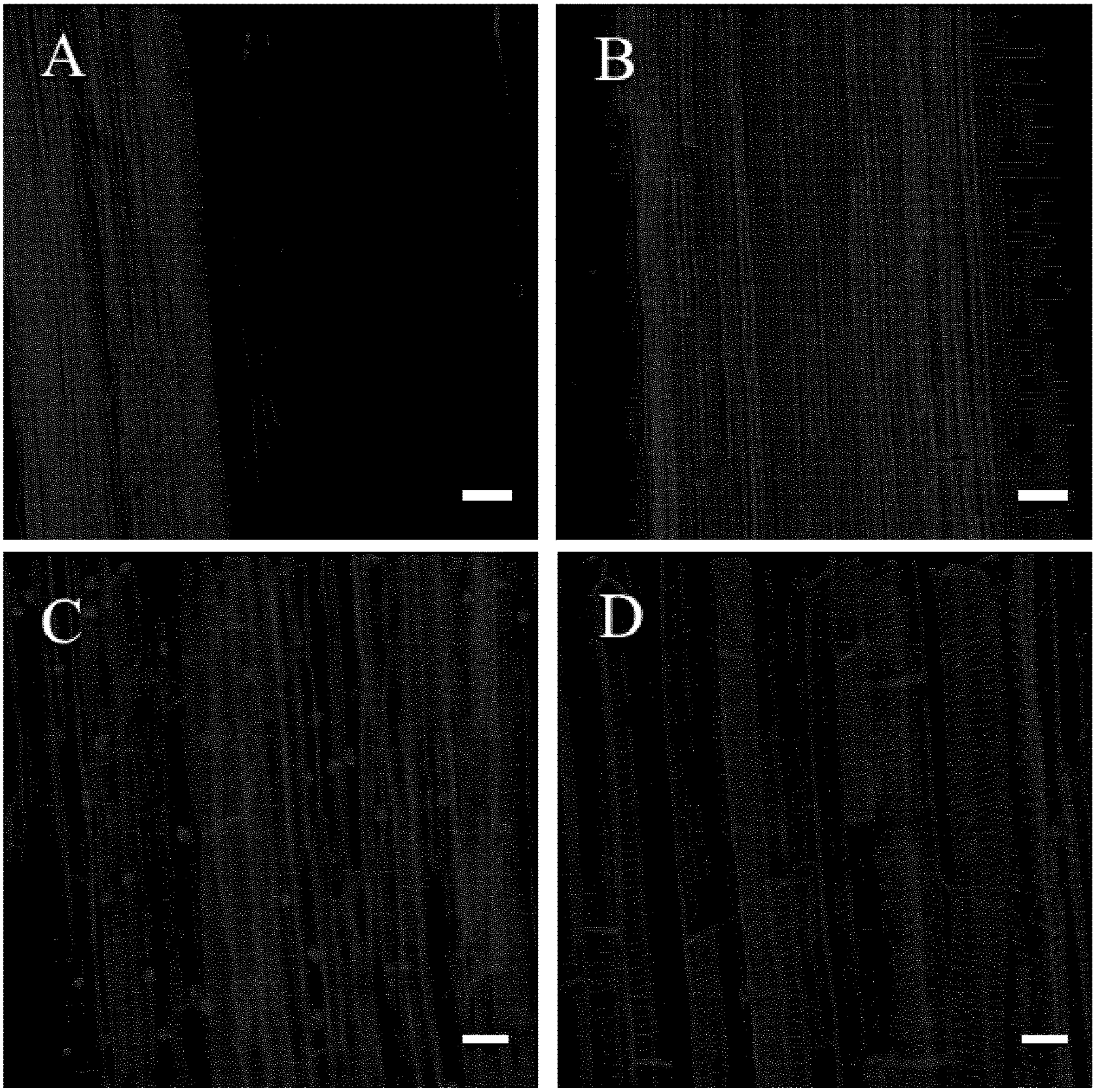
FIG. 23 shows Hoescht 33342 staining of (B&D) decellularized and (A&C) native vascular bundle. (C) Nuclei correspond to companion cells of phloem (A&B) Scale bar:100 μm. (C&D) Scale bar: 25 μm.

Following 10 days in culture, the actin filaments and nuclei (direction of apex) of C2C12s were observed to be oriented parallel to the longitudinal axis of the V.B (see FIG. 20). Taking into consideration the non-uniform arrangement of channels within the vascular bundle leads us to assume that the diameter of the channels varied. Cells were likely confined and in other cases guided through contact guidance. As reported by Altomare et al. (2010), 25 μm and 50 μm wide grooves with a depth between 0.5 and 2.5 μm presented enough of a topographical cue for cell alignment. And in contrast to deeper grooves, the cells were reported to be more elongated. This observation, however, appeared to be cell line specific: C2C12 didn't respond to grooves below 0.5 μm as well as primary myoblast (Altomare et al., 2010).

In reference to FIG. 21(D), the presence of cells on the xylem appears drastically lower compared to cells on the periphery. This was not observed in all cases; however, it is contemplated that the hydrophobic nature of lignin (Lourenco et al., 2016; Schuetz et al., 2013) and the much stiffer structure (Farahi et al., 2017; Lee, 1981; Hepworth & Vincent, 1998) may have negatively affected cell adherence and thus proliferation (Webb et al., 1998; Dowling et al., 2011; Ishizaki et al., 2010). As reported by Papenburg et al., patterned hydrophobic surfaces improve initial cell attachment of C2C12 pre-myoblast; yet, lower proliferation and spreading was noted (2010).

Taking into consideration the alignment of myoblast it was hypothesized that myotubes may also form parallel to the direction of V.B. Following 5 days in differentiation media, the direction of myotube formation was notably influenced by the substrate. An average myotube length of 308.08±169.44 μm (N=103) was calculated. Myotubes on ground tissue yielded a mostly uniform histogram, whereas myotubes on the V.B. yielded a skewed histogram. A skewed histogram depicts a preferred orientation for the particles analyzed by the plug-in (see FIG. 21). It is believed, therefore, that the substrate topography may have influenced the direction of myotubes. The spread of the myotube-histogram is likely due to the noise from non-specific antibody binding and detachment of cells during the staining steps. It was also noted that in some cases, the myotubes were spread isotropically. This observation is likely attributed to the smooth and damaged areas brought upon by the preparation method.

After normalizing the data (Orientation of myotubes with respect to the V.B.), a mean difference of −2.44°±3.83 (N=14) was recorded. Based on the Rayleigh test, the null hypothesis that the orientation of myotubes was randomly spread around a 180° interval (P≈0) was rejected (see FIG. 21). With respect to literature values, the data presented here falls within the spread to conclude that the substrate guided cell alignment. Cells were considered to be aligned when the normalized direction of myotubes with respect to the substrate fell below 10° (Altomare et al., 2010; Chares et al., 2007).

Hume et al. reported that microchannels 40 μm wide and 200 μm deep caused approximately 89% of cells to elongate along groove (2012). In another study, where fibronectin line patterns were utilized to induce alignment, 50 μm wide lines had a slightly greater spread; yet the fusion index and overall maturation of myotubes increased (Sun et al., 2012). In comparison, anisotropic polyurethane fibers oriented >90% of cells within 10° (Liao et al., 2008).

Here it is shown that the vascular bundle of celery was able to induce alignment of myoblast and subsequently myotubes. However, it lacks a wide array of factors that influence cells in vitro, such as biochemical and mechanical cues. As elucidated previously, the xylem and phloem of plants has been determined to be approximately 106 (Farahi et al., 2017; Hepworth & Vincent, 1998) and 103 (Lee, 1981) times stiffer than muscle tissue (Engler et al., 2004), respectively. With reference to mammalian cells, stiffness has been shown to influence cell behavior, such as viability, morphology and differentiation (Engler et al., 2004; Levy et al., 2009; Wells, 2008).

In this example, the presence of MHC was tested for using MF-20. This antibody recognizes all MHC isoforms, therefore, this doesn't reflect the differentiation stage of myotubes without testing for other markers, such as Acta1 and Glut4 (Chal and Pourquie, 2017). Based on the centralized location of the nuclei, as opposed to that of mature muscle tissue where the nuclei is found in the periphery (Roman and Gomes, 2018;), it's likely that the myotubes were still immature and it is not determined if C2C12 cultured on the decellularized vascular bundle of celery may express sarcomeric proteins.

Microchannel fabrication often involves post-treatment and coating with bioactive factors to increase cell adhesion (Huang et al., 2010; Leclerc et al., 2013; Wang et al., 2010; Gingras et al., 2009). In contrast, the vascular bundle in this example allowed for adherence and differentiaton of muscle cells without a need for coating. Yet, the role of adhesive proteins naturally found in FBS (Olivieri et al., 1992; Hayman et al., 1985) was not disregarded. Adding on, it may be postulated that biofunctionalization may further improve the substrates biocompatibility and extend the use of this low cost, appealing, and biocompatible material to other more problematic cells (Fontana et al., 2017). It is contemplated that cells seeded on top of already aligned myotubes may lead to 3D tissue development as shown previously (Hume et al., 2012).

As mentioned previously, the demand for anisotropy in 2D cell culture doesn't only apply to myotubes, but also neurons (Basso et al., 2018), tendon derived cells (Foolen et al., 2018) and smooth muscle cells (Kuppan et al., 2016). In addition to these cells, the topography presented here may be used to further examine the influence of topographical cues on stem cells, for example (Wang et al., 2012).

This example provides a low cost, appealing and reproducible method for guided alignment of C2C12 myoblast. By longitudinally cutting the vascular bundle of decellularized celery, grooves with diameters ranging from 21.52 μm±5.0 (N=53.) to 38.50 μm±6.8 (N=31) were acquired. Following 10 days in growth media, the actin filaments and apex of nuclei were observed to be aligned in the direction of the grooves. Subsequently, after 5 days in differentiation media, the myoblast fused and expressed MHC. The 308.08±169.44 μm long myotubes were within −2.44°±3.83 (N=14) with respect to the direction of the vascular bundle/grooves.

Anisotropy is key characteristic of functional muscle tissue. Yet, in the laboratory, the oversimplified environment of 2D petri dishes fails to recreate in vivo directionality. It has been shown that aligned skeletal muscle cells upregulated troponin T, myosin heavy chain and myogenin on uniaxial grooves when compared to smooth Petridishes. In order to address this difference and further mimic in vivo conditions, a variety of methods have been shown to induce cell anisotropy. Yet these methods are often laborious and rely on specialized equipment. By longitudinally cutting the vascular bundle of decellularized celery, this example acquired grooves with the dimensions in the 20-100 μm range suitable for optimal alignment and fusion of muscle cells. The xylem (including cambium) was composed of 38.50 μm±6.86 wide channels, whereas the phloem was composed of 21.52 μm±5.0 wide channels. Following 10 days in growth media, the actin filaments and long axis of nuclei were observed to be parallel to the vascular bundle.

Subsequently, after 5 days in differentiation media, the myoblast fused and expressed MYHC. The 308.08±169.44 μm long myotubes were within −2.44°±3.83 (N=14) with respect to the direction of the vascular bundle/grooves. Cells were considered to be aligned if the normalized value was below 10°. In this example a highly accessible, appealing and reproducible method for guided cell alignment is provided. Although this example is focused on skeletal muscle, a variety of other cell types are also contemplated, as well as further functionalization and tunability of mechanical properties to further extend applicability.

Example 7—Liquid Isolation of Solid Microstructures from Plants—Methods for Preparing Scaffold Biomaterials and/or Subunits Therefor This example describes methods for liquid-based extraction/isolation of solid microstructures of interest from native and/or decellularized plant tissues. A treatment comprising a maceration solution comprising an equal ratio of acetic acid to hydrogen peroxide (8.7M acetic acid, 4.9M peroxide) is described. In the example data below, we demonstrate an example of an approach to isolating single cell structures from the flesh of apple. Depending on the goal of the procedure, optimal solutions, concentrations and times similar to that described elsewhere herein, such as those described for the extraction of plant bundles, may work similarly. In this example, an acid and peroxide solution was used, but it will be understood that salt solutions, acid solutions, and base solutions as described herein may also be employed, for example. Extraction procedures described herein, such as those of this example, may be designed to deconstruct plant tissues into underlying intact structures, which may then be utilized alone, or in combination with other plant materials, hydrogels, crosslinkers, etc., to produce composite materials for biomedical and/or food tissue engineering applications, for example.

The source material may be selected to have certain chemical and/or structural features. The intended application of the material will assist with determining suitable plant or fungus-based sources which may be used. In addition to the structural characteristics of the material, the relative abundance of the molecular components may be of particular interest. Moreover, different treatments may be used to extract certain portions or structures to attain specific architectures as well as mechanical and/or chemical profiles. These treatments may include, but are not limited to, osmotic shock, ionic complexes, acid treatment, base treatment, and temperature modifications. For example, certain acid treatment may be used to extract pectin polysaccharides. Alkaline treatment may be used to remove hemicelluloses, and bleaching (redox reactions) may be used to remove lignins under certain conditions. The extraction of certain elements may affect the mechanics and structure of the biomaterial. Moreover, exposure to different conditions, for example basic conditions at varying temperatures, may disrupt the crystal structure of cellulose and other plant polymers. The nanoscale features ultimately dictate meso- and macro-scale characteristics. This example shows an array of treatments on a subset of source materials. As will be understood, the approaches extend to other source materials as well.

Methods and Procedures for Isolating Intact Single Cells from Native or Decellularized Plant Tissues for the Production of Composite Biomaterials Example single plant cell extraction procedures from decellularized, and native, plant tissues are described hereinbelow. A maceration-based treatment for obtaining desired microstructures from plant tissue is described.

This approach may allow for the simple and automatable liquid-based extraction of specific microstructures of interest from plant tissue in order to build structured biomaterials, and may replace time consuming and/or manual approaches. Liquid-based extraction of solid structures is relatively quick (typically on the scale of minutes) and can be done in a beaker without manual work by a human operator. Large volumes of plant tissue may be treated in a single experimental run to isolate key microstructures in a reproducible fashion. Such approaches may also allow for tuning the chemical, structural, and/or mechanical properties of the microstructures based on the liquid treatment conditions (concentration, time, temperature, etc). Approaches described herein may substantially preserve or maintain 3-dimension microstructure, providing several advantages.

Approaches as described herein may provide for tunability of resultant products—which may be combined or customized by modifying the type of scaffold, how it is prepared, extracted, isolated, prepared, combined with other products (or not), in order to affect the texture or physical properties of the resultant biomaterial. The material may be macerated at room temperature and allowed to shake overnight, or can be done on a hot plate and heated to speed up the maceration process, for example Preparation of Maceration Solution for this Example 1. For Maceration, a 50 mL solution of a 1:1, ratio of glacial acetic acid to 30% hydrogen peroxide was prepared.

Preparation of Plant Tissues for this Example

2. Prepare strips of tissue by slicing off any skin or removing ends. For fruits like apples or pear, peel skin and slice into equal pieces.
3. Cut into 3 cm (or appropriate size) pieces, then slice on a mandoline slicer.
4. For fruits such as apple, pear and the like, use all of the inner pulp staying away from the core. For plants such as asparagus, celery and the like, keep slices containing visible vascular bundles of xylem and phloem.
5. At this point, the native tissues can be treated with the conditions described below. Alternatively, the native tissues can also first be decellularized according to the SDS-based methods already described in detail hereinabove prior to the additional treatments described below.
6. Remaining strips are placed in a beaker filled with the desired solution for microstructure isolation.

Extraction Procedure

Materials Used:

a. 50 mL tubes for each solution type and/or concentration
b. 200 mL beakers (recommended to use exact same beakers for entirety of procedure)
c. hot plate
d. thermometer
e. 4× lids from 6 well plate (or any clear rectangular plate lid for images)
f. 1×1 L beaker filled with distilled water (recommend having another beaker on the side to pour the 200 mL of distilled water into to stop the reaction quickly).
g. forceps
h. timer Procedure:

As will be understood, this procedure may be applied to any plant tissue. Here we present the results utilizing Apple or Pear.

For maceration at room temperature:

1. Obtain strips from the starting material and place in a 50 mL tube no more than half full. This can be scaled up into a larger size vessel as long as the amount of plant material is no more than half of the volume of maceration solution.
2. Add the 1:1 maceration solution (herein comprised of an equal v/v ratio of acetic acid to hydrogen peroxide –8.7M acetic acid, 4.9M peroxide)
3. Place on a shaker overnight at 120 RPM For maceration with heat:

1. Obtain several plant strips.
2. Prepare a beaker with the maceration solution.
3. Place the beaker on a hot plate in a fume hood.
4. Put the strips into the beaker, then increase the temperature of the hot plate to 100° C.
5. Once bubbles can be seen, start a timer for 30 minutes, (or desired intervals). Remove each beaker after 10, 15, 20 and 30 mins respectively, label all beakers.
6. After time is up, remove the beaker from the hot plate and add 200 mL of room temperature water (Caution: do not add cold water to the hot beaker as this could cause the glass to shatter—add slowly)
7. Using a thermometer, make 30 figure-8 turns through the sample thoroughly to gently separate cells from original pieces.

To clean the sample:

8. Pour out the solution without losing the sample. Plant pulp will be disrupted and present as individual cells or clumps of individual cells. Be sure to neutralize the solution before discarding.
9. Add cold water and perform several washes and centrifugations to remove any remaining maceration solution.
10. Perform 5×3 min centrifugations at 1000 RPM followed by decanting of the solution or supernatant. The plant materials will have formed a pellet at the top of the tube.
11. Decant and add more distilled water, then vortex or shake vigorously to resuspend.
12. To image cells, once washed, stain with 0.1% Congo red solution and examine under a fluorescent microscope.

Single Cell Isolation Results:

The treatment of a 1:1 (v/v) solution of acetic acid and hydrogen peroxide was used to macerate the apple-derived scaffolds. This was initially chosen as this formulation was found to be effective in separating key structures from more highly ordered plant tissues such as those found in the vascular tissues of celery and asparagus. Treatment of apple and pear tissues resulted in a solution of single pockets comprising individual structural cells, which once contained plant material. It is noted that although a 1:1 ratio of acetic acid to hydrogen peroxide was successful, other ratios are also expected to work. Additionally, it is contemplated that based on the desired characteristics of the material, the concentrations of solutions, ratios, temperatures and preparation times may be varied to successfully macerate the sample as well as the use of other solutions such as salts, other acids and bases. These pockets may be decellularized structural cells consisting of the cell wall of the plant cell, or the plant cell in its entirety or can be subsequently decellularized using previously described methods (using SDS and $CaCl_2$, such as described hereinabove). The resulting plant materials can then be combined with other materials and hydrogels to form composites, for example. It should be noted that some particles resemble the size of the plant cells and the plant cell walls in the natural and decellularized materials, but there are some that are larger. This may be due to swelling or several pockets isolated in a group or cluster.

Figure 28:
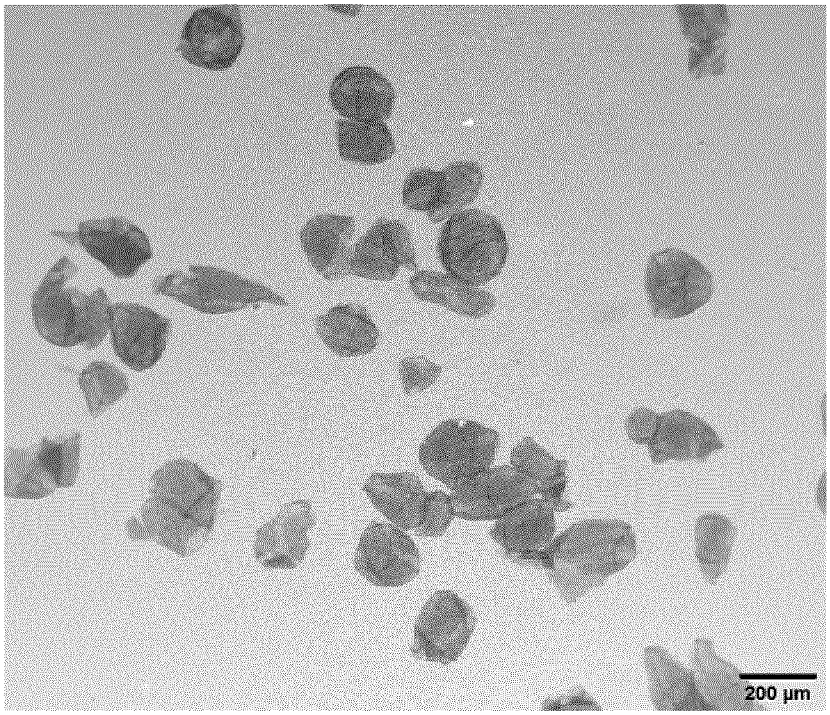
FIG. 28 shows an image of macerated decellularized apple hypanthium tissue stained in 0.1% congo red.
Figure 29:
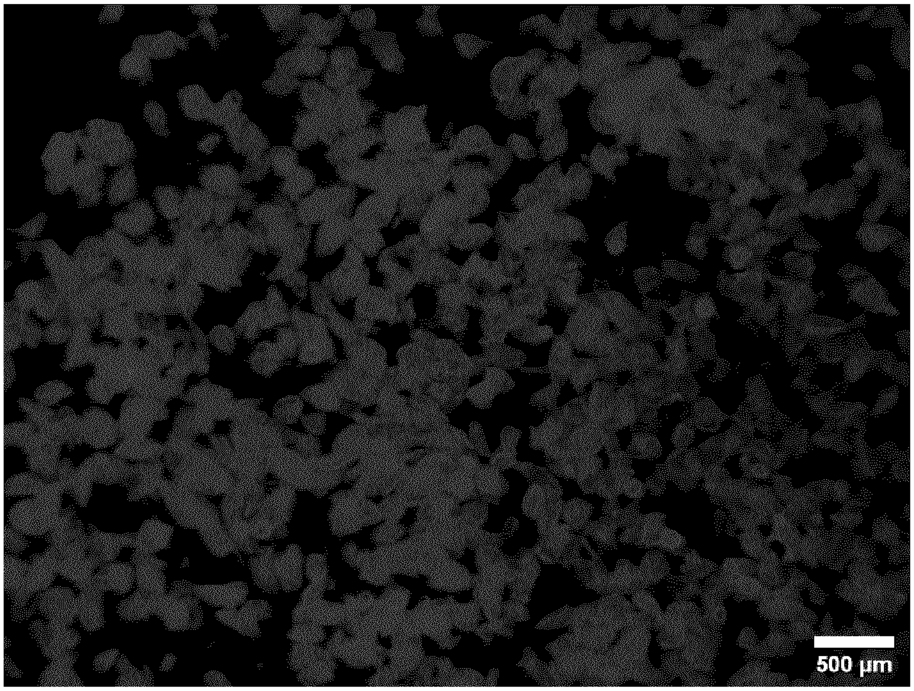
FIG. 29 shows an image of macerated decellularized apple hypanthium tissue in a 1% alginate matrix.

Maceration may be performed on plant cells that have been previously decellularized, or fresh samples. FIGS. 28-29 illustrate apple hypanthium which was macerated from fresh sample, and previously decellularized slices of apple hypanthium. The resulting cells appear to be morphologically similar aside from a difference in size. This could be as a result of the swelling of the fresh plant cell (prior to decellularization) in comparison to a decellularized plant cell.

Figure 32:
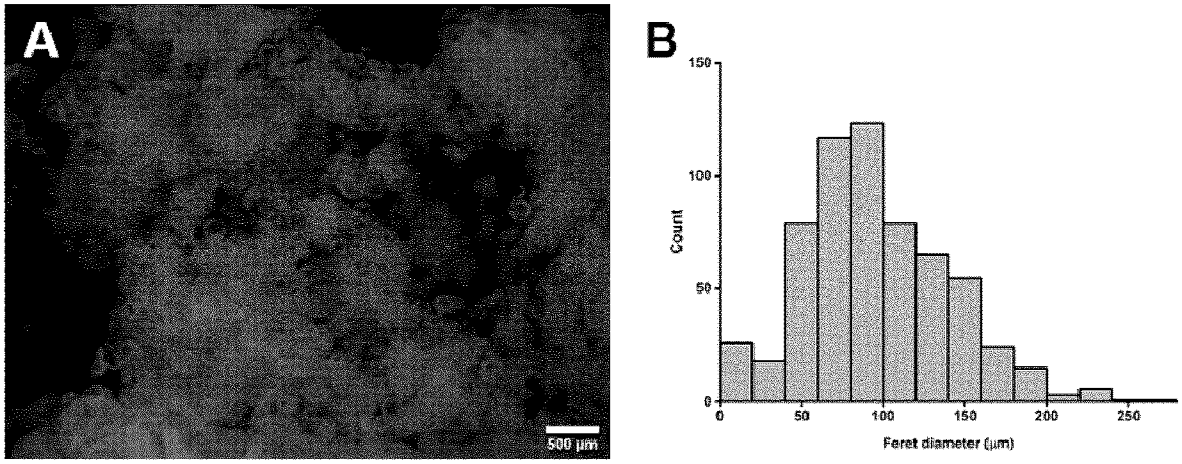
FIG. 32 shows (A) Decellularized pear hypanthium tissue macerated with a 1:1 mixture of acetic acid and peroxide; and (B) The particle size distribution. The particle size is 96.4±1.8 μm (mean±standard error)

Maceration using heat has also been shown to be successful as well as at room temperature. FIGS. 26-30 illustrate macerated samples obtained with shaking at room temperature overnight, whereas FIG. 32 illustrates macerated decellularized pear hypanthium obtained with boiling for 5 minutes. It can be seen that the tissue is still intact, however some larger pieces are beginning to separate. This is likely due to the short amount of boiling time. Boiling for longer than 10 minutes has been seen to begin separating the individual cells. These results show that extraction parameters can be controlled by varying both time and temperature. Certain structures or source materials may benefit from longer times or different temperatures to extract features of interest. Plants with less complex structures such as apple and pear, which consist mainly of pulp, yield primarily individual cells from maceration experiments. However, plants containing vascular bundles of varying degrees of ligno-cellulosic materials, may be extracted without macerating into individual structural cells.

The extracted materials may be incorporated into a hydrogel matrix or may be used alone, for example. The resulting material is observed to exhibit a gel-like form and may be used to serve as a hydrogel itself. The hydrogel may provide structural support and/or scaffolding. Moreover, it may be used to modify the rheological properties of the material, such as elasticity and viscosity. The addition of the hydrogel may also expand the chemical profile of the composite material.

Figure 26:
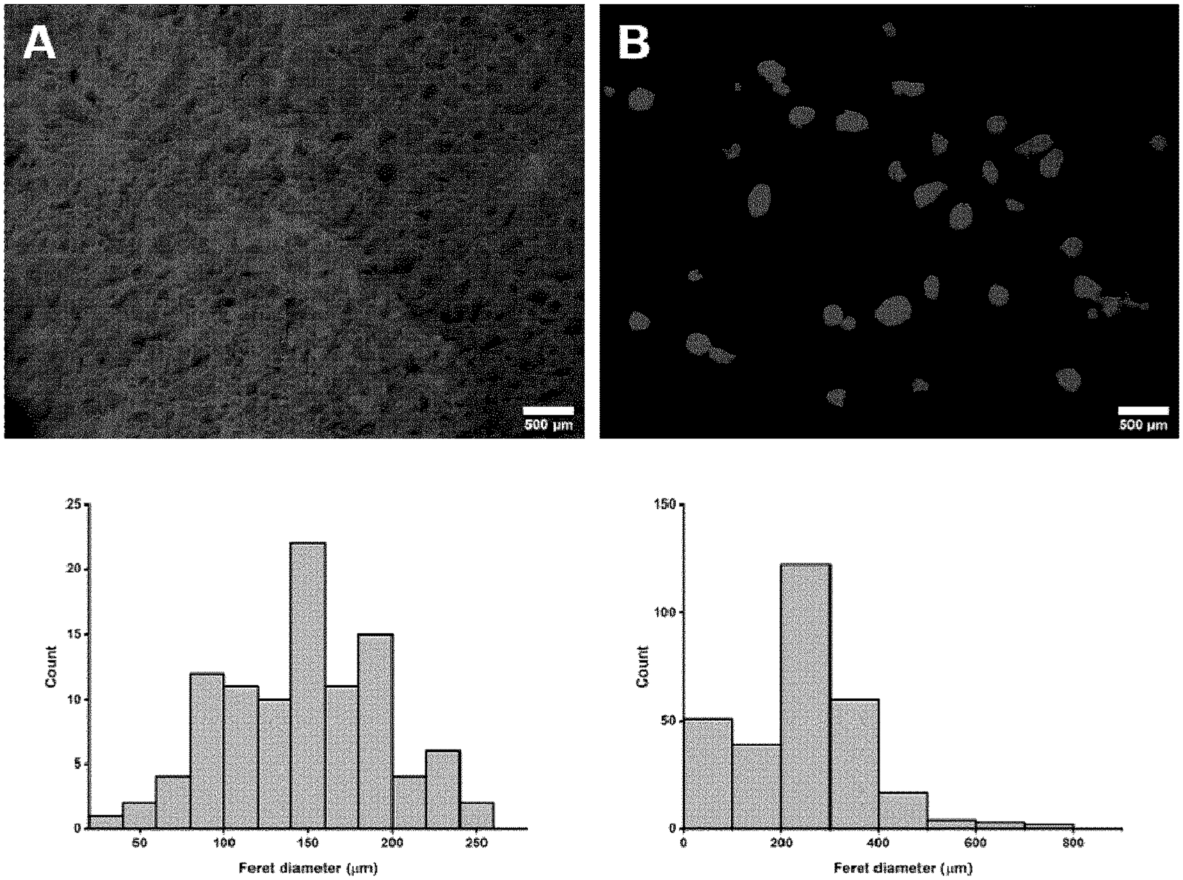
FIG. 26 shows (A) Decellularized apple hypanthium tissue and the pore size distribution; and (B) Particles obtained from maceration. The particle size is 241±8 μm (mean±standard error)

FIG. 26 shows images and pore size distribution analysis of decellularized apple hypanthium tissue (this is an untreated comparator of decellularized apple tissue with no salt/maceration/base/maceration treatment) (A), and images and pore size distribution analysis of the single celled structures obtained after maceration (B). The particle size is about 241±8 μm (mean±standard error). The results demonstrate that after deconstructing the intact apple hypanthium (A) into single celled components (B) the observed pore size increases significantly. Intact plant tissues are tightly constrained and isolating the tissue components allows for swelling and shape changes. This shows benefit to characterize the structural and mechanical properties of the resulting materials after maceration with slats, acids, bases or combinations thereof. As shown in other examples, the treatment conditions can impact the structural and mechanical properties of the isolated tissue structures.

Figure 27:
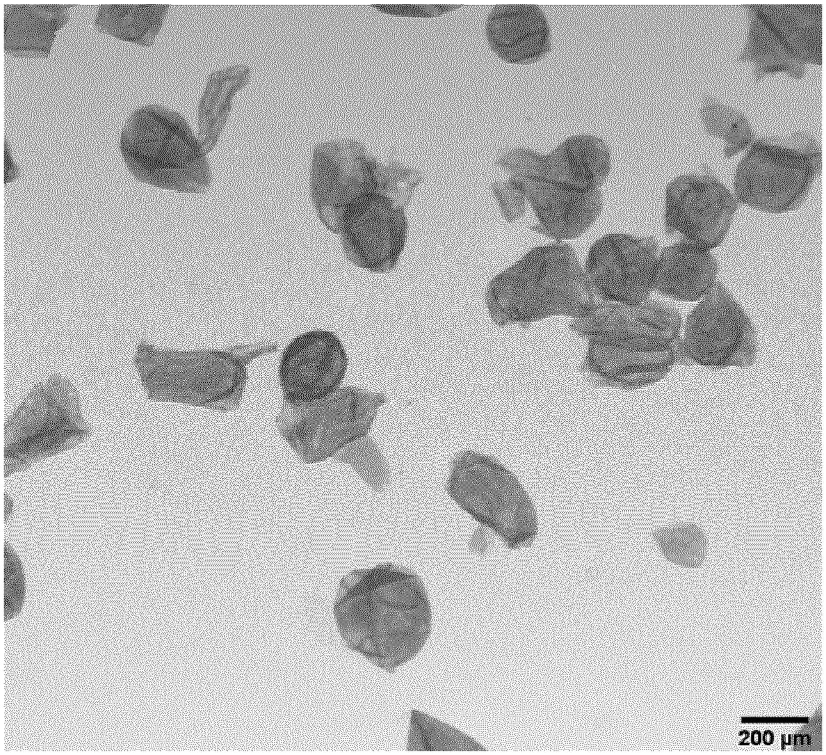
FIG. 27 shows an image of macerated fresh apple hypanthium tissue stained in 0.1% congo red.

FIGS. 27 and 28 show images of macerated fresh apple hypanthium tissue and macerated decellularized apple hypanthium tissue, respectively, stained in 0.1% congo red. In some applications (such as for food), disassembled plant tissues in single celled form, but containing intact plant cells, may contain nutritional benefit for resulting products, as well as providing a useful material in composite forms. In certain embodiments, these structures may be used for food applications where it is not desirable that all the native material is removed; however, by creating unique structural cells, the mechanics and composition may be tuned to meet the specific criteria for the application. That being said, the same material may simply serve as an intermediate, which may then be decellularized to produce the structural cells void of native material. This approach may be advantageous to increase the surface area to volume ratio and/or increase the decellularization efficiency. For biomedical applications, decellularized single celled particles are desirable for the creation of biocompatible biomaterials with low foreign body response, for example.

FIG. 29 shows an image of macerated decellularized apple hypanthium tissue in a 1% alginate matrix.

Figure 30:
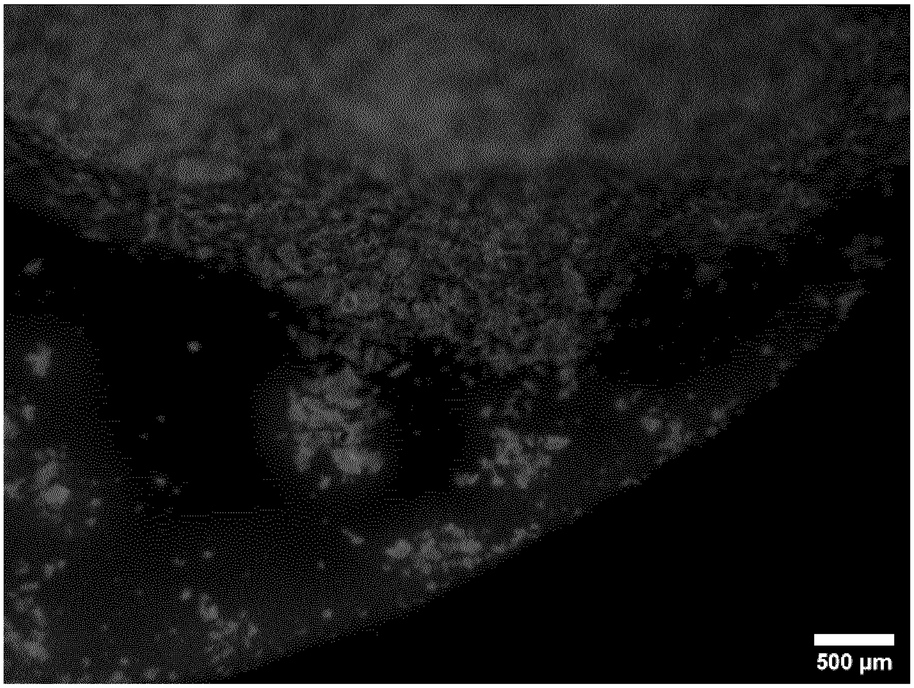
FIG. 30 shows an image of macerated ground particles made from decellularized apple hypanthium tissue in a 1% alginate matrix.

FIG. 30 shows macerated ground particles (grinding was performed on a Retsch grinder with an 80 micron filter in order to obtain a more homogenous distribution of particle sizes) made from decellularized apple hypanthium tissue in a 1% alginate matrix. The alginate matrix was produced by mixing alginate and water (mass/volume). The macerated material was then mixed with the 1% alginate solution by stirring.

Figure 31:
FIG. 31 shows examples of isolated apple cells derived through maceration of decellularized apple strips combined with 1% alginate to form a composite hydrogel.

FIG. 31 shows examples of isolated apple cells derived through maceration of decellularized apple strips combined with 1% alginate to form a composite hydrogel. The alginate matrix was produced by mixing alginate and water (mass/volume). The macerated material was then mixed with the 1% alginate solution by stirring.

FIG. 32 shows an image of decellularized pear hypanthium tissue boiled for 5 minutes in a maceration solution of a 1:1 mixture of acetic acid and peroxide (A), and corresponding particle size distribution results (B). The particle size was 96.4±1.8 μm (mean±standard error).

Results obtained from pear versus apple maceration could be as a result of the initial size of the fruit cells or the solutions and conditions used for maceration. Based on the desired product/application, any or all of these conditions may be fine tuned, down to the size of the cell, as desired.

Results from maceration studies indicate that maceration may be used to remove bundles/microchannel structures from AS and CL quickly and efficiently, in as little as 15 minutes in some experiments. Maceration may also be used to produce AA and PR “sauce” in as little as 5-10 minutes under some of the conditions tested. In certain embodiments, for example, maceration may involve allowing the solution to mix at least 12 hours at room temperature, or other embodiments such as boiling samples (at about 80-100° C.) in a maceration solution (such as, hydrogen peroxide and glacial acetic acid, at a 1:1 ratio), mixing/agitation/mechanical stimulation (i.e. using a stir bar, by hand, etc. . . . ) of the solution for a period of time (i.e. about 10-30 min), and washing away the maceration solution, may be used. Changes in these steps may be used to tune properties of the resultant products and/or extract specific components of the plant material.

Detailed studies and description of liquid-based extraction/maceration techniques for extracting one or more structures from plant or fungal tissue can also be found in PCT patent application no. PCT/CA2020/050654 entitled “High Density Microchannels”, which is herein incorporated by reference in its entirety.

Example 8—Methods for Chemically Crosslinking Chemically Treated Plant Tissues for Preparing Composite Biomaterials This Example describes methods for chemically crosslinking, using a linker molecule, that can be used to chemically bond collagen to decellularized cellulose scaffolds, generating composite biomaterials. The following studies were performed using decellularized apple, however it may be applied to generally any suitable isolated plant tissue, as described herein.

Step 1: Solvent and Sample Preparation

Solvent

Dimethylacetamide (DMA) was dried in the fume hood to remove water

Temperature: 115° C.

Time: 45 minutes

LiCl

LiCl was kept in the oven all times to prevent hydration.

Temperature: 210° C.

Samples

Decellularized apple—solvent exchange

Step 1. The apple pieces (already decellularized) were kept in ethanol or acetone for 20 minutes in an ultrasound bath. Three cycles of solvent exchange with ethanol were performed.

Step 2: The pieces of apple were immersed in DMA for 20 minutes in an ultrasound bath. Three cycles of solvent exchange with DMA were performed.

Step 2: Succinylation of Cellulose using DMA and LiCl

Scaffold: Mass of apple cellulose (after) solvent change=360 mg

Chemicals and Reagents:

DMA=30 mL

LiCl=271 mg

AS (succinic anhydride)=3.1 g

Conditions

Temperature: 80° C.

Duration: 6 h (under rotational agitation)

Figure 33:
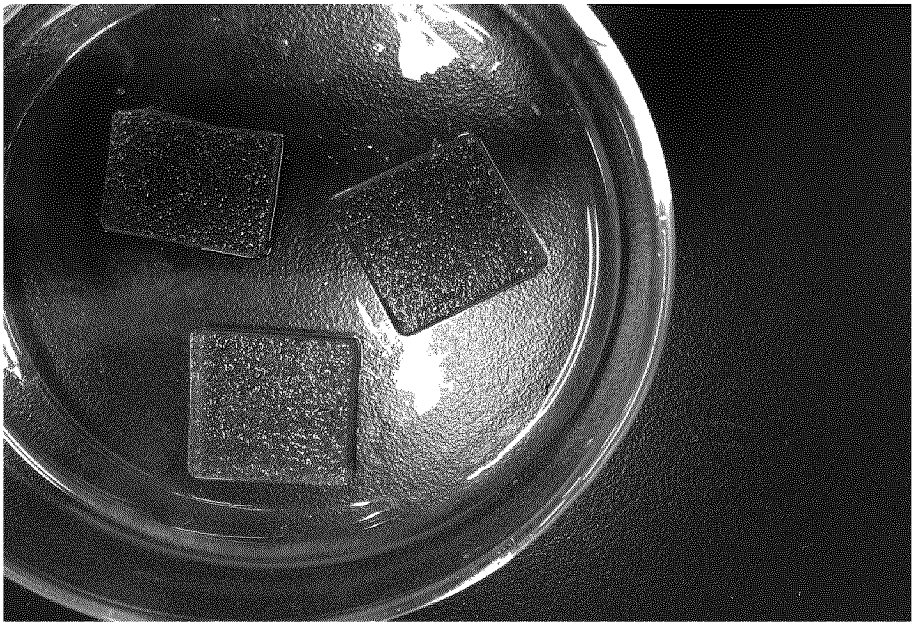
FIG. 33 shows an image of cellulose scaffolds after reaction in presence of succinic anhydride is complete, as described in Example 8.
Figure 34:
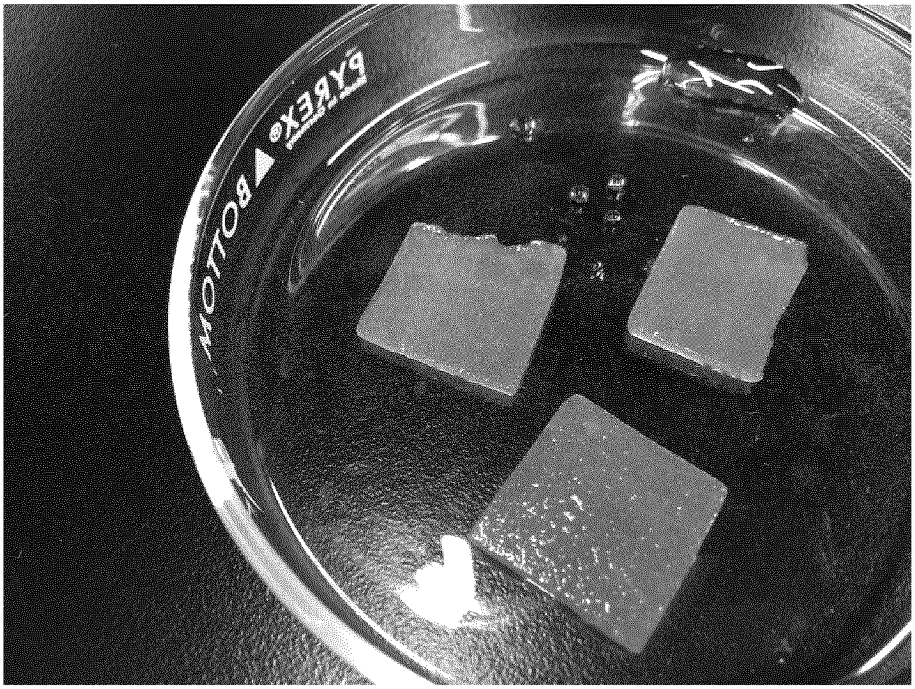
FIG. 34 shows an image of cellulose scaffolds of FIG. 33, after washing is complete, as described in Example 8.

After solvent preparation (DMA and LiCl) the cellulose pieces are immersed in DMA. The LiCl is then added. The mixture was stirred for 30 minutes. After 30 minutes, the succinic anhydride (AS) was added. The mixture is placed in the oven at 80° C. for 6 h. After this process, the solvent is removed, and the cellulose is washed intensely with water until the scaffold is clean and free of visible residue. FIGS. 33 and 34 show the cellulose immediately after the reaction, and after excessive washing, respectively.

Figure 35:
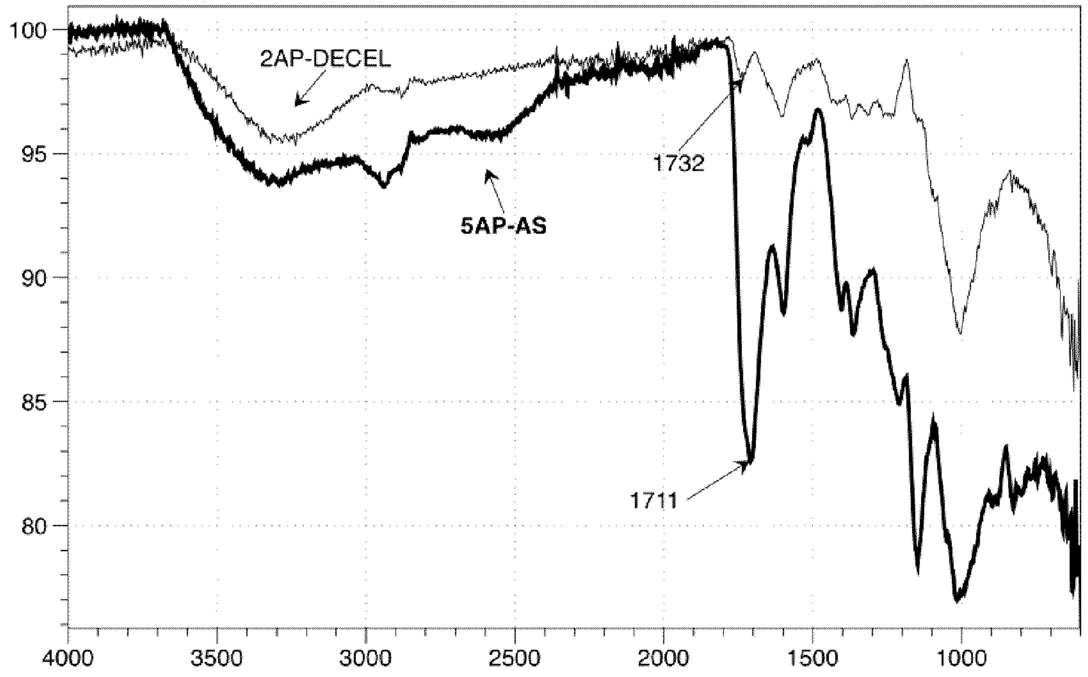
FIG. 35 shows FTIR spectra of decellularized scaffolds (2AP-DECEL) and the chemically bonded composite of succinylated plant-derived cellulose (5AP-AS), as described in Example 8.

In order to confirm the chemical crosslinking was accomplished, Fourier Transform Infrared Spectroscopy was used (See FIG. 35). The spectral shifts revealed that the succinic anhydride was successfully chemically bonded to the scaffold. This linker molecule may be used to attach other molecules such as collagen, and/or for a variety of other couplings, conjugations, and/or crosslinkings, as will be known to the person of skill in the art having regard to the teachings herein.

Example 9—Composite Scaffold Biomaterials for Food Tissue Engineering

World meat consumption is projected to be unsustainable in the next few years. As the current population exceeds 7 billion people, it is expected that meat consumption will double by 2050 according to a study from the University of Oxford (2018). The United Nation's Food and Agriculture Organization reports that 26% of the planet's ice-free land is used for livestock grazing, and 33% of croplands are used for livestock feed production. Maintaining livestock negatively impact the environment in three ways. Firstly, large amounts of methane are released into the atmosphere. It is estimated that livestock contribute to 7% of the total greenhouse gas emissions through enteric fermentation and manure. Secondly, deforestation to make room for fields has a significant environmental impact. Finally, a large amount of water is needed for each animal and for the production of livestock feed (Tullo, E. Finzi, A, and Guarino, M. 2019. Review: Environmental impact of livestock farming and Precision Livestock Farming as a mitigation strategy. Science of the Total Environment. 650: 2, pp 2751-2760.).

There are currently two competing types of livestock-free meats on the market: lab-grown meat (or cultured meat/synthetic meat) which grow animal cells onto scaffolds, and plant-based meats (such as those of Beyond Meat and Impossible Foods) which claim to contain no animal products.

The present inventors recognized that production of lab-grown meats may involve, for example, the growth of different cell types including muscle cells, fat cells and/or collagen on a scaffold supplemented with nutritional media grown inside a bioreactor, where the cells can easily multiply. This is an attractive method of producing meat, as it can be made healthier during production by modifying various factors such as raising the protein content, lowering saturated fat levels and/or enhancing vitamin content, for example. Benefits may also include the decrease in land deforestation, required water inputs and greenhouse gases.

This example describes the development of plant-derived meat-free scaffolds, which may be combined with animal or animal-free cells or sera, providing a customizable, tunable scaffold onto which any desired material may be added. Varying plant tissues may also be used, and may be combined to tune texture/mouth feel of the final product. The results herein represent an application of the techniques described above.

Isolation of Components:

Isolation of the plant material may be based on the material being used. Two different categories of materials used for excision of components are described below. From celery and asparagus, the vascular bundles (xylem and phloem) have been extracted from the rest of the plant, and the bundles were decellularized. Whereas from apple and pear, the preparation of the decellularized plant pulp from underneath the skin, excluding seeds, was performed.

Celery and Asparagus—Vascular Bundles:

Vascular bundles were extracted from celery by first removing the bottoms of each bundle (white portions) and cutting off tops where stalks branch off and contain leaves. Stalks were then cut into 1-inch segments and sliced on a mandolin into thin 1 mm sections. Slices containing no visible vascular bundles were discarded. A similar process was used for the removal of asparagus bundles whereby the bottoms and tops (where the number of scales increases above 2 around the circumference of the spear) are removed. Once slices of celery or asparagus were extracted, vascular bundles were removed by cutting them out of the slice with a razor or microtome blade. An alternative method of bundle extraction for celery involves breaking the 1-inch pieces of celery (unsliced) along the spine of the piece and peeling back the rest of the tissue, exposing the bundles. Celery bundles are relatively tough and can withstand being pulled away from tissue and can therefore be easily extracted. Once bundles are extracted, they were decellularized using methods as already described in detail hereinabove and/or in WO2017/136950, entitled "Decellularised Cell Wall Structures from Plants and Fungus and Use Thereof as Scaffold Materials", herein incorporated by reference in its entirety.

Apple and Pear—Pulp:

A similar process was used to excise apple and pear pulp from the fruit. First, the fruit was peeled using a peeler and sliced on a mandolin kitchen slicer. Pieces were either cut or used as whole slices while avoiding or removing the core and seeds. Slices were then decellularized as above.

Alternative Method of Extraction—Maceration

As an alternative to cutting and slicing, celery and asparagus bundles may be extracted through maceration. This may involve the use of a solution of glacial acetic acid and hydrogen peroxide; however, the concentration of these components may be altered. Maceration techniques may be adapted from those described hereinabove, and in Example 7 above. As well, vascular bundle extraction techniques may include those described in U.S. provisional application No. 62/847,771 entitled "High-Density Microchannels" and/or PCT patent application no. PCT/CA2020/050654 entitled "High-Density Microchannels", each of which are herein incorporated by reference in their entireties.

Chemical Treatments for Maceration:

Vascular Bundles:

Conventional maceration in the food industry typically attempts to soften or break down food using a variety of liquids such as acids or alcohols, to make extracts.

In the present studies, a tailored maceration-type procedure was developed and performed as follows:

1. Celery was cut into 1-inch pieces followed by slicing on a mandolin kitchen slicer;

2. ~50-60 Pieces were placed in a 1L beaker filled to the top with maceration solution (see treatment solutions 1-7 below) until all slices were covered.

3. The solution was brought to a boil (9-100° C.) and was mixed thoroughly every 5 minutes.

4. Bundles began separating from the rest of the strip after 10 minutes of boiling.

5. After maceration was completed, samples were removed from macerating solution and are washed several times with distilled water until acetic acid and peroxide was removed.

Figure 36:
FIG. 36 shows macerated CL in diluted acetic acid and peroxide boiled for 15 minutes, as described in Example 9.

It was observed that after increased boiling times, more bundles were seen to separate from the rest of the slice, however bundles were observed to soften due to increased boiling time. Images of macerated CL in diluted acetic acid and peroxide boiled for 15 minutes are shown in FIG. 36.

Additionally, a variety of solutions were tested for their potential as macerating products. These included:

Treatment Solution 1: 1:1 glacial acetic acid and 30% hydrogen peroxide

Treatment Solution 2: 1:1 glacial acetic acid and peroxide (as above), diluted 50% in water Treatment Solution 3: Glacial acetic acid Treatment Solution 4: 50% diluted acetic acid Treatment Solution 5: 95% ethanol Treatment Solution 6: 3 Molar Sodium Chloride (NaCl)

Treatment Solution 7: 4 Molar Hydrochloric Acid (HCl)

Of these treatments, only Treatment Solution #s 1, 2, 4, 6, and 7 were able to remove bundles, however the concentrated hydrochloric acid broke down the bundles beyond the point of use and chopped up the individual pieces, therefore the treatment condition was too strong. It was therefore diluted two-fold for subsequent testing.

Figure 37:
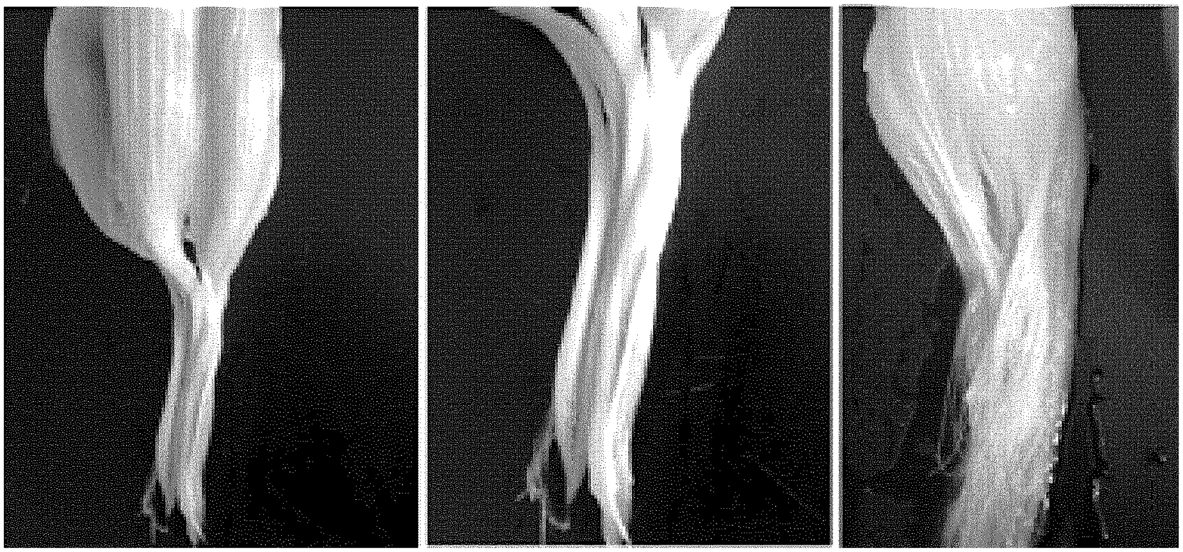
FIG. 37 shows macerated celery with only xylem and phloem strands visible.

It was also seen that celery and asparagus did not require slicing or prior preparation of the sample prior their addition into maceration solution. For these two, once samples were removed from the macerating solution, a significant amount of mixing was performed to excise bundles from pieces. The celery and asparagus were soft enough that the surrounding tissue could be squeezed off from the bundles (in celery with much more ease than asparagus). The long fibers were removed from the solution and placed into a new beaker with distilled water. The bundles were then cleaned with vigorous mixing and manual squishing of the sample while avoiding destruction of the bundles. Increasing amounts of surrounding tissue were removed after each wash with mixing (FIG. 37).

As will be understood, a decellularization step (such as an SDS-based decellularization as described herein) may be performed either before or after the liquid extraction/maceration step, if/as desired.

Figure 38:
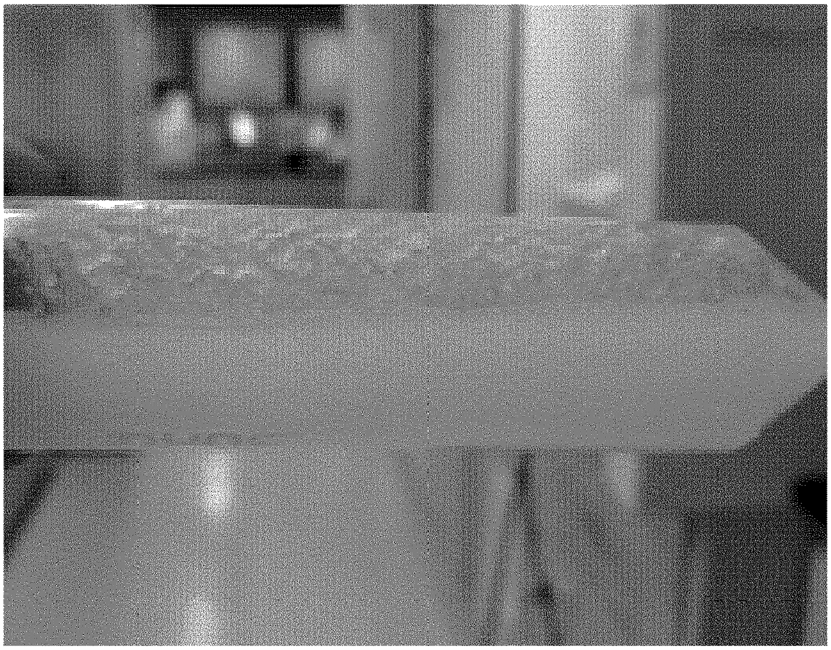
FIG. 38 shows macerated apple solution boiled in 1:1 glacial acetic acid and 30% hydrogen peroxide for 15 minutes as described in Example 9.

Macerated Pulp:

When the apple and pear fruits were macerated in treatment solution 1 as above and boiled for at least 10 minutes (prior to decellularization), the slices of fruit were separated into individual structural cells (or small clusters of structural cells). Previously decellularized apple was macerated using these conditions, and compared to freshly prepared apple (i.e. non-decellularized) macerated under the same conditions, and no significant difference was noted between each sample aside from the average size of the cells, which was larger in the fresh apple sample compared to the previously decellularized samples. In certain embodiments, the structural cells may comprise 3D hollow structures. Once samples were cleaned of macerating solution with several centrifugations with distilled water, a pellet resulted, which when resuspended with smaller amounts of water, formed a kind of goo (see FIG. 38).

Assembly of Components

Once samples were prepared, pieces were held together with adhesives such as alginate, in varying concentrations. Additionally, samples were also able to be dried down until no moisture remained and were even lyophilized to ensure drying or were able to be used as individual slices with cells seeded onto them and layers assembled into stacks (i.e. a basic type of complementary/interlocking geometry).

Examples of Available Formats:

Alginate Composites:

Once prepared, varying concentrations of bundles or slices of fruit pulp were assembled with alginate by varying either the concentration of plant material (1:4, 1:1, 4:1 plant material: 1% alginate by volume, the 1% alginate being a 1% w/v prepared solution, then this mixture is added to the plant material in the indicated ratios (e.g. 1:4 w/w, etc.)) or the concentration of alginate (0.25, 0.5, 0.75, 1.0, 2.0, 3.0% alginate w/v). These were then mechanically tested for their bulk moduli before and after cooking. Samples were also fired and the bulk moduli assessed before and after cooking to examine the change in texture after cooking in efforts of mimicking the effects of meat.

Figure 39:
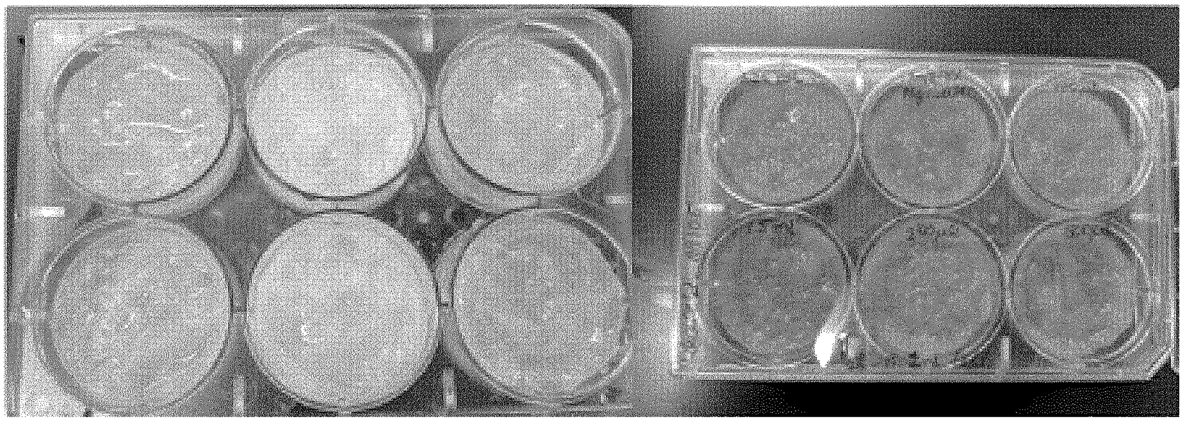
FIG. 39 shows decellularized asparagus bundles, celery bundles (left), and apple slices (right) cross-linked with sodium alginate in varying concentrations.
Figure 40:
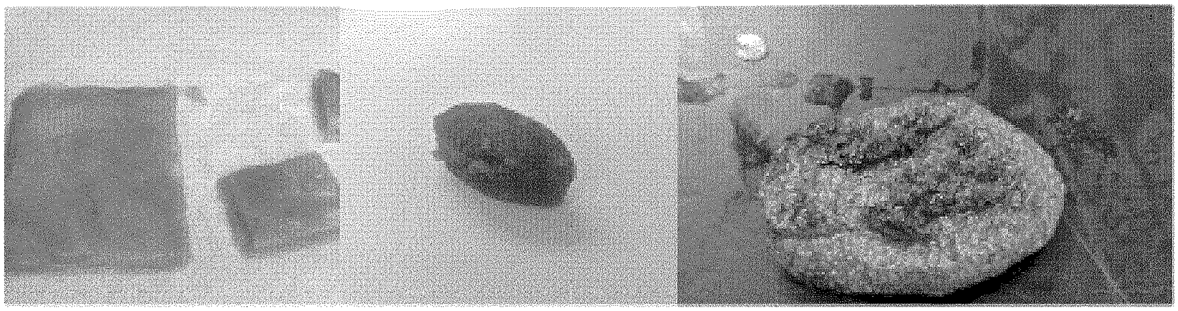
FIG. 40 shows decellularized apple slices (left) and apple powder (center and right) crosslinked with alginate. Centre and right images are the same apple "meatball" before and after frying.
Figure 46:
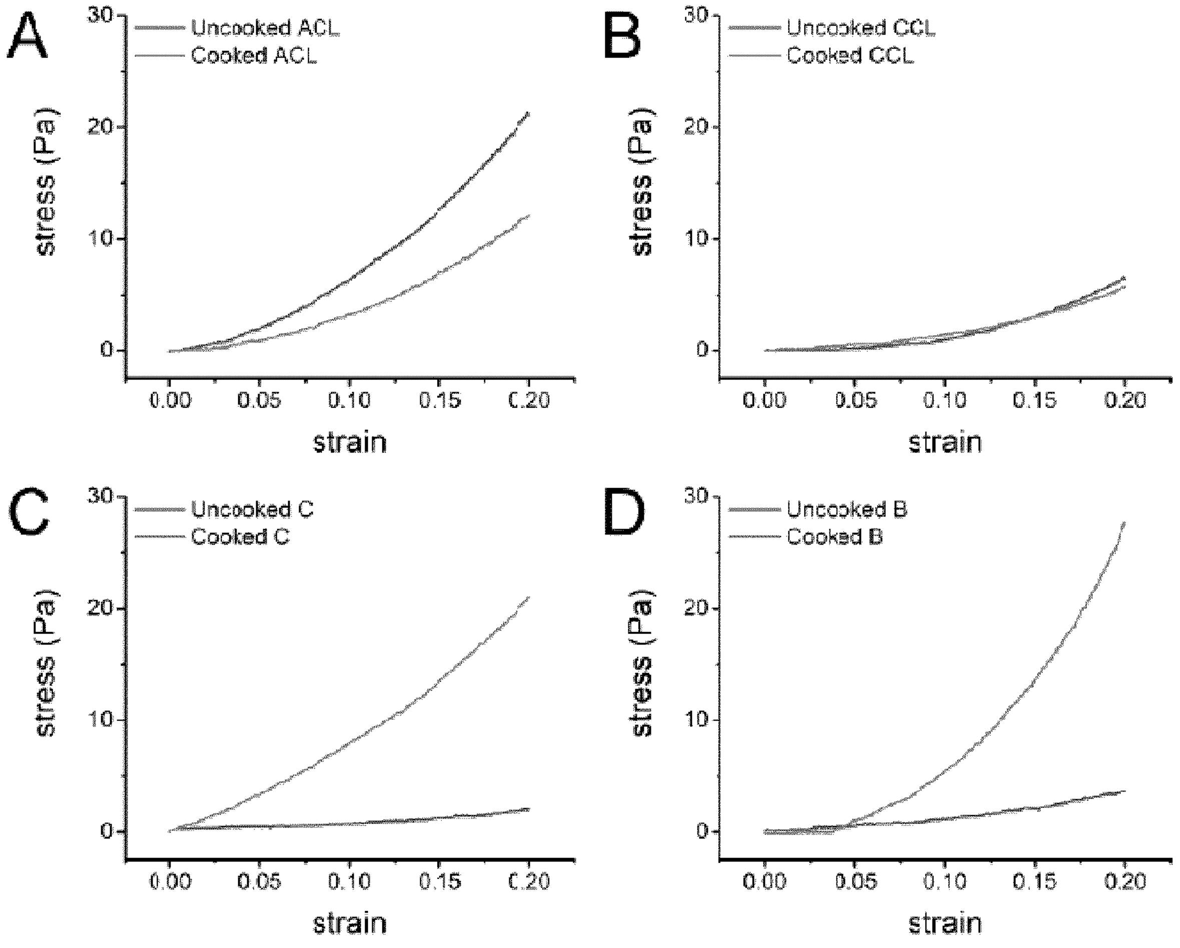
FIG. 46 shows comparison of stress/strain curves comparing results from cooking meat with cooking alginate-celery "mini burgers". Representative stress/strain curves for individual samples of uncooked (red) and cooked (gray) plant-based meat and real meat are shown. (A) shows ACL (Alginate-celery) plant-based meat, which softened after cooking. (B) shows that alternatively, CCL (Cell-cultured celery) plant-based meat did not significantly change their mechanical properties before or after cooking. (C) shows stress/strain curves for chicken breast (C) which became significantly stiffer after cooking, and a similar trend was observed for beef (B) steaks in which the samples became significantly stiffer after cooking (D)

FIG. 39 shows decellularized asparagus bundles, celery bundles (left) and apple slices (right) cross-linked/glued with alginate in varying concentrations. FIG. 40 shows decellularized apple slices (left) and apple powder (centre and right) crosslinked/glued with alginate. Center and right images are the same apple "meatball" before and after frying. Powder may be generated from lyophilized material that has been decellularized, which may be ground and/or filtered to particular sizes, for example ground with an 80 micron filter, FIG. 46 shows comparison of stress/strain curves comparing results from cooking meat with cooking alginate-celery "mini burgers". An increase in stiffness of meat was observed as a result of cooking, while no change in stiffness was observed from cooking the alginate-celery composites. FIG. 46(A) shows representative stress/strain curves for individual samples of uncooked (red) and cooked (gray) plant-based meat and real meat. (A) shows ACL plant-based meat, which softened after cooking. (B) shows that alternatively, CCL plant-based meat did not significantly change their mechanical properties before or after cooking. (C)

shows stress/strain curves for chicken breast (C) which became significantly stiffer after cooking, and a similar trend was observed for beef (B) steaks in which the samples became significantly stiffer after cooking (D).

Figure 47:
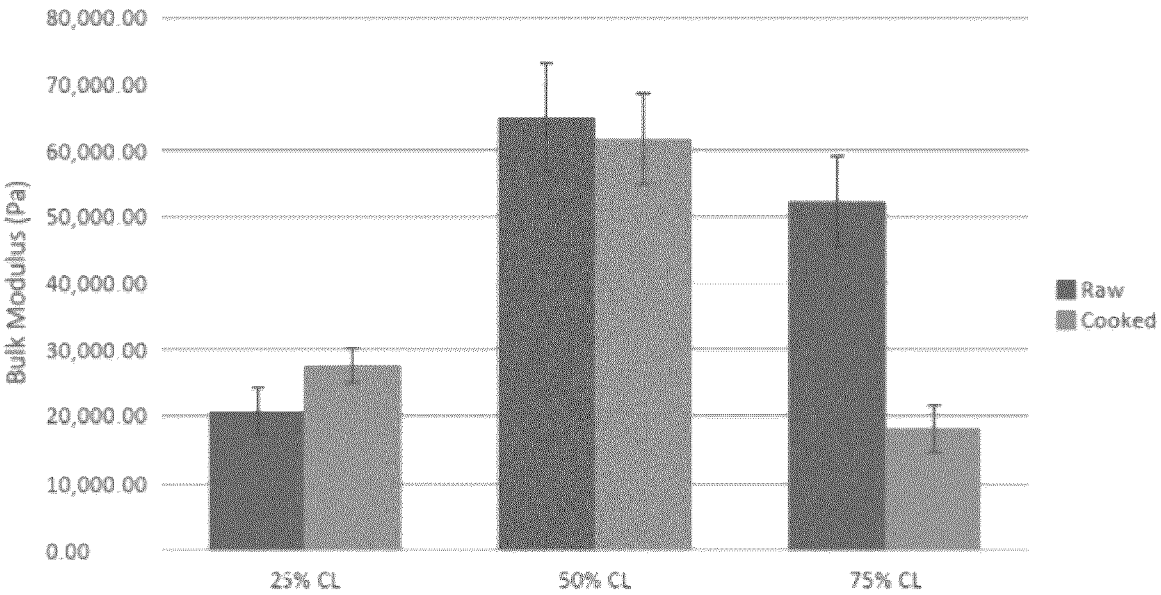
FIG. 47 shows bulk moduli from 3 10 cm CL burgers with varying concentrations of CL: alginate (N=10).

FIG. 47 shows that cooking CL-based burger mimics did not significantly affect the stiffness of the burger, aside from higher concentrations of CL. These results are interesting because very low amounts of alginate in CL strips cause an increase in stiffness after cooking.

Figure 41:
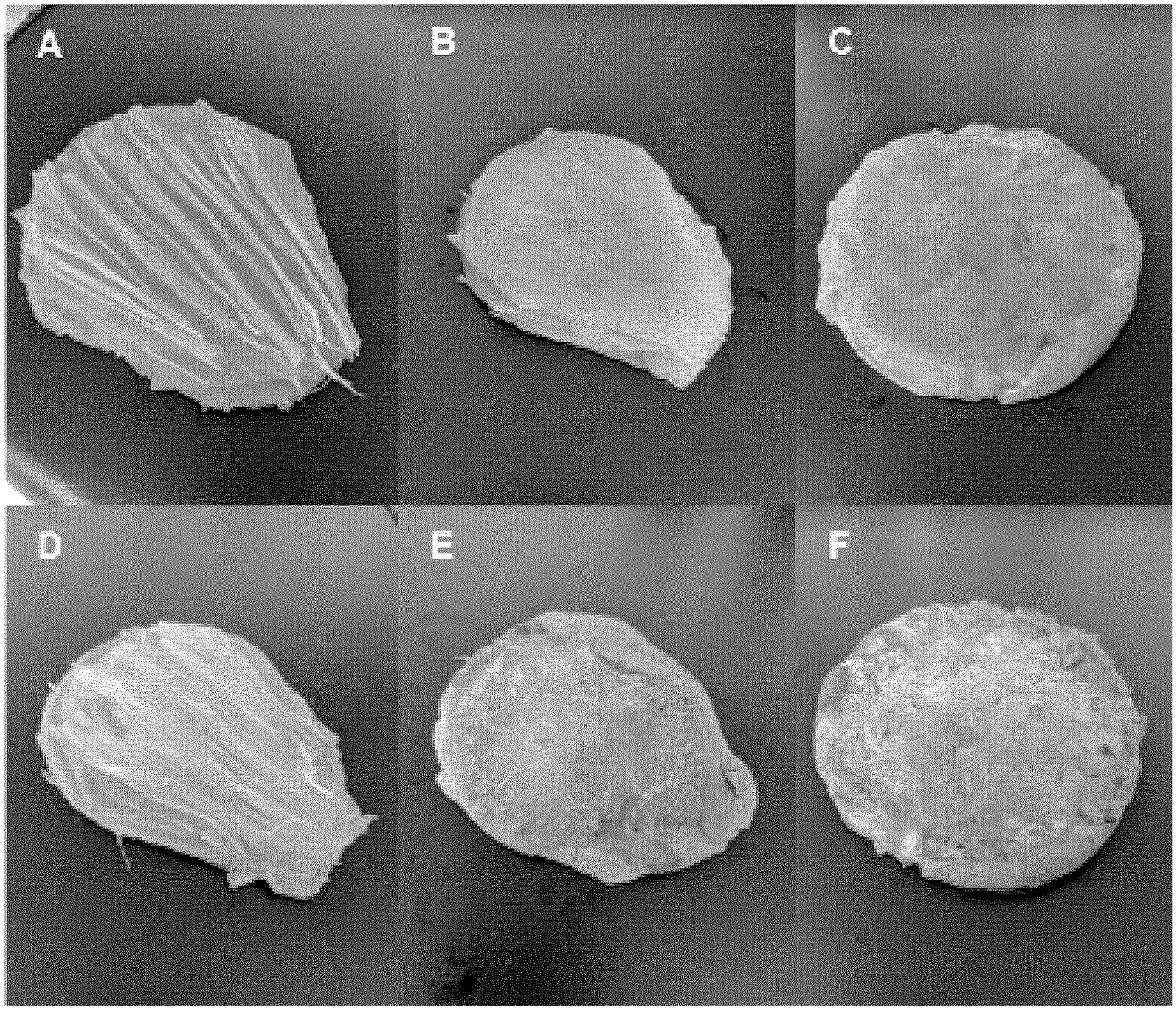
FIG. 41 shows decellularized pear slices. (A) shows uncooked pear with celery bundles, (B) shows uncooked pear without celery bundles, (C) shows uncooked pear "burger", (D) shows cooked pear with celery bundles (top layer removed), (E) shows cooked pear without celery bundles, and (F) shows cooked pear "burger", as described in Example 9.

Composites:

Various samples were also able to be combined in various conditions, e.g. CL (celery) strips with AA (apple) powder, CL (celery) strips with AA (apple) strips, or CL VBs with AA or PR (pear) etc., as described. FIG. 41 shows several examples of composites which have been developed to change/adjust mechanical properties when combined and change the texture of the material when eaten. An advantage of such an approach is to enhance the tunability of the resulting product. For example, adding CL bundles to stacks of apple or pear may give the product a stringy texture when biting into it, which is suggested to resemble the muscle fibers of real meat, for example.

FIG. 41 shows decellularized pear slices. (A) shows uncooked pear with celery bundles, (B) shows uncooked pear without celery bundles, (C) shows uncooked pear "burger", (D) shows cooked pear with celery bundles (top layer removed), (E) shows cooked pear without celery bundles, and (F) shows cooked pear "burger" images. Pear and celery were stacked in these examples without gluing.

Cell-Cultured Synthetic Meat:

Decellularized scaffold strips made from asparagus, celery, apple or pear were used to seed muscle and fibroblast cells in the hollows left over from the plant cells. After two weeks, once cells had reached a desired confluency of growth onto the individual strips, they were stacked and cooked for mechanical testing—this was done to represent the effects of chewing (FIGS. 42 and 43).

Figure 42:
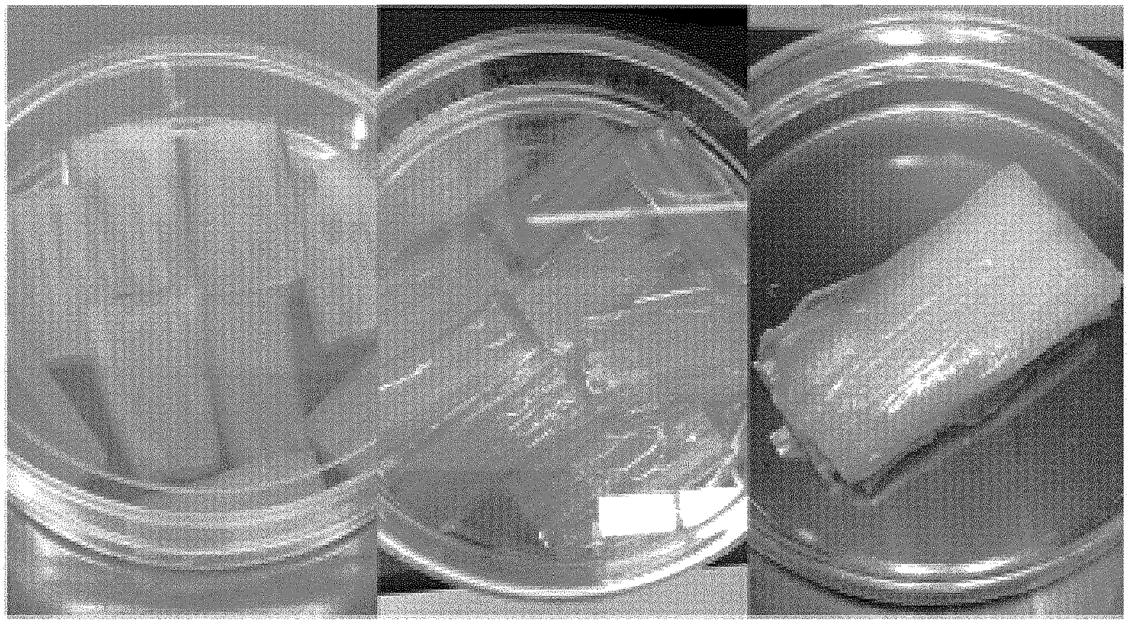
FIG. 42 shows decellularized celery strips (left) seeded with muscle cells (center) and stacked and crosslinked with alginate solution (right)
Figure 43:
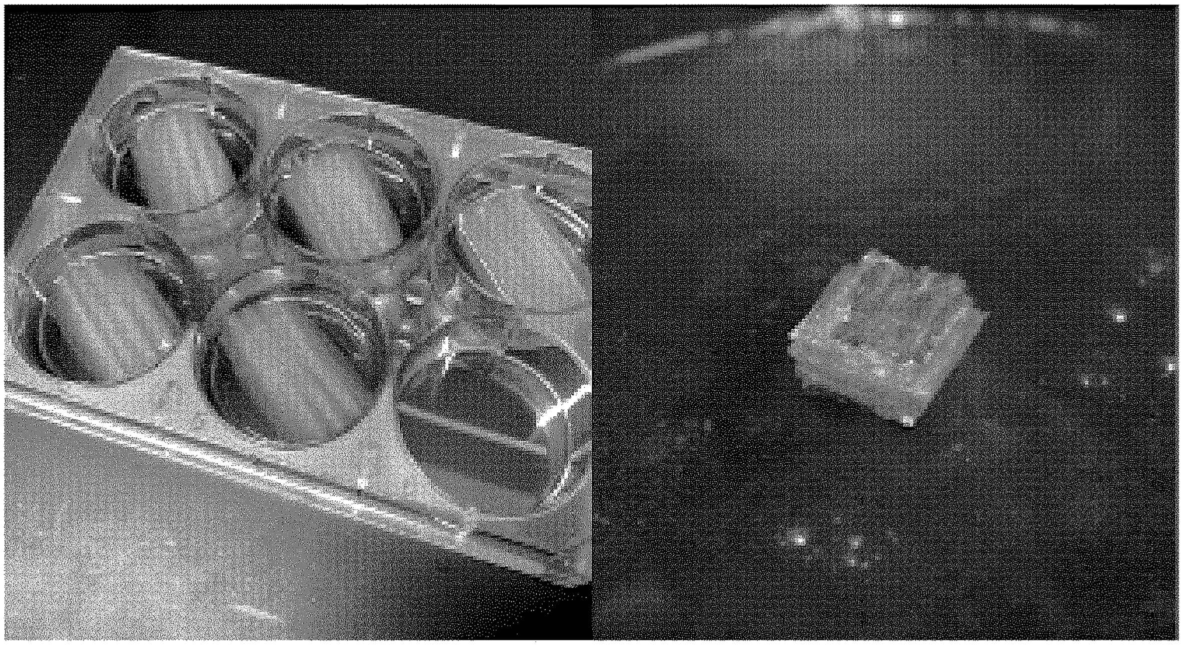
FIG. 43 shows stacks of decellularized celery in alternating layers of muscle cells and fat cells (left) then stacked and fried on a cast-iron drying pan (right)

FIG. 42 shows decellularized celery strips (left) seeded with C2C12 muscle cells (center) at a density of $2\times10^6$ every second day, for 7 days, then stacked and crosslinked with alginate solution (right). FIG. 43 shows stacks of decellularized celery in alternating layers of muscle cells and fat cells (left), then stacked and fried on a cast-iron drying pan (right).

Figure 44:
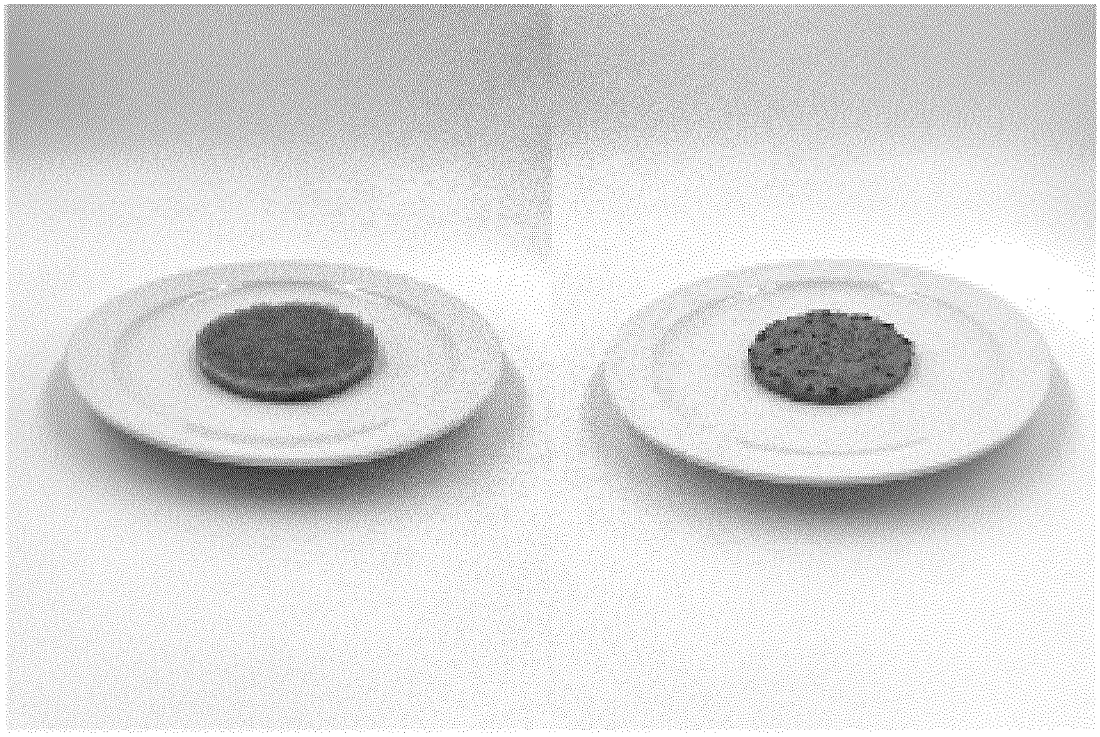
FIG. 44 shows plant-based AA meat-free "burger patty" raw (left) and pan-fried (right) held together with 1% alginate.
Figure 45:
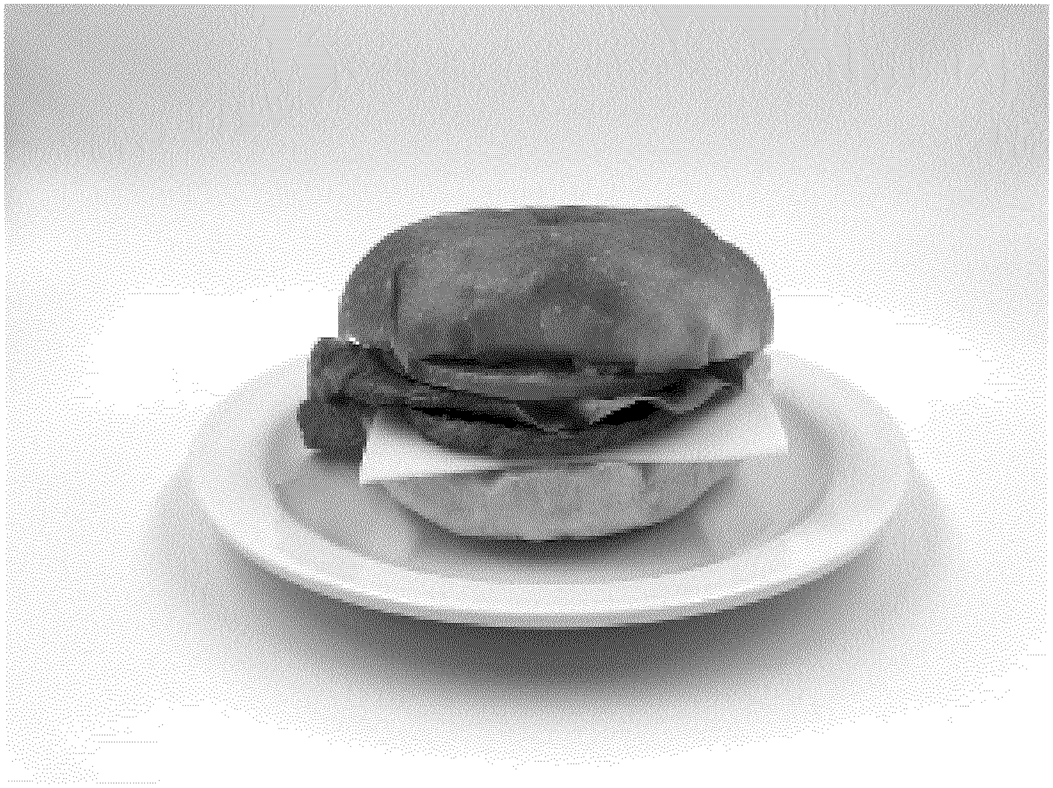
FIG. 45 shows a burger product prepared from the patty of FIG. 44.

All these samples were able to be cooked (e.g. fried, baked, etc.), and can be customized. Therefore, results for these products show immense customizability, and offer new avenues in the plant-based meat industry. By way of example, FIG. 44 shows a plant-based AA meat-free "burger patty" raw (left) and pan-fried (right), held together with 1% alginate, and FIG. 45 shows a burger product prepared from the patty of FIG. 44. The results described herein indicate that scaffold biomaterial approaches detailed herein may provide large scale scaffolds that provide texture, mouth feel, and/or mechanical properties similar to full cut meat.

One or more illustrative embodiments have been described by way of example. It will be understood to persons skilled in the art that a number of variations and modifications can be made without departing from the scope of the invention as defined in the claims.

REFERENCES

Antoni, D., Burckel, H., Josset, E., & Noel, G. (2015). Three-dimensional cell culture: A breakthrough in vivo. International Journal of Molecular Sciences, 16(3), 5517-5527. doi:10.3390/ijms16035517

Altomare, L., Gadegaard, N., Visai, L., Tanzi, M. C., & Fare, S. (2010). Biodegradable microgrooved polymeric surfaces obtained by photolithography for skeletal muscle cell orientation and myotube development. Acta Biomaterialia, 6(6), 1948-1957. doi:10.1016/j.actbio.2009.12.040

Basso, J. M. V., Simon, M., & Staii, C. (2018). Neuronal dynamics on patterned substrates measured by fluorescence microscopy. MRS Communications, 8(2), 487-492. doi:10.1557/mrc.2018.52

Brown, R. B., & Audet, J. (2008). Current techniques for single-cell lysis. Journal of the Royal Society Interface, 5(Suppl 2), S131. doi:10.1098/rsif.2008.0009.focus Camelliti, P., Kohl, P., McCulloch, A. D., & Gallagher, J. O. (2006). Micropatterned cell cultures on elastic membranes as an in vitro model of myocardium. Nature Protocols, 1(3), 1379-1391. doi:10.1038/nprot.2006.203

Chal, J., & Pourquié, O. (2017). Making muscle: Skeletal myogenesis in vivo and in vitro. Development (Cambridge, England), 144(12), 2104. doi: 10.1242/dev.151035.

Charest, J. L., Garcia, A. J., & King, W. P. (2007). Myoblast alignment and differentiation on cell culture substrates with microscale topography and model chemistries. Biomaterials, 28(13), 2202-2210. doi:10.1016/j.biomaterials.2007.01.020

Clark, J. F., & Pyne-Geithman, G. (2005). Vascular smooth muscle function: The physiology and pathology of vasoconstriction. Pathophysiology, 12(1), 35-45. doi:10.1016/j.pathophys.2005.02.007

Cooper, A., Jana, S., Bhattarai, N., & Zhang, M. (2010). Aligned chitosan-based nanofibers for enhanced myogenesis. Journal of Materials Chemistry, 20(40), 8904. doi:10.1039/c0jm01841d Courtenay, J. C., Deneke, C., Lanzoni, E. M., Costa, C. A., Bae, Y., Scott, J. L., & Sharma, R. I. (2018). Modulating cell response on cellulose surfaces; tunable attachment and scaffold mechanics Cellulose, 25(2), 925-940. doi:10.1007/s10570-017-1612-3

Courtenay, J. C., Johns, M. A., Galembeck, F., Deneke, C., Lanzoni, E. M., Costa, C. A., . . . Sharma, R. I. (2017). Surface modified cellulose scaffolds for tissue engineering. Cellulose, 24(1), 253-267. doi:10.1007/s10570-016-1111-y Dowling, D. P., Miller, I. S., Ardhaoui, M., & Gallagher, W. M. (2011). Effect of surface wettability and topography on the adhesion of osteosarcoma cells on plasma-modified polystyrene. Journal of Biomaterials Applications, 26(3), 327-347. doi:10.1177/0885328210372148

Engler, A. J., Griffin, M. A., Sen, S., Bonnemann, C. G., Sweeney, H. L., & Discher, D. E. (2004). Myotubes differentiate optimally on substrates with tissue-like stiffness: Pathological implications for soft or stiff microenvironments. The Journal of Cell Biology, 166(6), 877-887. doi:10.1083/jcb.200405004

Fang, Y., & Eglen, R. M. (2017). Three-dimensional cell cultures in drug discovery and development. Slas Discovery, 22(5), 456-472. doi:10.1177/1087057117696795

Farahi, R. H., Charrier, A. M., Tolbert, A., Lereu, A. L., Ragauskas, A., Davison, B. H., & Passian, A. (2017). Plasticity, elasticity, and adhesion energy of plant cell walls: Nanometrology of lignin loss using atomic force microscopy. Scientific Reports, 7(1), 152-12. doi:10.1038/s41598-017-00234-4

Fee, T., Surianarayanan, S., Downs, C., Zhou, Y., & Berry, J. (2016). Nanofiber alignment regulates NIH3T3 cell orientation and cytoskeletal gene expression on electrospun PCL+Gelatin nanofibers. PloS One, 11(5), e0154806. doi:10.1371/journal.pone.0154806
Feng, Y., Okamoto, R. J., Namani, R., Genin, G. M., & Bayly, P. V. (2013). Measurements of mechanical anisotropy in brain tissue and implications for transversely isotropic material models of white matter. Journal of the Mechanical Behavior of Biomedical Materials, 23, 117-132. doi: 10.1016/j.jmbbm.2013.04.007
Fontana, G., Gershlak, J., Adamski, M., Lee, J., Matsumoto, S., Le, H. D., . . . Murphy, W. L. (2017). Biofunctionalized plants as diverse biomaterials for human cell culture. Advanced Healthcare Materials, 6(8), n/a. doi:10.1002/adhm.201601225
Foolen, J., Wunderli, S. L., Loerakker, S., & Snedeker, J. G. (2018). Tissue alignment enhances remodeling potential of tendon-derived cells—lessons from a novel microtissue model of tendon scarring. Matrix Biology, 65, 14-29. doi:10.1016/j.matbio.2017.06.002
Gershlak, J., Hernandez, S., Fontana, G., Perreault, L., Hansen, K., Larson, S., . . . Gaudette, G. (2017). Crossing kingdoms: Using decellularized plants as perfusable tissue engineering scaffolds. Biomaterials, 125, 13-22. doi: 10.1016/j.biomaterials.2017.02.011
Gingras, J., Rioux, R. M., Cuvelier, D., Geisse, N. A., Lichtman, J. W., Whitesides, G. M., . . . Sanes, J. R. (2009). Controlling the orientation and synaptic differentiation of myotubes with micropatterned substrates. Biophysical Journal, 97(10), 2771-2779. doi:10.1016/j.bpj.2009.08.038
Glawe, J. D., Hill, J. B., Mills, D. K., & McShane, M. J. (2005). Influence of channel width on alignment of smooth muscle cells by high-aspect-ratio microfabricated elastomeric cell culture scaffolds. Journal of Biomedical Materials Research. Part A, 75(1), 106-114. doi:10.1002/jbm.a.30403
Goedecke, N., Bollhalder, M., Bernet, R., Silvan, U., & Snedeker, J. (2015). Easy and accurate mechano-profiling on micropost arrays MyJove Corporation. doi:10.5167/uzh-120364
Hayman, E. G., Pierschbacher, M. D., Suzuki, S., & Ruoslahti, E. (1985). Vitronectin—A major cell attachment promoting protein in fetal bovine serum. Experimental Cell Research, 160(2), 245-258. doi:10.1016/0014-4827(85)90173-9
Hepworth, D. G. & Vincent, J. F. V. (1998). The mechanical properties of xylem tissue from tobacco plants (*Nicotiana tabacum*'Samsun'). Annals of Botany, 81(6), 751-759. doi:10.1006/anbo.1998.0631
Hickey, R. J., Modulevsky, D. J., Cuerrier, C. M., & Pelling, A. E. (2018). Customizing the shape and microenvironment biochemistry of biocompatible macroscopic plant-derived cellulose scaffolds. ACS Biomaterials Science & Engineering, doi:10.1021/acsbiomaterials.8b00178
Customizing the Shape and Microenvironment Biochemistry of Biocompatible Macroscopic Plant-Derived Cellulose Scaffolds Ryan J. Hickey, Daniel J. ACS Biomaterials Science & Engineering 2018 4 (11), 3726-3736
Huang, N. F., Lee, R. J., & Li, S. (2010). Engineering of aligned skeletal muscle by micropatterning e-Century Publishing Corporation.
Hume, S. L., Hoyt, S. M., Walker, J. S., Sridhar, B. V., Ashley, J. F., Bowman, C. N., & Bryant, S. J. (2012). Alignment of multi-layered muscle cells within three-dimensional hydrogel macrochannels. Acta Biomaterialia, 8(6), 2193-2202. doi:10.1016/j.actbio.2012.02.001
Hunter, I. W., & Lafontaine, S. (1992). A comparison of muscle with artificial actuators. Paper presented at the 178-185. doi:10.1109/SOLSEN.1992.228297
Ishizaki, T., Saito, N., & Takai, O. (2010). Correlation of cell adhesive behaviors on superhydrophobic, superhydrophilic, and micropatterned superhydrophobic/superhydrophilic surfaces to their surface chemistry. Langmuir:The ACS Journal of Surfaces and Colloids, 26(11), 8147-8154. doi:10.1021/1a904447c
Idota, N., Tsukahara, T., Sato, K., Okano, T., & Kitamori, T. (2009). The use of electron beam lithographic graft polymerization on thermoresponsive polymers for regulating the directionality of cell attachment and detachment. Biomaterials, 30(11), 2095-2101. doi:10.1016/j.biomaterials.2008.12.058
Karam, G. N. (2005). Biomechanical model of the xylem vessels in vascular plants. Annals of Botany, 95(7), 1179-1186. doi:10.1093/aob/mci130
Komuro, T., Desaki, J., & Uehara, Y. (1982). Three-dimensional organization of smooth muscle cells in blood vessels of laboratory rodents. Cell and Tissue Research, 227(2), 429-437. doi:10.1007/BF00210897
Kuppan, P., Sethuraman, S., & Krishnan, U. M. (2016). Interaction of human smooth muscle cells on random and aligned nanofibrous scaffolds of PHBV and PHBV-gelatin. International Journal of Polymeric Materials and Polymeric Biomaterials, 65(16), 816. doi:10.1080/00914037.2016.1163562
Lam, M. T., Sim, S., Zhu, X., & Takayama, S. (2006). The effect of continuous wavy micropatterns on silicone substrates on the alignment of skeletal muscle myoblasts and myotubes. Biomaterials, 27(24), 4340-4347. doi:10.1016/j.biomaterials.2006.04.012
Leclerc, A., Tremblay, D., Hadjiantoniou, S., Bukoreshtliev, N. V., Rogowski, J. L., Godin, M., & Pelling, A. E. (2013). Three dimensional spatial separation of cells in response to microtopography. Biomaterials, 34(33), 8097-8104. doi: 10.1016/j.biomaterials.2013.07.047
Lee, D. R. (1981). Elasticity of phloem tissues. Journal of Experimental Botany, 32(126), 251-260.
Levy-Mishali, M., Zoldan, J., & Levenberg, S. (2009). Effect of scaffold stiffness on myoblast differentiation. Tissue Engineering. Part A, 15(4), 935-944. doi:10.1089/ten.tea.2008.0111
Liu, B., Qu, M., Qin, K., Li, Z., Li, H., Shen, B., & Jiang, Z. (2008;2007;). Role of cyclic strain frequency in regulating the alignment of vascular smooth muscle cells in vitro. Biophysical Journal, 94(4), 1497-1507. doi: 10.1529/biophysj.106.098574
Liao, I., Liu, J. B., Bursac, N., & Leong, K. W. (2008). Effect of electromechanical stimulation on the maturation of myotubes on aligned electrospun fibers. Cellular and Molecular Bioengineering, 1(2), 133-145. doi:10.1007/s12195-008-0021-y
Lourenco, A., Rencoret, J., Chemetova, C., Gominho, J., Gutierrez, A., del Rio, J. C., & Pereira, H. (2016). Lignin composition and structure differs between xylem, phloem and phellem in quercus suber L. Frontiers in Plant Science, 7doi:10.3389/fpls.2016.01612
Modulevsky, D. J., Lefebvre, C., Haase, K., Al-Rekabi, Z., & Pelling, A. E. (2014). Apple derived cellulose scaffolds for 3D mammalian cell culture. PLoS One, 9(5), e97835. doi:10.1371/journal.pone.0097835
Modulevsky, D. J., Cuerrier, C. M., & Pelling, A. E. (2016). Biocompatibility of subcutaneously implanted plant-derived cellulose biomaterials. PLoS One, 11(6), e0157894. doi:10.1371/journal.pone.0157894

Myburg, A. A., Lev-Yadun, S. and Sederoff, R. R. (2013). Xylem Structure and Function. In eLS, John Wiley & Sons, Ltd (Ed.). doi:10.1002/9780470015902.a0001302.pub2
Olivieri, M. P., Kittle, K. H., Tweden, K. S., & Loomis, R. E. (1992). Comparative biophysical study of adsorbed calf serum, fetal bovine serum and mussel adhesive protein films. Biomaterials, 13(4), 201-208. doi:10.1016/0142-9612(92)90185-Q
Papenburg, B. J., Roigues, E. D., Roigues, E. D., Wessling, M., & Stamatialis, D. (2010). Insights into the role of material surface topography and wettability on cell-material interactions. Soft Matter, 6(18), 4377-4388. doi:10.1039/b927207k
Recknor, J. B., Sakaguchi, D. S., & Mallapragada, S. K. (2006). Directed growth and selective differentiation of neural progenitor cells on micropatterned polymer substrates. Biomaterials, 27(22), 4098-4108. doi: 10.1016/j.biomaterials.2006.03.029
Roman, W., & Gomes, E. R. (2018). Nuclear positioning in skeletal muscle. Seminars in Cell & Developmental Biology, 82, 51-56. doi:10.1016/j.semcdb.2017.11.005
Scarpella, E., & Meijer, A. (2004). Pattern formation in the vascular system of monocot and dicot plant species. New Phytologist, 164(2), 209-242.
Schoenenberger, A. D., Foolen, J., Moor, P., Silvan, U., & Snedeker, J. G. (2018). Substrate fiber alignment mediates tendon cell response to inflammatory signaling. Acta Biomaterialia, 71, 306-317. doi:10.1016/j.actbio.2018.03.004
Schuetz, M., Smith, R., & Ellis, B. (2013). Xylem tissue specification, patterning, and differentiation mechanisms. Journal of Experimental Botany, 64(1), 11-31. doi:10.1093/jxb/ers287
Schulz, A. and Thompson, G. A. (2009). Phloem Structure and Function. In eLS, (Ed.). doi:10.1002/9780470015902.a0001290.pub2
Soliman, E., Bianchi, F., Sleigh, J. N., George, J. H., Cader, M. Z., Cui, Z., & Ye, H. (2018). Aligned electrospun fibers for neural patterning. Biotechnology Letters, 40(3), 601-607. doi:10.1007/s10529-017-2494-z
Sun, Y., Duffy, R., Lee, A., & Feinberg, A. W. (2013). Optimizing the structure and contractility of engineered skeletal muscle thin films. Acta Biomaterialia, 9(8), 7885-7894. doi:10.1016/j.actbio.2013.04.036
Tanaka, T., Hattori-Aramaki, N., Sunohara, A., Okabe, K., Sakamoto, Y., Ochiai, H., . . . Kishi, K. (2014). Alignment of skeletal muscle cells cultured in collagen gel by mechanical and electrical stimulation. International Journal of Tissue Engineering, 2014, 1-5. doi:10.1155/2014/621529
Tan, Z., Liu, T., Zhong, J., Yang, Y., & Tan, W. (2017). Control of cell growth on 3D-printed cell culture platforms for tissue engineering. Journal of Biomedical Materials Research Part A, 105(12), 3281-3292. doi:10.1002/jbm.a.36188
Tijore, A., Irvine, S. A., Sarig, U., Mhaisalkar, P., Baisane, V., & Venkatraman, S. (2018). Contact guidance for cardiac tissue engineering using 3D bioprinted gelatin patterned hydrogel. Biofabrication, 10(2), 025003. doi: 10.1088/1758-5090/aaa15d
Thorsteinsdóttir, S., Deries, M., Cachaco, A. S., & Bajanca, F. (2011). The extracellular matrix dimension of skeletal muscle development. Developmental Biology, 354(2), 191-207. doi:10.1016/j.ydbio.2011.03.015
Tobimatsu, Y., Wagner, A., Donaldson, L., Mitra, P., Niculaes, C., Dima, O., . . . Ralph, J. (2013). Visualization of plant cell wall lignification using fluorescence-tagged monolignols. The Plant Journal, 76(3), 357-366. doi:10.1111/tpj.12299
Wang, P., Yu, H., & Tsai, W. (2010). Modulation of alignment and differentiation of skeletal myoblasts by submicron ridges/grooves surface structure. Biotechnology and Bioengineering, 106(2), 285-n/a. doi:10.1002/bit.22697
Wang, P., Li, W., Yu, J., & Tsai, W. (2012). Modulation of osteogenic, adipogenic and myogenic differentiation of mesenchymal stem cells by submicron grooved topography. Journal of Materials Science: Materials in Medicine, 23(12), 3015-3028. doi:10.1007/s10856-012-4748-6
Webb, K., Hlady, V., & Tresco, P. A. (1998). Relative importance of surface wettability and charged functional groups on NIH 3T3 fibroblast attachment, spreading, and cytoskeletal organization. Journal of Biomedical Materials Research, 41(3), 422-430. doi:10.1002/(SICI)1097-4636(19980905)41:33.0.CO;2-K
Wells, R. G. (2008). The role of matrix stiffness in regulating cell behavior. Hepatology, 47(4), 1394-1400. doi:10.1002/hep.22193
Yeong, W. Y., Yu, H., Lim, K. P., Ka Lai Gary Ng, Yin Chiang Freddy Boey, Subbu, V. S., & Tan, L. P. (2010). Multiscale topological guidance for cell alignment via direct laser writing on biodegradable polymer. Tissue Engineering Part C: Methods, 16(5), 1011. doi:10.1089/ten.tec.2009.0604
Zhao, Y., Zeng, H., Nam, J., & Agarwal, S. (2009). Fabrication of skeletal muscle constructs by topographic activation of cell alignment. Biotechnology and Bioengineering, 102(2), 624-631. doi:10.1002/bit.22080

All references cited herein and elsewhere in the specification are herein incorporated by reference in their entireties.

What is claimed is:

1. A composite scaffold biomaterial comprising:

two or more scaffold biomaterial subunits, each comprising a decellularized plant or fungal tissue from which cellular materials and nucleic acids of the tissue are removed, the decellularized plant or fungal tissue comprising a 3-dimensional porous structure;

the two or more scaffold biomaterial subunits being assembled into the composite scaffold biomaterial and held together via; gel casting using a hydrogel glue in combination with complementary/interlocking geometry of the two or more scaffold biomaterial subunits, or chemical cross-linking in combination with complementary/interlocking geometry of the two or more scaffold biomaterial subunits; or any combinations thereof, wherein the composite scaffold biomaterial is cellulose-based.

2. The composite scaffold biomaterial of claim 1, wherein the two or more scaffold biomaterial subunits are additionally held together via guided assembly based biolithography.

3. The composite scaffold biomaterial of claim 1, wherein the hydrogel glue comprises gelatin, collagen, agarose, hyaluronic acid, alginate, fibrin, fibronectin, agar, PEG, PVA, or any combinations thereof.

4. The composite scaffold biomaterial of claim 1, wherein the two or more scaffold biomaterial subunits act as a scaffold for the hydrogel glue to form around.

5. The composite scaffold biomaterial of claim 1, wherein at least a portion of the two or more scaffold biomaterial subunits are coated with the hydrogel glue.

6. The composite scaffold biomaterial of claim 1, wherein the hydrogel glue comprises gelatin, which is cross-linked with glutaraldehyde and sodium borohydride reduction.

7. The composite scaffold biomaterial of claim 1, wherein the hydrogel glue further comprises one or more agents wherein the one or more agents is a therapeutic drug, a signalling-molecule, a growth factor, a metabolite, an ECM protein or component, or any combinations thereof.

8. The composite scaffold biomaterial of claim 1, wherein the complementary interlocking geometry of the two or more scaffold biomaterial subunits comprises a peg-and-hole friction-fit interlocking geometry.

9. The composite scaffold biomaterial of claim 1, wherein at least one of the scaffold biomaterial subunits comprises or is seeded with a first cell type optionally wherein at least one other scaffold biomaterial subunit comprises or is seeded with a second cell type.

10. The composite scaffold biomaterial of claim 9, wherein the composite scaffold biomaterial comprises an interface between adjacent scaffold biomaterial subunits which mimics a tissue interface, such as a bone-fibroblast tissue interface.

11. The composite scaffold biomaterial of claim 9, wherein the scaffold biomaterials comprise ECM deposition at least one interface between adjacent scaffold biomaterial subunits.

12. The composite scaffold biomaterial of claim 2, wherein the two or more scaffold biomaterial subunits are assembled into the composite scaffold biomaterial and held together via guided assembly based biolithography (GAB).

13. The composite scaffold biomaterial of claim 12, wherein the two or more scaffold biomaterial subunits comprise at least one subunit comprising plant or fungus-derived biomaterial, and at least one subunit comprising a bacterial cellulose.

14. The composite scaffold biomaterial of claim 1, wherein the two or more scaffold biomaterial subunits are assembled into the composite scaffold biomaterial and held together via chemical cross-linking.

15. The composite scaffold biomaterial of claim 14, wherein at least a portion of two or more of the scaffold biomaterial subunits are modified to feature carboxymethyl and/or hydroxyl ethyl cellulose functional groups, which are cross-linked together by citric acid and heated to hold the composite scaffold biomaterial together.

16. The composite scaffold biomaterial of claim 1, further comprising one or more agents, wherein the one or more agents is a therapeutic drug, a signalling molecule, a growth factor, a metabolite, an ECM protein or component, or any combinations thereof.

17. The composite scaffold biomaterial of claim 1, wherein the decellularized plant or fungal tissue is hemicellulose-based, chitin-based, chitosan-based, pectin-based, lignin-based, lignan-based, or any combinations thereof.

18. A method for tissue repair or regeneration; for providing an implant; for culturing one or more cell types; for mimicking an in vivo tissue or tissue interface; for bone tissue engineering; for repair or regeneration of bone; for transporting a fluid or liquid; for mimicking a tissue interface; for wound healing; for delivery of a therapeutic drug, a signalling molecule, a growth factor, a metabolite, an ECM protein or component, or any combinations thereof; or any combinations thereof; in a subject in need thereof, said method comprising:

providing the composite scaffold biomaterial of claim 1; and introducing the composite scaffold biomaterial to the subject at a site in need thereof.

* * * * *